United States Patent
Mason et al.

(10) Patent No.: US 11,408,812 B2
(45) Date of Patent: Aug. 9, 2022

(54) HIGH DENSITY DEPOSITION FOR ARRAY PRODUCTION

(71) Applicant: Becton, Dickinson and Company, Franklin Lakes, NJ (US)

(72) Inventors: Clark Mason, Franklin Lakes, NJ (US); Timothy W. Petersen, Franklin Lakes, NJ (US); Vladimir Azersky, Franklin Lakes, NJ (US); Christopher J. Wolf, Franklin Lakes, NJ (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 480 days.

(21) Appl. No.: 15/491,719

(22) Filed: Apr. 19, 2017

(65) Prior Publication Data

US 2017/0307502 A1 Oct. 26, 2017

Related U.S. Application Data

(60) Provisional application No. 62/333,770, filed on May 9, 2016, provisional application No. 62/333,098, filed on May 6, 2016, provisional application No. 62/326,358, filed on Apr. 22, 2016.

(51) Int. Cl.
| | | |
|---|---|---|
| *G01N 15/10* | (2006.01) | |
| *G01N 15/14* | (2006.01) | |
| *B01L 3/02* | (2006.01) | |
| *B01J 19/00* | (2006.01) | |
| *B01L 3/00* | (2006.01) | |
| *C12M 1/00* | (2006.01) | |

(52) U.S. Cl.
CPC .......... *G01N 15/14* (2013.01); *B01J 19/0046* (2013.01); *B01L 3/0241* (2013.01); *B01L 3/5085* (2013.01); *G01N 15/1404* (2013.01); *G01N 15/1459* (2013.01); *B01J 2219/00317* (2013.01); *B01J 2219/00547* (2013.01); *B01J 2219/00572* (2013.01); *B01J 2219/00648* (2013.01); *B01J 2219/00743* (2013.01); *B01L 2200/0642* (2013.01); *B01L 2200/0652* (2013.01); *B01L 2300/0627* (2013.01); *B01L 2300/0819* (2013.01); *B01L 2300/0829* (2013.01); *B01L 2300/0893* (2013.01); *C12M 47/04* (2013.01); *G01N 2015/1006* (2013.01); *G01N 2015/1415* (2013.01)

(58) Field of Classification Search
CPC ..................................................... G01N 15/14
USPC ........................................................ 506/13
See application file for complete search history.

(56) References Cited

U.S. PATENT DOCUMENTS

| | | |
|---|---|---|
| 3,960,449 A | 6/1976 | Carleton et al. |
| 4,347,935 A | 9/1982 | Merrill |
| 4,667,830 A | 5/1987 | Nozaki et al. |
| 4,704,891 A | 11/1987 | Recktenwald et al. |
| 4,770,992 A | 9/1988 | Van den Engh et al. |
| 5,030,002 A | 7/1991 | North, Jr. |
| 5,040,890 A | 8/1991 | North, Jr. |
| 5,047,321 A | 9/1991 | Loken et al. |
| 5,245,318 A | 9/1993 | Tohge et al. |
| 5,317,162 A | 5/1994 | Pinsky et al. |
| 5,464,581 A | 11/1995 | van den Engh |
| 5,483,469 A | 1/1996 | Van den Engh et al. |
| 5,602,039 A | 2/1997 | Van den Engh |
| 5,620,842 A | 4/1997 | Davis et al. |
| 5,627,040 A | 5/1997 | Bierre et al. |
| 5,643,796 A | 7/1997 | Van den Engh et al. |
| 5,700,692 A | 12/1997 | Sweet |
| 6,372,506 B1 | 4/2002 | Norton |
| 6,809,804 B1 | 10/2004 | Yount et al. |
| 6,813,017 B1 | 11/2004 | Hoffman et al. |
| 6,821,740 B2 | 11/2004 | Darzynkiewicz et al. |
| 7,129,505 B2 | 10/2006 | Oostman et al. |
| 7,201,875 B2 | 4/2007 | Norton et al. |
| 7,544,326 B2 | 6/2009 | Norton et al. |
| 8,140,300 B2 | 3/2012 | Dunne et al. |
| 8,233,146 B2 | 7/2012 | Chen |
| 8,753,573 B2 | 6/2014 | van Den Engh et al. |
| 8,975,595 B2 | 3/2015 | Norton et al. |
| 9,029,724 B2 | 5/2015 | Hashimoto et al. |
| 9,092,034 B2 | 7/2015 | Vrane et al. |
| 9,095,494 B2 | 8/2015 | Warner et al. |
| 9,097,640 B2 | 8/2015 | Goldberg et al. |

(Continued)

FOREIGN PATENT DOCUMENTS

| | | |
|---|---|---|
| EP | 1 691 196 | 8/2006 |
| WO | WO 16/118915 | 7/2016 |

OTHER PUBLICATIONS

Bose et al (Genome Biology 16:120 16 pages) (Year: 2015).*
Lindstrom et al (Biochimica et Biophysica Acta 1810: 308-316 (Year: 2011).*
Alison et al., Dec. 2010, Finding cancer stem cells: are aldehyde dehydrogenases fit for purpose?, J Pathol, 222(4):335-344.

(Continued)

*Primary Examiner* — Christopher M Gross

(74) *Attorney, Agent, or Firm* — Bret E. Field; Bozicevic, Field & Francis LLP

(57) ABSTRACT

Disclosed herein are methods for producing high density cellular arrays. In some embodiments, the methods comprise: providing a sample comprising a plurality of cells; and introducing the plurality of cells in the sample into microwells of a microwell array to produce a cellular array, wherein the microwell array comprises 500 or more microwells per inch$^2$, and wherein 25% or more of the microwells of the cellular array comprise a single cell. The disclosed methods can be used for producing a high density synthetic particle array and a high density reagent array.

17 Claims, 14 Drawing Sheets

(56) References Cited

U.S. PATENT DOCUMENTS

| | | | | |
|---|---|---|---|---|
| 2010/0035243 | A1* | 2/2010 | Muller | B82Y 15/00 |
| | | | | 435/6.11 |
| 2012/0094324 | A1* | 4/2012 | Durack | C12M 23/12 |
| | | | | 435/34 |
| 2013/0078163 | A1 | 3/2013 | Chung et al. | |
| 2013/0216508 | A1* | 8/2013 | Anversa | C12N 5/0689 |
| | | | | 424/93.7 |
| 2014/0144817 | A1* | 5/2014 | Hashimoto | G01N 15/14 |
| | | | | 209/552 |
| 2016/0253584 | A1* | 9/2016 | Fodor | G06K 19/06103 |
| | | | | 235/494 |

OTHER PUBLICATIONS

Dalerba et al., 2011, Single-cell dissection of transcriptional heterogeneity in human colon tumors, Nat Biotechnol., 29(12):1120-1127 and Supplementary Material.

Deutsch et al., Jun. 2, 2006, A novel miniature cell retainer for correlative high-content analysis of individual untethered non-adherent cells, Lab on a Chip, 6:995-1000.

Herbig, et al. 2007, Crit Rev Ther Drug Carrier Syst. 24(3):203-255.

Kay et al., 1976, Laser Stroboscopic photography technique for cell orientation studies in flow, The Journal of Histochemistry and Cytochemistry, 24(1):265-268.

Linden, et al., Oct. 2004, Application of flow cytometry to platelet disorders, Semin Throm Hemost., 30(5):502-11.

Lindstrom, Nov. 13, 2009, Microwell devices for single-cell analyses, Royal institute of Technology, Thesis, Royal Institute of Technology, 88 pp.

Steen et al. 1993, Pulse modulation of the excitation light source boosts the sensitivity of an arc lamp-based flow cytometer, Cytometry, 14(2): 115-122.

Taylor et al., Feb. 15, 2000, Application of high-density optical microwell arrays in a live-cell biosensing system, Analytical Biochemistry, 285:132-142.

Virgo et al., 2012, Flow cytometry in clinical pathology, Ann Clin Biochem. 49(pt 1): 17-28.

Wang et al., Nov. 17, 2011, Trapping cells on a stretchable microwell array for single-cell analysis, Analytical and Bioanalytical Chemistry, 402(3): 1065-1072.

Yamamura et al., Nov. 12, 2005, Single-cell microarray for analyzing cellular response, Analytical Chemistry, 77(24):8050-8056.

International Search Report and Written Opinion dated Sep. 15, 2017 in PCT/US2017/028438.

* cited by examiner

HIGH DENSITY DEPOSITION FOR ARRAY PRODUCTION

RELATED APPLICATIONS

The present application claims priority under 35 U.S.C. § 119(e) to U.S. Provisional Application No. 62/326,358, entitled "HIGH DENSITY DEPOSITION FOR ARRAY PRODUCTION," filed on Apr. 22, 2016; U.S. Provisional Application No. 62/333,098, entitled "AUTOMATED SET-UP FOR CELL SORTING," filed on May 6, 2016; and U.S. Provisional Application No. 62/333,770, entitled "AUTOMATED SET-UP FOR CELL SORTING," filed on May 9, 2016; the content of each of these related applications is hereby incorporated by reference in its entirety.

BACKGROUND

Field

The present disclosure relates generally to the field of high density deposition to produce arrays, for example cellular arrays or droplet arrays.

Description of the Related Art

Methods and techniques such as flow cytometry have been developed to deposit cells into 96-well microtiter plates. Methods and techniques such as gravity deposition of low concentration samples have been developed to deposit single cells into microwells with 15% occupancy rate. However, there is still a need for methods and systems that are able to produce high density microwell arrays with high specificity, accuracy, and occupancy rates.

SUMMARY

The present disclosure provides methods for producing a cellular array. In some embodiments, the methods comprise: providing a sample comprising a plurality of cells; and introducing the plurality of cells in the sample into microwells of a microwell array to produce the cellular array, wherein the microwell array comprises 500 or more microwells per inch$^2$, and wherein 25% or more of the microwells of the cellular array comprise a single cell. Introducing the plurality of cells in the sample into the microwells of the microwell array comprises introducing the plurality of cells in the sample into the microwells of the microwell array at a plurality of first desired locations. Introducing the plurality of cells in the sample into the microwells of the microwell array at the plurality of first desired locations comprises introducing a cell of interest from the plurality of cells at one of the plurality of first desired locations.

In some embodiments, 50% or more of the microwells of the cellular array comprise a single cell. In some embodiments, the microwell array comprises 1000 or more microwells per inch$^2$. Each of the microwells of the microwell array has a volume no more than 1000 nanoliters or no more than 400 nanoliters. Each of the microwells of the microwell array has a diameter no more than 1000 micrometers or no more than 400 micrometers. At least two of the microwells of the microwell array are separated from each other by no more than 200 micrometers or no more than 80 micrometers.

In some embodiments, introducing the plurality of cells into the microwells of the microwell array comprises flow cytometrically depositing the plurality of cells into the microwells of the microwell array. Flow cytometrically depositing the plurality of cells into the microwells of the microwell array comprises using a flow cytometer to deposit a single cell at a time into the microwells of the microwell array.

In some embodiments, the methods further comprise introducing a reagent into one or more of the microwells of the microwell array before the plurality of cells are introduced into the microwells of the microwell array. In some embodiments, the methods further comprise introducing a reagent into one or more of the microwells of the cellular array. The reagent comprises one or more synthetic particles. Introducing the reagent comprises flow cytomertrically depositing the reagent into the microwells. The one or more synthetic particles comprise beads.

In some embodiments, the methods further comprise introducing synthetic particles into the microwells of the microwell array at a plurality of second desired locations. In some embodiments, the methods further comprise introducing a synthetic particle of interest into the microwells of the microwell array at one of the plurality of second desired locations, wherein one of the synthetic particles differs from the others of the synthetic particles, wherein introducing synthetic particles into one or more of the microwells of the microwell array comprises introducing the one of the synthetic particles into a microwell of the microwell array at a second desired location. Introducing synthetic particles into the microwells of the microwell array comprises flow cytometrically deposing the synthetic particles into the microwells of the microwell array. The one or more synthetic particles comprise magnetic beads attached with oligonucleotide barcodes.

In some embodiments, the methods further comprise aligning a sorting component of a flow cytometer with the microwell array.

Disclosed herein are methods for producing droplet arrays. In some embodiments, the methods comprise introducing a plurality of first droplets into microwells of a microwell array to produce a first droplet array, wherein the microwell array comprises 500 or more microwells per inch$^2$, wherein 25% or more of the microwells of the first droplet array comprise only a single first droplet.

In some embodiments, 50% or more of the microwells of the first droplet array comprise only a single first droplet. In some embodiments, the microwell array comprises 1000 or more microwells per inch$^2$. Each of the microwells of the microwell array has a volume no more than 1000 nanoliters or no more than 400 nanoliters. Each of the microwells of the microwell array has a diameter no more than 1000 micrometers or no more than 200 micrometers.

In some embodiments, the methods further comprise introducing a plurality of second droplets into the microwells of the first droplet array to produce a second droplet array, wherein 25% or more of the microwells of the second droplet array comprise a single first droplet and a single second droplet. In some embodiments, the methods further comprise introducing a plurality of second droplets into the microwells of the microwell array before the plurality of first droplets are introduced into the microwells of the microwell array to produce a second droplet array, wherein 25% or more of the microwells in the second droplet array comprise a single first droplet and a single second droplet.

In some embodiments, each of the plurality of first droplets and the plurality of second droplets comprises a single cell or a synthetic particle respectively. The synthetic particle comprises a bead attached with a plurality of oligonucleotide barcodes. Each of the plurality of oligonucleotide barcodes is the same or different from at least one other of the plurality of oligonucleotide barcodes. A second droplet of the plurality of second droplets further comprises a reagent. Introducing the plurality of first droplets comprises flow cytometrically depositing the plurality of first droplets into the microwells of the microwell array. Flow cytometrically depositing the plurality of first droplets into the microwells of the microwell array comprises using a flow cytometer to deposit a single first droplet at a time into the microwells of the microwell array.

Disclosed herein are cellular arrays. In some embodiments, a cellular array comprises a microwell array comprising 500 or more microwells per inch$^2$, wherein 25% or more of the microwells of the microwell array comprise a single cell.

In some embodiments, 50% or more of the microwells comprise a single cell. The microwell array comprises 1000 or more microwells per inch$^2$. Each of the microwells of the microwell array has a volume no more than 1000 nanoliters or no more than 400 nanoliters. Each of the microwells of the microwell array has a diameter of no more than 1000 micrometers or no more than 400 micrometers. At least two of the microwells of the microwell array are separated from each other by no more than 200 micrometers or no more than 80 micrometers.

In some embodiments, 25% or more of the microwells of the microwell array comprises a single cell and a synthetic particle. The synthetic particle comprises a bead attached with a plurality of oligonucleotide barcodes.

Disclosed herein are methods for aligning a first alignment microwell array for producing a sample microwell array. In some embodiments, the methods comprise: (a) determining a first parameter using a first imaging sensor and a second parameter using a second imaging sensor, wherein the first imaging sensor and the second imaging sensor are approximately orthogonal to each other and are located between a waste receiving vessel and the first alignment microwell array; (b) providing a desired location on the first alignment microwell array in an x direction and a y direction; (c) depositing a first alignment droplet into a microwell of the first alignment microwell array based on the first parameter and the second parameter, wherein the first parameter is related to the desired location in the x direction, and wherein the second parameter is related to the desired location in the y direction; (d) determining the distance between the first alignment droplet's location on the first alignment microwell array and the desired location; (e) adjusting the first parameter and the second parameter based on the distance between the first alignment droplet's location on the first alignment microwell array and the desired location if the distance is greater than a predetermined threshold value; and (f) repeating steps (b)-(e) until the distance between the first alignment droplet's location on the first alignment microwell array and the desired location is no more than the predetermined threshold value.

Determining the distance between the first alignment droplet's location on the first alignment microwell array and the desired location comprises imaging the first alignment microwell array and the first alignment droplet using the first imaging sensor and imaging the first alignment array and the first alignment droplet using the second imaging sensor. Adjusting the first parameter and the second parameter based on the distance between the first alignment droplet's location on the first alignment microwell array and the desired location comprises determining the first alignment droplet's location on the first alignment microwell array based on the imaging of the first alignment microwell array and the first alignment droplet by the first imaging sensor and the imaging of the first alignment microwell and the first alignment droplet by the second imaging sensor.

In some embodiments, depositing the first alignment droplet into the microwell of the first alignment microwell array comprises: depositing the first alignment droplet into an alignment device of the first alignment microwell array, and wherein determining the distance between the first alignment droplet's location on the first alignment microwell array and the desired location comprises imaging the alignment device and the first alignment droplet on the alignment device using the first imaging sensor and imaging the alignment device and the first alignment droplet on the alignment device using the second imaging sensor.

In some embodiments, the alignment device comprises a plurality of alignment regions. Two alignment regions of the plurality of alignment regions can comprise approximately equal areas. The plurality of alignment regions can comprise a plurality of concentric rings. Two concentric rings of the concentric rings can be separated from each other by 0.1 mm. Two concentric rings of the concentric rings can be separated from each other by 1 mm.

In some embodiments, the first parameter is related to droplet charge. The second parameter is related to the first alignment droplet's location in the y direction on the first alignment microwell array. The first imaging sensor is a CCD camera or a CMOS camera. The second imaging sensor is a CMOS camera or a CCD camera.

In some embodiments, depositing the first alignment droplet into the microwell of the first alignment microwell array comprises flow cytometrically depositing the first alignment droplet into the microwell of the first alignment microwell array. The predetermined threshold value correlates to the first alignment droplet's distance from an edge of the waste receiving vessel.

In some embodiments, the methods further comprise introducing a sample droplet into a microwell of the sample microwell array based on the first parameter and the second parameter. In some embodiments, the methods can comprise introducing a plurality of sample droplets into microwells of the sample microwell array based on the first parameter and the second parameter. The plurality of sample droplets comprises cells, particles attached with oligonucleotide barcodes, or any combination thereof.

In some embodiments, the methods further comprise: introducing a second alignment droplet into a microwell of a second alignment microwell array before the plurality of sample droplets are introduced into the microwells of the sample array; and determining the second alignment droplet's location on the second alignment microwell array using the second imaging sensor, wherein introducing the plurality of sample droplets into the microwells of the sample microwell array is further based on the second alignment droplet's location on the second alignment array.

In some embodiments, providing the desired location in the x direction on the first alignment microwell array comprises using the first imaging sensor to determine the desired location in the x direction on the first alignment microwell array and providing the desired location in the y direction on the first alignment microwell array comprises using the second imaging sensor to determine the desired location in the y direction on the sample array.

Also disclosed herein are systems for producing cellular arrays. In some embodiments, a system comprises: a cell sorting component configured to: flow cytometrically introduce droplets into microwells of a microwell array to produce a cellular array, wherein the microwell array comprises 500 or more microwells per inch; and a control component configured to: receive a desired location in an x direction and a y direction on the microwell array; and determine a first parameter using a first imaging sensor and a second parameter using a second imaging sensor for introducing the droplet into a microwell of the microwell array, wherein the first imaging sensor and the second imaging sensor are approximately orthogonal to each other and are between a waste receiving vessel and the microwell array, and wherein the distance between the droplet's location and the desired location is within a predetermined threshold.

In some embodiments, the system can comprise the microwell array, wherein the microwell array is in a droplet receiving relationship to the cell sorting component.

In some embodiments, the droplet comprises a cell or a synthetic particle. The synthetic particle comprises a magnetic bead. The synthetic particle comprises a bead attached with oligonucleotide barcodes. Each of the microwells of the microwell array has a volume no more than 1000 nanoliters. Each of the microwells of the microwell array has a diameter of no more than 1000 micrometers. At least two of the microwells of the microwell array are separated from each other by no more than 200 micrometers.

In some embodiments, determining the first parameter and the second parameter comprises flow cytometrically depositing a first alignment droplet onto a microwell of a first alignment microwell array. The first parameter is related to drop charge and the second parameter is related to first alignment droplet's location on the first alignment microwell array in the y direction. The predetermined threshold correlates to the droplet's distance from an edge of the waste receiving vessel.

In some embodiments, the control component is further configured to introducing a plurality of cells into microwells of the microwell array based on the first parameter and the second parameter. The control component is further configured to: prior to introducing the plurality of cells into the microwells of the microwell array, introducing a second alignment droplet into a microwell of a second alignment microwell array; and determining the second alignment droplet's location on the second alignment microwell array, wherein introducing the plurality of cells into the microwells of the cellular array is further based on the second alignment droplet's location on the second alignment microwell array.

In some embodiments, the control component is configured to: receive the desired location in the x direction and the y direction on the microwell array; and determine the first parameter using the first imaging sensor and the second parameter using the second imaging sensor for introducing the droplet into the microwell of the microwell array, wherein the first imaging sensor and the second imaging sensor are approximately orthogonal to each other and are between a waste receiving vessel and the microwell array, and wherein the droplet's location and the desired location is within a predetermined threshold.

In some embodiments, the control component is configured to: receive the desired location in the x direction and the y direction on the microwell array; and determine the first parameter using the first imaging sensor and the second parameter using the second imaging sensor for introducing the droplet into the microwell of the microwell array, wherein the first imaging sensor and the second imaging sensor are approximately orthogonal to each other and are between a waste receiving vessel and the microwell array, and wherein the droplet's location and the desired location is within a predetermined threshold.

Disclosed herein are systems and methods for flow stream alignment. In some embodiments, the system comprises: an imaging sensor configured to capture one or more images of a flow stream in a detection field of a flow cytometer; and a processor comprising memory operably coupled to the processor, wherein the memory includes instructions stored thereon to determine one or more properties of the flow stream and generate a data signal corresponding to the one or more properties of the flow stream, wherein the processor is configured to automatically adjust one or more parameters of the flow stream in response to the data signal.

Disclosed herein are methods of aligning a flow stream. In some embodiments, the method comprises: (a) receiving a first parameter used to deposit a first alignment droplet to a desired location on a first alignment microwell array; (b) depositing a second alignment droplet to a second alignment microwell array using the first parameter; (c) determining a path of the second alignment droplet, from a cell sorting component to the second alignment microwell, in the first detection field using a first imaging sensor, wherein the first imaging sensor is located between the cell sorting component and a waste receiving vessel; and (d) determining a first measurement between a first position of a path of the first alignment droplet in the first detection field and a corresponding first position of the path of the second droplet in the first detection field.

In some embodiments, the method comprise: (e) if the first measurement is greater than a first predetermined threshold: adjusting the first parameter based on the first measurement; and repeating steps (b)-(d). In some embodiments, wherein receiving the first parameter used to deposit the first alignment droplet to the first desired location on the first alignment microwell array comprises: depositing the first alignment droplet to the desired location on the first alignment microwell array using the first parameter; and determining the path of the first alignment droplet in the first detection field using the first imaging sensor.

In some embodiments, the cell sorting component comprises a nozzle. The nozzle can comprise an orifice. The cell sorting component can comprise a deflection plate.

In some embodiments, the first parameter can be related to the desired location in the x direction. The first parameter can be related to droplet charge.

In some embodiments, depositing the first alignment droplet to the desired location on the first alignment microwell array using the first parameter comprises: depositing the first alignment droplet to the desired location on the first alignment microwell array using the first parameter and a second parameter. Depositing the second alignment droplet to the second alignment microwell array using the first parameter can comprise: depositing the second alignment droplet to the second alignment microwell array using the first parameter and the second parameter.

In some embodiments, the second parameter can be related to the desired location in the y direction. The second parameter can be related to droplet charge.

In some embodiments, the step (b) can comprise: determining a path of the first alignment droplet in a second detection field, using a second imaging sensor, from the deflection plate to the desired location on the first alignment microwell array, wherein the second imaging sensor is located between the waste receiving vessel and the deflection plate. The step (c) can comprise: determining a path of the second alignment droplet in the second detection field using the second imaging sensor. The step (d) can comprise: determining a second measurement between a second position of the path of the first alignment droplet in the second detection field and a corresponding second position of the path of the second droplet in the second detection field. The step (f) can comprise: if the second measurement is greater than a second predetermined threshold, adjusting the second parameter based on the second measurement.

In some embodiments, the first imaging sensor and the second imaging sensor are approximately orthogonal to each other. The first imaging sensor can be a CCD camera or a CMOS camera. The second imaging sensor can be a CCD camera or a CMOS camera.

In some embodiments, determining the path of the first alignment droplet in the first detection field can comprise capturing a first alignment image of the first alignment droplet in the first detection field. Determining the path of the second alignment droplet in the first detection field can comprise capturing a second alignment image of the second alignment droplet in the first detection field. Determining the path of the first alignment droplet in the first detection field can comprise determining a first channel, in the first alignment image, along the path of the first alignment droplet in the first detection field. The first measurement can comprise whether at least a part of the path of the second alignment droplet in the first detection field is within a corresponding first channel in the second alignment image.

In some embodiments, the first channel can be represented by two bars in the first alignment image, and wherein the corresponding first channel is represented by corresponding two bars in the second alignment image. The first measurement can comprise a first distance between the first position of the path of the first alignment droplet in the first detection field and the corresponding first position of the path of the second droplet in the first detection field.

In some embodiments, determining the path of the first alignment droplet in the second detection field can comprise capturing a third alignment image of the first alignment droplet in the second detection field. Determining the path of the second alignment droplet in the second detection field can comprise capturing a fourth alignment image of the second alignment droplet in the second detection field. Determining the path of the first alignment droplet in the second detection field can comprise determining a second channel, in the third alignment image, along the path of the first alignment droplet in the second detection field. The second measurement can comprise whether at least a part of the path of the second alignment droplet in the first detection field is within a corresponding second channel in the second alignment image.

In some embodiments, the second channel can be represented by two bars in the third alignment image, and wherein the corresponding second channel is represented by corresponding two bars in the fourth alignment image. The second measurement can comprise a second distance between the second position of the path of the first alignment droplet in the second detection field and the corresponding second position of the path of the second droplet in the first detection field.

In some embodiments, depositing the first alignment droplet to the desired location of the first alignment microwell array can comprise flow cytometrically depositing the first alignment droplet to the desired location of the first alignment microwell array. Depositing the second droplet using the first parameter can comprise flow cytometrically depositing the second using the first parameter.

In some embodiments, the method can comprise: introducing a sample droplet into a microwell of the sample microwell array based on the first parameter. The method can comprise: introducing a plurality of sample droplets into a plurality of microwells of the sample microwell array based on the adjusted first parameter. The plurality of sample droplets can comprise cells, particles attached with oligonucleotide barcodes, or any combination thereof.

Disclosed herein are systems for producing a cellular array. In some embodiments, the system comprises: a cell sorting component; non-transitory memory configured to store executable instructions; and a processor in communication with the cell sorting component and the non-transitory memory, the processor programmed by the executable instructions to: (a) receive a first parameter used to deposit the first alignment droplet to the desired location on the first alignment microwell array; (b) cause the cell sorting component deposit a second alignment droplet to a second alignment microwell array using the first parameter; and (c) determine a path of the second alignment droplet, from the cell sorting component to the second alignment microwell, in the first detection field using a first imaging sensor, wherein the first imaging sensor is located between the cell sorting component and a waste receiving vessel; and (d) determine a first measurement between a first position of a path of the first alignment droplet in the first detection field and a corresponding first position of the path of the second droplet in the first detection field.

In some embodiments, the processor is programmed to: cause the cell sorting component introduce droplets into microwells of a microwell array using the first parameter to produce a cellular array, wherein the microwell array comprises 500 or more microwells per inch2.

In some embodiments, the system can comprise the microwell array, wherein the microwell array is in a droplet receiving relationship to the cell sorting component. The droplet can comprise a cell or a synthetic particle. The synthetic particle can comprise a magnetic bead. The synthetic particle can comprise a bead attached with oligonucleotide barcodes. Each of the microwells of the microwell array can have a volume no more than 1000 nanoliters. Each of the microwells of the microwell array can have a diameter of no more than 1000 micrometers. At least two of the microwells of the microwell array can be separated from each other by no more than 200 micrometers.

In some embodiments, to determine the first parameter and the second parameter, the processor is programmed by the executable instructions to flow cytometrically deposit a first alignment droplet onto a microwell of a first alignment microwell array. The first parameter can be related to drop charge and the second parameter is related to first alignment droplet's location on the first alignment microwell array in the y direction.

The processor can be programmed by the executable instructions to: introduce a plurality of cells into microwells of the microwell array based on the first parameter and the second parameter. The processor can be programmed to: (e) if the first measurement is greater than a first predetermined threshold: adjust the first parameter based on the first measurement; and repeat steps (b)-(d). In some embodiments, to receive the first parameter used to deposit the first alignment droplet to the first desired location on the first alignment microwell array, the hardware processor is programmed by the executable instructions to: deposit the first alignment droplet to the desired location on the first alignment microwell array using the first parameter; and determine the path of the first alignment droplet in the first detection field using the first imaging sensor.

In some embodiments, the cell sorting component can comprise a nozzle. The nozzle can comprise an orifice. The cell sorting component can comprise a deflection plate.

DETAILED DESCRIPTION

Figure 1:
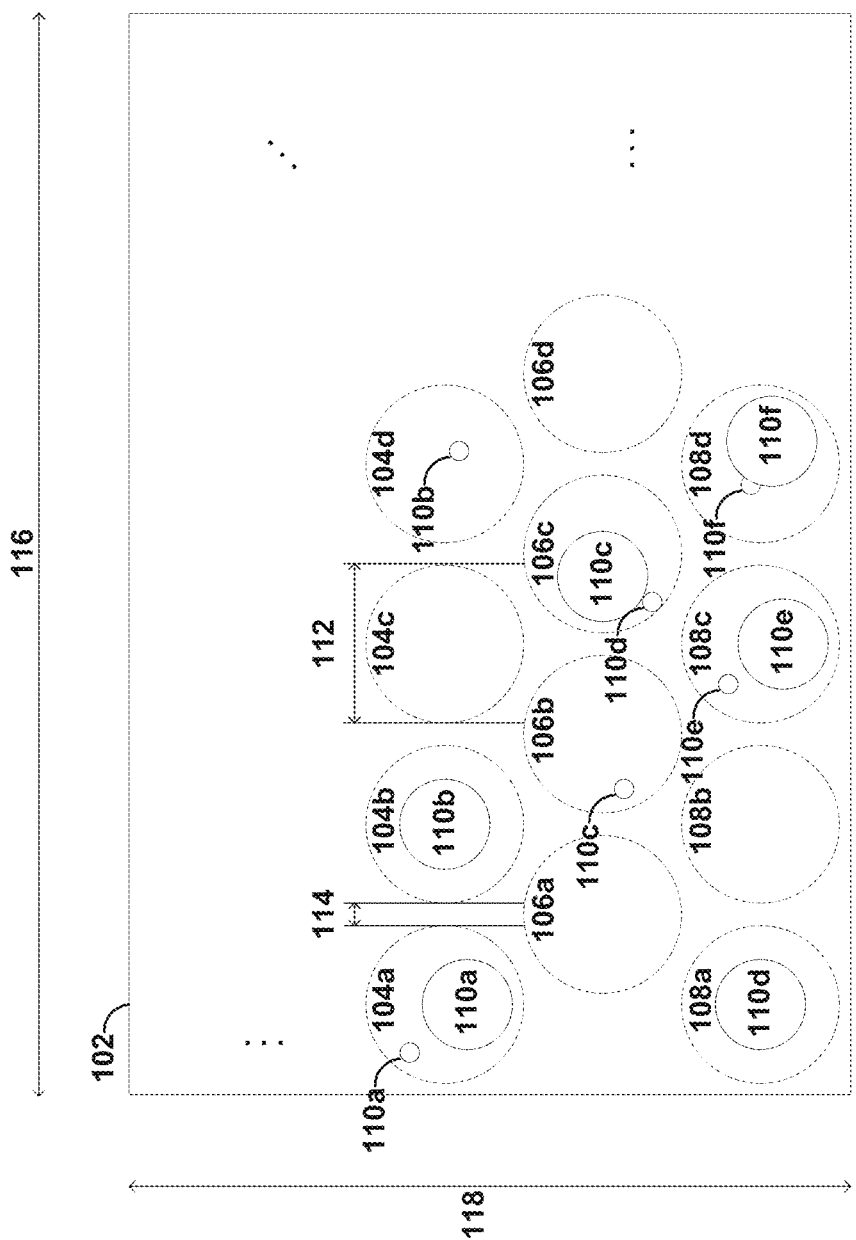
FIG. 1 is a non-limiting exemplary schematic illustration of a droplet array.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The subject systems, methods, and computer systems find use in a variety of different applications where it is desirable to automate adjustments of a flow stream of a flow cytometer to provide for fast, reliable systems for characterizing and sorting cells from a biological sample. Embodiments of the present disclosure find use where minimizing the amount of reliance on human input and adjustments to the system are desired, such as in research and high throughput laboratory testing. The present disclosure also finds use where it is desirable to provide a flow cytometer with improved cell sorting accuracy, enhanced particle collection, systems which provide alerts regarding component malfunction (e.g., clogged flow cell nozzle), reduced energy consumption, particle charging efficiency, more accurate particle charging and enhanced particle deflection during cell sorting. In embodiments, the present disclosure reduces the need for user input or manual adjustment during sample analysis with a flow cytometer. In certain embodiments, the subject systems provide fully automated protocols so that adjustments to a flow cytometer during use require little, if any human input.

The present disclosure also finds use in applications where cells prepared from a biological sample may be desired for research, laboratory testing or for use in therapy. In some embodiments, the subject methods and devices may facilitate the obtaining individual cells prepared from a target fluidic or tissue biological sample. For example, the subject methods and systems facilitate obtaining cells from fluidic or tissue samples to be used as a research or diagnostic specimen for diseases such as cancer. Likewise, the subject methods and systems facilitate obtaining cells from fluidic or tissue samples to be used in therapy. Methods and devices of the present disclosure allow for separating and collecting cells from a biological sample (e.g., organ, tissue, tissue fragment, fluid) with enhanced efficiency and low cost as compared to traditional flow cytometry systems.

The systems and methods of the present disclosure can be employed in any convenient flow cytometer system. Suitable flow cytometer systems and methods for analyzing samples include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem.* January; 49(pt 1):17-28; Linden, et. al., *Semin Throm Hemost.* 2004 Oct. 30(5):502-11; Alison, et al. *J Pathol,* 2010 December; 222(4):335-344; and Herbig, et al. (2007) *Crit Rev Ther Drug Carrier Syst.* 24(3):203-255; the disclosures of which are incorporated herein by reference. In certain instances, flow cytometry systems of interest include BD Biosciences FACSCanto™ flow cytometer, BD Biosciences FACSVantage™, BD Biosciences FACSort™, BD Biosciences FACSCount™, BD Biosciences FACScan™, and BD Biosciences FACSCalibur™ systems, a BD Biosciences Influx™ cell sorter, BD Biosciences Jazz™ cell sorter and BD Biosciences Aria™ cell sorter or the like.

In certain embodiments, the subject systems are flow cytometer systems which incorporate one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300;

8,233,146; 8,753,573; 8,975,595; 9,092,034; 9,095,494 and 9,097,640; the disclosures of which are herein incorporated by reference.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N Y 1989). For purposes of the present disclosure, the following terms are defined below.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "solid support" can refer to a discrete solid or a semi-solid surface to which a plurality of oligonucleotides, for example stochastic barcodes, can be attached. A solid support can encompass any type of solid, porous, or hollow sphere, ball, bearing, cylinder, or other similar configuration composed of plastic, ceramic, metal, or polymeric material (e.g., hydrogel) onto which a nucleic acid can be immobilized (e.g., covalently or non-covalently). A solid support can comprise a discrete particle that can be spherical (e.g., microspheres) or have a non-spherical or irregular shape, such as cubic, cuboid, pyramidal, cylindrical, conical, oblong, or disc-shaped, and the like. A solid support can be a "bead."

As used herein, the term "stochastic barcode" can refer to an oligonucleotide sequence comprising labels. A stochastic barcode can be an oligonucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "substrate" can refer to a continuous solid or semi-solid surface on which the methods of the disclosure may be performed. A substrate can refer to an array, a cartridge, a chip, a device, and a slide, for example.

Disclosed herein are methods, compositions and systems for producing high density arrays, including but not limited to droplet arrays, bead arrays and cellular arrays, as well as the high density arrays produced by the methods, compositions and systems disclosed herein. In some embodiments, production of high density arrays can utilize methods for aligning one or more alignment microwell arrays, wherein the methods can utilize two imaging sensors that are approximately orthogonal to each other.

Droplet Array

Disclosed herein are methods for producing droplet arrays. In some embodiments, the methods can comprise introducing a plurality of droplets into microwells of a microwell array to produce a droplet array. In some embodiments, a droplet can comprise, or can be, a small drop of liquid, a water-oil droplet, or any combination thereof. The droplet can comprises, for example, a single cell, two or more cells, one or more solid support, one or more synthetic particles, one or more proteins, one or more nucleic acids, one or more lipids, one or more oligosaccharides, one or more enzymes, one or more small molecules, or any combination thereof. For example, the plurality of droplets can be, or can comprise, a plurality of drops of liquid comprising cells, a plurality of drops of liquid comprising solid supports, or a plurality of drops of liquid comprising synthetic particles, or any combination thereof. One or more of the plurality of droplets can comprise, for example, a reagent. The droplet array can be, for example, a droplet array, a bead array, or a cellular array. FIG. 1 schematically illustrates a non-limiting exemplary microwell array 102. The microwell array 102 can comprise a plurality of microwells, including microwells 104a-104a d, 106a-106d, and 108a-108d. The density of the microwell array can vary. In some embodiments, the density of the microwell array can be 500 or more microwells per inch. In some embodiments, 25% or more of the microwells of the microwell array can comprise a single droplet, for example a single cell or a synthetic particle. In some embodiments, 30%, 35%, 40%, 45%, 50%, 55%, 60%, 65%, 70%, 75%, 80%, 85%, 90%, or more of the microwells of the microwell array comprise a single droplet, for example, a single cell or a synthetic particle. In FIG. 1, six wells, wells 104a, 104d, 106b, 106c, 108e, and 108d each comprises a single droplet, for example a single cell, 110a, 110b, 110c, 110d, 110e, and 110f respectively.

In some embodiments, the methods disclosed herein can be used to produce a cellular array. In some embodiments, introducing the plurality of droplets into the microwells of the microwell array to produce the droplet array can comprise introducing a plurality of cells in a sample into the microwells of the microwell array to produce a cellular array. A single droplet can comprise a single cell, and the droplet array can be the cellular array. In some embodiments, the methods can comprise providing the sample, wherein the sample comprises the plurality of cells. In some embodiments, the methods can comprise: providing a sample comprising a plurality of cells; and introducing the plurality of cells in the sample into microwells of a microwell array to produce the cellular array.

In some embodiments, the methods disclosed herein can be used to produce a synthetic particle array. In some embodiments, introducing the plurality of droplets into the microwells of the microwell array to produce the droplet array can comprise introducing a plurality of synthetic particles into the microwells of the microwell array to produce a synthetic particle array. A single droplet can comprise a synthetic particle, and the droplet array can be the synthetic particle array. In some embodiments, the methods can comprise: providing a plurality of synthetic particles; and introducing the plurality of synthetic particles into microwells of a microwell array to produce the synthetic particle array.

In some embodiments, the methods can comprise introducing a plurality of cells of interest in a cell sample into microwells of a microwell array at a plurality of desired locations, for example a first plurality of desired microwells. Introducing the plurality of cells of interest into the microwells of the microwell array at a plurality of desired locations can comprise flow cytometrically sorting the cells of interest from cells not of interest in the cell sample. In some embodiments, each of the cells of interest can be introduced into a microwell at its respective desired location. In some embodiments, the cells of interest and the cells not of interest in the cell sample can be sorted based on cell surface markers on the cells of interest and the cells not of interest in the cell sample.

The cell sample type can vary. In some embodiments, the cell sample can be, or can comprise, a clinical sample, a biological sample, an environmental sample, or any combination thereof. For example, the cell sample can include one or more of a biological fluid, tissue, and cell from a patient. For example, the cell sample can be, or can comprise, blood, urine, cerebrospinal fluid, pleural fluid, amniotic fluid, semen, saliva, bone marrow, a biopsy sample, or any combination thereof. For example, the cell sample can be, or can comprise, a mixed cancer cell sample.

As used herein, the term "cells of interest" can refer to cells being studied. The cells of interest can vary. In some embodiments, the cells of interest can have desired properties. For example, the cells of interest can have surface markers of interest or can have high expression of a surface marker. In some embodiments, the cells of interest can express a malignant phenotype. In some embodiments, the cells of interest can be, or can comprise, tumor cells, such as tumor cells which have been shed from tumor into blood or other bodily fluids or bone marrow; benign tumor cells; cancer cells; cancer cells in peripheral blood; thyroid cancer cells; breast cancer cells; circulating tumor cells ("CTCs"); leukemia cells; cancer stem cells; cells at cell cycle phases of desire (G0/G1, S, G2); sperms bearing X and Y chromosomes; stem cells; fetal or adult stem cells; multipotent stem cells; blood cells; nucleated red blood cells ("NRBC") in Thalassemia patients; fetal cells, such as fetal cells in maternal peripheral blood; fetal nucleated red blood cells ("FNRBC") in the maternal circulation; and cells characterized by CD71, CD8, CD34, or CD133; or any combination thereof. In some embodiments, the cells of interest can be, or can comprise, circulating endothelial cells; cells infected with a virus, such as cells infected by HIV, cells transfected with a gene of interest; and aberrant subtypes of T-cells or B-cells present in the peripheral blood of subjects afflicted with autoimmune or autoreactive disorders; activated lymphocytes; antigen presenting cells such as monocytes and dendritic cells; pathogenic or parasitic organisms, cells containing intracellular parasites; cells or microorganisms in dilute fluids like urine; or any combination thereof.

The cells of interest can be, or can comprise, cell lines. Non-limiting examples of cell lines include: Jurkat cells, a T-leukemia cell line; SKBR3, an adenocarcinoma derived breast cancer cell line known for overexpression of Her2/neu; T47D, a ductal carcinoma derived breast cancer cell line that demonstrates low to intermediate Her2/neu expression; HeLa; or any combination thereof.

The abundance of the cells of interest in the cell sample can vary. In some embodiments, the cells of interest in the cell sample can be, or be about, 0.0001%, 0.0005%, 0.001%, 0.005%, 0.01%, 0.1%, 0.5%, 1%, 10%, or a number or a range between any two of these values, of total number of cells in the cell sample. In some embodiments, the cells of interest in the cell sample can be at least, or at most, 0.0001%, 0.0005%, 0.001%, 0.005%, 0.01%, 0.1%, 0.5%, 1%, or 10% of total number of cells in the cell sample. In some embodiments, the cell sample can have, or have about, 1, 2, 3, 4, 5, 6, 7, 8, 9, 10, 15, 20, 25, 50, 100, 250, 500, 1000, or a number or a range between any two of these values, of the cells of interest per milliliter of the cell sample. In some embodiments, the cell sample have at most 1, 2, 3, 4, 5, 6, 7, 8, 9, 10, 15, 20, 25, 50, 100, 250, 500, or 1000 of the cells of interest per milliliter of the cell sample.

The size of the cells of interest can vary. In some embodiments, the diameter of the cells of interest can be, or be about, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 micrometers, or a number or a range between any two of these values. In some embodiments, the diameter of the cells of interest can be at least, or at most, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 micrometers.

In some embodiments, the methods can comprise introducing a first plurality of cells of interest and a second plurality of cells of interest in the cell sample into microwells of a microwell array at a plurality of desired locations. The plurality of desired locations can be different for the first plurality of cells of interest and the second plurality of cells of interest. For example, a first plurality of desired microwells can be desired locations for the first plurality of cells of interest. For example, second plurality of desired microwells can be desired locations for the second plurality of cells of interest. Introducing the first plurality of cells of interest and the second plurality of cells of interest in the cell sample into the microwells of the microwell array at the plurality of desired locations can comprise flow cytometrically sorting the first plurality of cells of interest and the second plurality of cells of interest in the cell sample. In some embodiments, the first plurality of cells of interest and the second plurality of cells of interest in the cell sample can be sorted based on cell surface markers on the first plurality of cells of interest and the second plurality of cells of interest in the cell sample.

In some embodiments, the methods can comprise introducing a plurality of droplets, for example a plurality of second droplets, into the microwells of a microwell array, for example the first droplet array or the cellular array, to produce another droplet array, for example a second droplet array. For example, the methods can comprise introducing a plurality of second droplets into the microwells of a microwell array before the plurality of first droplets are introduced into the microwells of the microwell array. For example, the methods can comprise introducing a plurality of second droplets into the microwells of a microwell array after the plurality of first droplets are introduced into the microwells of the microwell array. In some embodiments, 25% or more of the microwells of the droplet array can comprise a single first droplet, for example a single cell, and a single second droplet, for example a synthetic particle or a reagent. In FIG. 1, six wells, wells 104*a*, 104*b*, 106*c*, 108*a*, 108*c*, and 108*d* each comprises a single second droplet, for example a single synthetic bead 110*a*, 110*b*, 110*c*, 110*d*, 110*e*, or 110*f* respectively. Four wells, wells 104*a*, 106*c*, 108*c*, and 108*d*, each comprises a single first droplet and a single second droplet.

In some embodiments, the methods can comprise introducing a reagent into one or more microwells of a microwell array. For example, the methods can comprise introducing a reagent into one or more microwells of the microwell array before the plurality of cells are introduced into the microwells of the microwell array. For example, the methods can comprise introducing a reagent into one or more microwells of the microwell array after the plurality of cells are introduced into the microwells of the microwell array. In some embodiments, 25% or more of the microwells of the microwell array can comprise a single cell and the reagent.

In some embodiments, 30%, 35%, 40%, 45%, 50%, 55%, 60%, 65%, 70%, 75%, 80%, 85%, 90%, or more of the microwells of the microwell array can comprise a single cell and the reagent. In some embodiments, introducing the reagent into one or more microwells of the microwell array can comprise introducing the reagent into the one or more microwells of the microwell array at a plurality of desired locations. In some embodiments, the reagent can comprise one or more synthetic particles.

In some embodiments, the methods can comprise introducing synthetic particles into one or more microwells of a microwell array. For example, the methods can comprise introducing synthetic particles into one or more microwells of a microwell array before the plurality of cells are introduced into the microwells of the microwell array. For example, the methods can comprise introducing synthetic particles into one or more microwells of a microwell array after the plurality of cells are introduced into the microwells of the microwell array. In some embodiments, 25% or more of the microwells of the microwell array can comprise a single cell and a synthetic particle. In some embodiments, 30%, 35%, 40%, 45%, 50%, 55%, 60%, 65%, 70%, 75%, 80%, 85%, 90%, or more of the microwells of the microwell array can comprise a single cell and a synthetic particle.

In some embodiments, the methods can comprise introducing a plurality of synthetic particles of interest, for examples beads, in a synthetic particle sample into microwells of the microwell array at a plurality of desired locations, for example a second plurality of desired microwells. In some embodiments, the plurality of synthetic particles of interest are introduced into the microwells of the microwell array at the plurality of desired locations after a plurality of cells of interest are introduced into the microwells of the microwell array at a plurality of first desired locations. In some embodiments, the synthetic particles of interest can comprise a reagent. In some embodiments, introducing the plurality of synthetic particles of interest into the microwells of the microwell array at the plurality of desired locations can comprise flow cytometrically sorting the synthetic particles of interest from synthetic particles not of interest in the synthetic particle sample. In some embodiments, the synthetic particles of interest and the synthetic particles not of interest in the synthetic particle sample can be sorted based on whether they contain a reagent.

In some embodiments, the methods can comprise introducing a first plurality of synthetic particles and a second plurality of synthetic particles in a synthetic particle sample into microwells of the microwell array at a plurality of desired locations. The plurality of desired locations for the first plurality of synthetic particles can be a first plurality of desired locations. The plurality of desired locations for the second plurality of synthetic particles can be a second plurality of desired locations. In some embodiments, the first plurality of synthetic particles and the second plurality of synthetic particles are introduced into the microwells of the microwell array at the plurality of desired locations after one or more pluralities of cells of interest are introduced into the microwells of the microwell array. In some embodiments, the first plurality of synthetic particles can comprise a first reagent. In some embodiments, the second plurality of synthetic particles can comprise a second reagent. In some embodiments, introducing the first plurality of synthetic particles and the second plurality of synthetic particles into the microwells of the microwell array at the plurality of desired locations can comprise flow cytometrically sorting the first plurality of synthetic particles and the second plurality of synthetic particles. In some embodiments, the first plurality of synthetic particles and the second plurality of synthetic particles in the synthetic particle sample can be sorted based on the reagent they contain, for example the first reagent and the second reagent.

The synthetic particles in the synthetic particle sample can vary. In some embodiments, the synthetic particles in the synthetic particle sample can be identical. In some embodiments, one of the synthetic particles in the synthetic particle sample can differ from the others of the synthetic particles in the synthetic particle sample. For example, the percentage of synthetic particles in the synthetic particle sample that are the identical can be, or be about, 1%, 2%, 3%, 4%, 5%, 6%, 7%, 8%, 9%, 10%, 20%, 30%, 40%, 50%, 60%, 70%, 80%, 90%, 99.9%, 100%, or a number or a range between any two of these values. For example, the percentage of synthetic particles in the synthetic particle sample that are the same can be at least, or at most, 1%, 2%, 3%, 4%, 5%, 6%, 7%, 8%, 9%, 10%, 20%, 30%, 40%, 50%, 60%, 70%, 80%, 90%, 99.9%, or 100%. In some embodiments, introducing synthetic particles into the one or more microwells of the microwell array can comprise introducing the synthetic particles into microwells of the microwell array at a plurality of desired locations, for example a plurality of second desired locations.

Synthetic Particles

Methods, compositions and systems described herein can be used to deposit synthetic particles to produce high density arrays of the synthetic particles. In some embodiments, the synthetic particles can be, or can comprise, beads, for example magnetic or polymeric beads attached with oligonucleotide barcodes. In some embodiments, a synthetic particle can be, or can comprise, a bead attached with a plurality of oligonucleotide barcodes. The plurality of oligonucleotide barcodes can be, for example, a plurality of stochastic barcodes. A stochastic barcode is a polynucleotide sequence that may be used to stochastically label (e.g., barcode, tag) a target. A stochastic barcode can comprise one or more labels. Non-limiting exemplary labels include a universal label, a chromosome label, a cell label, a molecular label, a sample label, a plate label, a spatial label, and a pre-spatial label. The plurality of oligonucleotide barcodes on a given synthetic particles can be the same or different. In some embodiments, one of the plurality of oligonucleotide barcode differs from at least one other of the plurality of oligonucleotide barcodes. In some embodiments, the plurality of oligonucleotides on a given synthetic particles can have the same cell label sequence. In some embodiments, at least two of the plurality of oligonucleotides on a given synthetic particles can have different molecular label sequences.

Non-limiting examples of the beads include silica beads, silica-like beads, silica gel beads, controlled pore glass beads, magnetic beads, Sephadex/Sepharose beads, cellulose beads, polystyrene beads, or any combination thereof, streptavidin beads, agarose beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, anti-biotin microbeads, anti-fluorochrome microbeads, BcMag™ Carboxyl-Terminated Magnetic Beads, and any combination thereof.

Beads can comprise a variety of materials including, but not limited to, paramagnetic materials (e.g. magnesium, molybdenum, lithium, and tantalum), superparamagnetic materials (e.g. ferrite ($Fe_3O_4$; magnetite) nanoparticles), ferromagnetic materials (e.g. iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, and any combination thereof. In some embodiments, the bead (e.g., the bead to which the stochastic labels are attached) is a hydrogel bead. In some embodiments, the bead comprises hydrogel.

In some embodiments, the bead can be a polymeric bead, for example a deformable bead or a gel bead, functionalized with stochastic barcodes (such as gel beads from 10× Genomics (San Francisco, Calif.). In some implementation, a gel bead can comprise a polymer based gels. Gel beads can be generated, for example, by encapsulating one or more polymeric precursors into droplets. Upon exposure of the polymeric precursors to an accelerator (e.g., tetramethylethylenediamine (TEMED)), a gel bead may be generated.

In some embodiments, the polymeric bead can dissolve, melt, or degrade, for example, under a desired condition. The desired condition can include an environmental condition. The desired condition may result in the polymeric bead dissolving, melting, or degrading in a controlled manner. A gel bead may dissolve, melt, or degrade due to a chemical stimulus, a physical stimulus, a biological stimulus, a thermal stimulus, a magnetic stimulus, an electric stimulus, a light stimulus, or any combination thereof.

Analytes and/or reagents, such as oligonucleotide barcodes, for example, may be coupled/immobilized to the interior surface of a gel bead (e.g., the interior accessible via diffusion of an oligonucleotide barcode and/or materials used to generate an oligonucleotide barcode) and/or the outer surface of a gel bead or any other microcapsule described herein. Coupling/immobilization may be via any form of chemical bonding (e.g., covalent bond, ionic bond) or physical phenomena (e.g., Van der Waals forces, dipole-dipole interactions, etc.). In some cases, coupling/immobilization of a reagent to a gel bead or any other microcapsule described herein may be reversible, such as, for example, via a labile moiety (e.g., via a chemical cross-linker, including chemical cross-linkers described herein). Upon application of a stimulus, the labile moiety may be cleaved and the immobilized reagent set free. In some cases, the labile moiety is a disulfide bond. For example, in the case where an oligonucleotide barcode is immobilized to a gel bead via a disulfide bond, exposure of the disulfide bond to a reducing agent can cleave the disulfide bond and free the oligonucleotide barcode from the bead. The labile moiety may be included as part of a gel bead or microcapsule, as part of a chemical linker that links a reagent or analyte to a gel bead or microcapsule, and/or as part of a reagent or analyte.

In some embodiments, a gel bead can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption or degradation of the beads. Examples of these chemical changes may include, but are not limited to pH-mediated changes to the bead wall, disintegration of the bead wall via chemical cleavage of crosslink bonds, triggered depolymerization of the bead wall, and bead wall switching reactions. Bulk changes may also be used to trigger disruption of the beads.

Bulk or physical changes to the microcapsule through various stimuli also offer many advantages in designing capsules to release reagents. Bulk or physical changes occur on a macroscopic scale, in which bead rupture is the result of mechano-physical forces induced by a stimulus. These processes may include, but are not limited to pressure induced rupture, bead wall melting, or changes in the porosity of the bead wall.

Biological stimuli may also be used to trigger disruption or degradation of beads. Generally, biological triggers resemble chemical triggers, but many examples use biomolecules, or molecules commonly found in living systems such as enzymes, peptides, saccharides, fatty acids, nucleic acids and the like. For example, beads may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the beads are released. In other cases, the proteases may be heat-activated. In another example, beads comprise a shell wall comprising cellulose. Addition of the hydrolytic enzyme chitosan serves as biologic trigger for cleavage of cellulosic bonds, depolymerization of the shell wall, and release of its inner contents.

The beads may also be induced to release their contents upon the application of a thermal stimulus. A change in temperature can cause a variety changes to the beads. A change in heat may cause melting of a bead such that the bead wall disintegrates. In other cases, the heat may increase the internal pressure of the inner components of the bead such that the bead ruptures or explodes. In still other cases, the heat may transform the bead into a shrunken dehydrated state. The heat may also act upon heat-sensitive polymers within the wall of a bead to cause disruption of the bead.

Inclusion of magnetic nanoparticles to the bead wall of microcapsules may allow triggered rupture of the beads as well as guide the beads in an array. A device of this disclosure may comprise magnetic beads for either purpose. In one example, incorporation of $Fe_3O_4$ nanoparticles into polyelectrolyte containing beads triggers rupture in the presence of an oscillating magnetic field stimulus.

A bead may also be disrupted or degraded as the result of electrical stimulation. Similar to magnetic particles described in the previous section, electrically sensitive beads can allow for both triggered rupture of the beads as well as other functions such as alignment in an electric field, electrical conductivity or redox reactions. In one example, beads containing electrically sensitive material are aligned in an electric field such that release of inner reagents can be controlled. In other examples, electrical fields may induce redox reactions within the bead wall itself that may increase porosity.

A light stimulus may also be used to disrupt the beads. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the bead wall. In yet another example, photo switchable materials such as azobenzene groups may be incorporated in the bead wall. Upon the application of UV or visible light, chemicals such as these undergo a reversible cis-to-trans isomerization upon absorption of photons. In this aspect, incorporation of photon switches result in a bead wall that may disintegrate or become more porous upon the application of a light trigger.

Some embodiments disclosed herein include one or more particles (for example beads). Each of the particles can comprise a plurality of oligonucleotides (e.g., stochastic barcodes). Each of the plurality of oligonucleotides can comprise a molecular label sequence, a cell label sequence, and a target-binding region (e.g., an oligo dT sequence, a gene-specific sequence, a random multimer, or a combination thereof). The cell label sequence of each of the plurality of oligonucleotides can be the same. The cell label sequences of oligonucleotides on different particles can be different such that the oligonucleotides on different particles can be identified. The number of different cell label sequences can be different in different implementations. In some embodiments, the number of cell label sequences can be, or about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell label sequences can be at least, or at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles include oligonucleotides with the same cell sequence. In some embodiment, the plurality of particles that include oligonucleotides with the same cell sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10% or more. In some embodiments, none of the plurality of the particles has the same cell label sequence.

The plurality of oligonucleotides on each particle can comprise different molecular label sequences. In some embodiments, the number of molecular label sequences can be, or about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of molecular label sequences can be at least, or at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. For example, at least 100 of the plurality of oligonucleotides comprise different molecular label sequences. As another example example, in a single particle, at least 100, 500, 1000, 5000, 10000, 15000, 20000, 50000, a number or a range between any two of these values, or more of the plurality of oligonucleotides comprise different molecular label sequences. Some embodiments provide a plurality of the particles comprising stochastic barcodes. In some embodiments, the ratio of an occurrence (or a copy or a number) of a target to be labeled and the different molecular label sequences can be at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or more. In some embodiments, each of the plurality of oligonucleotides further comprises a sample label, a universal label, or both. The particle can be, for example, a nanoparticle or microparticle.

The size of the beads can vary. For example, the diameter of the bead can range from 0.1 micrometer to 50 micrometer. In some embodiments, the diameters of beads can be, or be about, 0.1, 0.5, 1, 2, 3, 4, 5, 6, 7, 8, 9, 10, 20, 30, 40, 50 micrometer, or a number or a range between any two of these values. In some embodiments, the diameters of beads can be at least, or at most, 0.1, 0.5, 1, 2, 3, 4, 5, 6, 7, 8, 9, 10, 20, 30, 40, or 50 micrometer.

The diameters of the bead can be related to the diameter of the wells of the substrate. In some embodiments, the diameters of the bead can be, or be about, 10%, 20%, 30%, 40%, 50%, 60%, 70%, 80%, 90%, 100%, or a number or a range between any two of these values, longer or shorter than the diameter of the well. In some embodiments, the diameters of the bead can be at least, or at most, 10%, 20%, 30%, 40%, 50%, 60%, 70%, 80%, 90%, or 100%, longer or shorter than the diameter of the well. In some embodiments, the wells of the substrate are sized such that one or more of those wells can each only accommodate one bead. In some embodiments, all of the wells are sized such that each of the wells can each only accommodate one bead. In some embodiments, the percentage of the wells that are sized such that each of those wells can only accommodate one bead can be, or be about, 10%, 20%, 30%, 40%, 50%, 60%, 70%, 80%, 90%, 95%, 99%, 99.9%, 100%, or a number or a range between any two of these values. In some embodiments, the percentage of the wells that are sized such that each of those wells can only accommodate one bead can be at least, or at most, 10%, 20%, 30%, 40%, 50%, 60%, 70%, 80%, 90%, 95%, 99%, 99.9%, 100%, or a number or a range between any two of these values.

The diameter of the beads can be related to the diameter of a cell (e.g., a single cell entrapped by a well of the substrate). In some embodiments, the diameters of the beads can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell. In some embodiments, the diameter of the beads can be at least, or at most, 10%, 20%, 30%, 40%, 50%, 60%, 70%, 80%, 90%, 100%, 150%, 200%, 250%, or 300%, longer or shorter than the diameter of the cell.

A bead can be attached to and/or embedded in a substrate. A bead can be attached to and/or embedded in a gel, hydrogel, polymer and/or matrix. The spatial position of a bead within a substrate (e.g., gel, matrix, scaffold, or polymer) can be identified using the spatial label present on the stochastic barcode on the bead which can serve as a location address.

A bead can be associated with (e.g. impregnated with) quantum dots or fluorescent dyes to make it fluorescent in one fluorescence optical channel or multiple optical channels. A bead can be associated with iron oxide or chromium oxide to make it paramagnetic or ferromagnetic. Beads can be identifiable. For example, a bead can be imaged using a camera. A bead can have a detectable code associated with the bead. For example, a bead can comprise a stochastic barcode. A bead can change size, for example due to swelling in an organic or inorganic solution. A bead can be hydrophobic. A bead can be hydrophilic. A bead can be biocompatible.

A solid support (e.g., bead) can be visualized. The solid support can comprise a visualizing tag (e.g., fluorescent dye). A solid support (e.g., bead) can be etched with an identifier (e.g., a number). The identifier can be visualized through imaging the beads.

A solid support can refer to an insoluble, semi-soluble, or insoluble material. A solid support can be referred to as "functionalized" when it includes a linker, a scaffold, a building block, or other reactive moiety attached thereto, whereas a solid support can be "nonfunctionalized" when it lack such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. A solid support can take the form of resins, gels, microspheres, or other geometric configurations. A solid support can comprise silica chips, synthetic particles, nanoparticles, plates, and arrays. Solid supports can include beads (e.g., silica gel, controlled pore glass, magnetic beads, Dynabeads®, Wang resin; Merrifield resin, Sephadex/Sepharose beads, cellulose beads, polystyrene beads etc.), capillaries, flat supports such as glass fiber filters, glass surfaces, metal surfaces (steel, gold silver, aluminum, silicon and copper), glass supports, plastic supports, silicon supports, chips, filters, membranes, microwell plates, slides, or the like, plastic materials including multi-well plates or membranes (e.g., formed of polyethylene, polypropylene, polyamide, polyvinylidene difluoride), wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

In some embodiments stochastic barcodes of the disclosure can be attached to a polymer matrix (e.g., gel, hydrogel). The polymer matrix can be able to permeate intracellular space (e.g., around organelles). The polymer matrix can able to be pumped throughout the circulatory system.

Array Occupancy

The percentage of the microwells of a droplet array, for example the first droplet array, the cellular array, or the synthetic particle array, comprising or consisting of a single droplet can vary. The percentage can vary, for example ranging from 10% to 100%. In some embodiments, the percentage of the microwells of the droplet array comprising, or consisting of, a single droplet can be, or be about, 10%, 20%, 30%, 40%, 50%, 60%, 70%, 80%, 90%, 99%, 99.9%, 100%, or a number or a range between any two of these values. In some embodiments, the percentage of the microwells of the droplet array comprising, or consisting of, a single droplet can be at least, or at most, 10%, 20%, 30%, 40%, 50%, 60%, 70%, 80%, 90%, 99%, 99.9%, or 100%. In some embodiments, 25% or more of the microwells of the droplet array comprise a single droplet, for example, a single cell.

The percentage of the microwells of a droplet array, for example the second droplet array, the cellular array, or the synthetic particle array, comprising or consisting of a single droplet, for example a single second droplet, can vary. The percentage can vary, for example ranging from 10% to 100%. In some embodiments, the percentage of the microwells of the droplet array comprising or consisting of a single second droplet can be, or be about, 10%, 20%, 30%, 40%, 50%, 60%, 70%, 80%, 90%, 99%, 99.9%, 100%, or a number or a range between any two of these values. In some embodiments, the percentage of the microwells of the droplet array comprising or consisting of a single second droplet can be at least, or at most, 10%, 20%, 30%, 40%, 50%, 60%, 70%, 80%, 90%, 99%, 99.9%, or 100%. In some embodiments, 25% of the microwells of the droplet array can comprise a single second droplet, for example, a synthetic particle.

The percentage of the microwells of a droplet array, for example the second droplet array, the cellular array, or the synthetic particle array, comprising or consisting of a single first droplet, for example a single cell, and a single second droplet comprising, for example a synthetic particle or a reagent, can vary. The percentage can range from 10% to 100%. In some embodiments, the percentage of the microwells of the droplet array comprising or consisting of a single first droplet and a single second droplet can be, or be about, 10%, 20%, 30%, 40%, 50%, 60%, 70%, 80%, 90%, 99%, 99.9%, 100%, or a number or a range between any two of these values. In some embodiments, the percentage of the microwells of the droplet array comprising or consisting of a single first droplet and a single second droplet can be at least, or at most, 10%, 20%, 30%, 40%, 50%, 60%, 70%, 80%, 90%, 99%, 99.9%, or 100%. In some embodiments, 25% or more of the microwells of the droplet array can comprise a single first droplet, for example a single cell, and a single second droplet, for example a synthetic particle or a reagent.

Substrate and Microwell Array

A substrate can comprise a plurality of microwells, including microwells 104a-d, 106a-d, and 108a-d shown in FIG. 1. In some embodiments, a substrate can be a microwell array 102 comprising a plurality of microwells. In some embodiments, a microwell, for example the microwell 104a-d, 106a-d, or 108a-d, can comprise a small reaction chamber of defined volume. In some embodiments, a microwell can entrap one or more droplets of, for example, a single cell or a synthetic particle. In some embodiments, a microwell can entrap one or more cells. In some embodiments, a microwell can entrap only one single cell. In some embodiments, a microwell can entrap one or more solid supports, for example synthetic particles such as beads. In some embodiments, a microwell can entrap only one solid support. In some embodiments, a microwell can entrap a single cell and a single solid support.

Microwell Shapes

Microwells of a microwell array, for example the microwell array 102 shown in FIG. 1, can be fabricated in a variety of shapes. Non-limiting exemplary well geometries can include cylindrical, conical, hemispherical, rectangular, or polyhedral (e.g., three dimensional geometries comprised of several planar faces, for example, hexagonal columns, octagonal columns, inverted triangular pyramids, inverted square pyramids, inverted pentagonal pyramids, inverted hexagonal pyramids, or inverted truncated pyramids). The microwells can comprise a shape that combines two or more of these geometries. For example, a microwell can be partly cylindrical, with the remainder having the shape of an inverted cone. A microwell can include two side-by-side cylinders, one of larger diameter (e.g. that corresponds roughly to the diameter of the beads) than the other (e.g. that corresponds roughly to the diameter of the cells), that are connected by a vertical channel (that is, parallel to the cylinder axes) that extends the full length (depth) of the cylinders. The location of the opening of the microwell can vary. For example, the opening of the microwell can be at the upper surface of the substrate. For example, the opening of the microwell can be at the lower surface of the substrate.

The shape of the close end, for example the bottom, of the microwell can vary. For example, the closed end of the microwell can be flat. For example, the closed end of the microwell can have a curved surface (e.g., convex or concave). The shape and/or size of the microwell can be determined based on the types of cells or solid supports to be trapped within the microwells.

Microwell Sizes

Microwells of a microwell array, for example the microwell array 102 shown in FIG. 1, can be fabricated in a variety of sizes. Microwell size can be characterized, for example, in terms of the diameter 112 and/or the depth of the microwells. As shown in FIG. 1, the diameter 112 of the microwell can refer to the largest circle that can be inscribed within the planar cross-section of the microwell geometry. The diameter 112 of the microwells can, in some embodiments, range from about 1-fold to about 10-folds the diameter of the cells or solid supports to be trapped within the microwells. In some embodiments, the microwell diameter 112 can be, or be about, 1-fold, 1.5-fold, 2-folds, 3-folds, 4-folds, 5-folds, 6-folds, 7-folds, 8-folds, 9-files, 10-folds, or a number or a range between any two of these values, the diameter of the cells or the solid supports to be trapped within the microwells. In some embodiments, the microwell diameter 112 can be at least, or at most, 1-fold, 1.5-fold, 2-folds, 3-folds, 4-folds, 5-folds, 6-folds, 7-folds, 8-folds, 9-files, 10-folds the diameter of the cells or the solid supports to be trapped within the microwells. In some embodiments, the microwell diameter 112 can be about 2.5-folds the diameter of the cells or solid supports to be trapped within the microwells.

The diameter 112 of the microwells can be specified in terms of absolute dimensions. The diameter of the microwells can range from about 1 nanometer to about 1000 micrometers. In some embodiments, the microwell diameter 112 can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the microwell diameter 112 can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers. In some embodiments, the microwell diameter 112 can be, or be about, 1, 2, 3, 4, 5, 6, 7, 8, 9 10, 20, 30, 40, 50, 60, 70, 80, 90, 100, 200, 300, 400, 500, 600, 700, 800, 900, 1000 micrometers, or a number or a range between any two of these values. In some embodiments, the microwell diameter 112 can be at least, or at most 1, 2, 3, 4, 5, 6, 7, 8, 9, 10, 20, 30, 40, 50, 60, 70, 80, 90, 100, 200, 300, 400, 500, 600, 700, 800, 900, 1000 micrometers. In some embodiments, the microwell diameter can be about 30 micrometers.

The depth of the microwell can also vary, for example, to provide efficient trapping of droplets, for example cells and solid supports, or to provide efficient exchange of assay buffers and other reagents contained within the wells. The ratio of diameter to depth (i.e. aspect ratio) can be varied such that once a cell and/or a solid support settle inside a microwell, they will not be displaced by fluid motion above the microwell. In some embodiments, the depth of the microwell can be smaller than the diameter of the bead. For example, the depth of the microwell can be, or be about, 5%, 10%, 20%, 30%, 40%, 50%, 60%, 70%, 80%, 90%, 99%, 99.9%, 100%, or a number or a range between any two of these values, of the diameter of the bead. For example, the depth of the microwell can be at least, or at most, 5%, 10%, 20%, 30%, 40%, 50%, 60%, 70%, 80%, 90%, 99%, 99.9%, 100% of the diameter of the bead. In some embodiments, synthetic particles such as beads can protrude outside of the microwells.

The dimensions of the microwell can vary such that the microwell has sufficient space to accommodate a solid support and a cell of various sizes without being dislodged by fluid motion above the microwell. The depth of the microwells can range from about 1-fold to about 10-folds the diameter of the cells or solid supports to be trapped within the microwells. In some embodiments, the microwell depth can be, or be about, 1-fold, 1.5-fold, 2-folds, 3-folds, 4-folds, 5-folds, 6-folds, 7-folds, 8-folds, 9-files, 10-folds, or a number or a range between any two of these values, the diameter of the cells or solid supports to be trapped within the microwells. In some embodiments, the microwell depth can be at least, or at most, 1-fold, 1.5-fold, 2-folds, 3-folds, 4-folds, 5-folds, 6-folds, 7-folds, 8-folds, 9-files, or 10-folds the diameter of the cells or solid supports to be trapped within the microwells. In some embodiments, the microwell depth can be about 2.5-folds the diameter of the cells or solid supports to be trapped within the microwells.

The depth of the microwells can be specified in terms of absolute dimensions. For example, the depth of the microwells can range from about 1 nanometer to about 1000 micrometers. In some embodiments, the microwell depth can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the microwell depth can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers. In some embodiments, the microwell depth can be, or be about, 1, 2, 3, 4, 5, 6, 7, 8, 9 10, 20, 30, 40, 50, 60, 70, 80, 90, 100, 200, 300, 400, 500, 600, 700, 800, 900, 1000 micrometers, or a number or a range between any two of these values. In some embodiments, the microwell depth can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers. In some embodiments, the microwell depth can be about 30 micrometers.

The volumes of the microwells can vary, for example ranging from about 1 picoliter to about 1000 microliters. In some embodiments, the microwell volume can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, picoliters. In some embodiments, the microwell volume can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 picoliters. In some embodiments, the microwell volume can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, nanoliters. In some embodiments, the microwell volume can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 nanoliters. In some embodiments, the microwell volume can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, microliters. In some embodiments, the microwell volume can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000. In some embodiments, the microwell volume can be about 1 microliter.

The volumes of the microwells can be characterized in terms of the variation in volume from one microwell to another. The coefficient of variation (expressed as a percentage) for microwell volume can range from about 1% to about 100%. The coefficient of variation for microwell volume can be, or be about, 1%, 2%, 3%, 4%, 5%, 6%, 7%, 8%, 9%, 10%, 20%, 30%, 40%, 50%, 60%, 70%, 80%, 90%, 100%, or a number or a range between any two of these values. The coefficient of variation for microwell volume can be, at least or at most, 1%, 2%, 3%, 4%, 5%, 6%, 7%, 8%, 9%, 10%, 20%, 30%, 40%, 50%, 60%, 70%, 80%, 90%, or 100%. In some embodiments, the coefficient of variation of microwell volume can be about 2.5%.

The ratio of the volume of the microwells to the surface area of the beads (or to the surface area of a solid support to which stochastic barcode oligonucleotides can be attached) can vary, for example range from about 2.5 to about 1520 micrometers. In some embodiments, the ratio can be, or be about, 2.5, 5, 10, 100, 500, 750, 1000, 1520 micrometers, or a number or a range between any two of these values. In some embodiments, the ratio can be at least, or at most, 2.5, 5, 10, 100, 500, 750, 1000, or 1520 micrometers. In some embodiments, the ratio can be about 67.5 micrometers.

Microwell Arrangements

Microwells of a microwell array, for example the microwell array 102 shown in FIG. 1, can be arranged in a one dimensional, two dimensional, or three-dimensional array. A three dimensional array can be achieved, for example, by stacking a series of two or more two dimensional arrays, for example by stacking two or more substrates comprising microwell arrays.

The pattern and spacing between microwells can vary to optimize the efficiency of trapping a single cell and a single solid support (e.g., bead) in each well, as well as to maximize the number of wells per unit area of the array. The microwells can be distributed according to a variety of random or non-random patterns. For example, they can be distributed entirely randomly across the surface of the array substrate, or they can be arranged in a square grid, rectangular grid, hexagonal grid, or the like.

The center-to-center distance or the center-to-center spacing between wells can vary from about 1 micrometer to about 1000 micrometers. In some embodiments, the center-to-center distance between wells can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the center-to-center distance between wells can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 micrometers. In some embodiments, the center-to-center distance between wells can be about 4890 micrometers.

The distance or the spacing 114 between the edges of the microwells can vary from about 1 micrometer to about 1000 micrometers. In some embodiments, the distance between the edges of the wells can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the distance between the edges of the wells can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 micrometers. In some embodiments, the distance between the edges of the wells can be about 80 micrometers.

Microwell Density

A microwell array, for example the microwell array 102 shown in FIG. 1, can comprise microwells at varying densities, for example ranging from 100 microwells per inch$^2$ to 10000 microwells per inch$^2$. In some embodiments, the density of the microwell array can be, or be about, 100, 200, 300, 400, 500, 600, 700, 800, 900, 1000, 2000, 3000, 4000, 5000, 6000, 7000, 8000, 9000, 10000, 20000, 30000, 40000, 50000, or a number or a range between any two of these values, microwells per inch$^2$. In some embodiments, the density of the microwell array can be at least, or at most, 100, 200, 300, 400, 500, 600, 700, 800, 900, 1000, 2000, 3000, 4000, 5000, 6000, 7000, 8000, 9000, 10000, 20000, 30000, 40000, or 50000, microwells per inch$^2$. In some embodiments, the density of the microwell array can be, or be about, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values, microwells per cm$^2$. In some embodiments, the density of the microwell array can be at least, or at most, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000 microwells per cm$^2$.

The total number of wells in the microwell array can vary based on the pattern and the spacing of the wells and the overall dimensions of the array. The number of microwells in the array can vary, for example, ranging from about 96 to about 1000000. In some embodiments, the number of microwells in the microarray can be, or be about, 96, 384, 1536, 2000, 3000, 4000, 5000, 6000, 7000, 8000, 9000, 10000, 20000, 30000, 40000, 50000, 60000, 70000, 80000, 90000, 100000, or a number or a range between any two of these values. In some embodiments, the number of microwells in the microarray can be at least, or at most, 96, 384, 1536, 2000, 3000, 4000, 5000, 6000, 7000, 8000, 9000, 10000, 20000, 30000, 40000, 50000, 60000, 70000, 80000, 90000, or 100000. In some embodiments, the number of microwells in the microwell array can be about 96. In some embodiments, the number of microwells can be about 150000.

Microwell Array Surface Features

A microwell array, for example the microwell array 102 shown in FIG. 1, can comprise surface features between the microwells that are designed to help guide cells and solid supports into the wells and/or to prevent them from settling on the surfaces between wells. Non-limiting examples of suitable surface features include, but are not limited to, domed, ridged, or peaked surface features that encircle the wells or straddle the surface between wells.

Substrate Fabrication Techniques

A microwell, for example the microwell array 102 shown in FIG. 1, can be fabricated using any of a number of fabrication techniques. Non-limiting examples of fabrication methods that can be used include bulk micromachining techniques such as photolithography and wet chemical etching, plasma etching, or deep reactive ion etching; micromolding and micro-embossing; laser micromachining; 3D printing or other direct write fabrication processes using curable materials; and similar techniques.

Microwell arrays can be fabricated from a variety of substrate materials. The choice of material can depend on the choice of fabrication technique, and vice versa. Non-limiting examples of suitable materials include fused-silica, glass, polymers (e.g. agarose, gelatin, hydrogels, polydimethylsiloxane (PDMS) elastomer, polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, thiol-ene based resins, metals or metal films (e.g. aluminum, stainless steel, copper, nickel, chromium, and titanium), and the like. A hydrophilic material can be desirable for fabrication of the microwell arrays (e.g. to enhance wettability and minimize non-specific binding of cells and other biological material). Hydrophobic materials that can be treated or coated (e.g. by oxygen plasma treatment, or grafting of a polyethylene oxide surface layer) can also be used for fabrication of the microwell arrays. The use of porous, hydrophilic materials for the fabrication of the microwell array can be desirable in order to facilitate capillary wicking/venting of entrapped air bubbles in the device. The microwell array can be fabricated from a single material. The microwell array can comprise two or more different materials that have been bonded together or mechanically joined.

Substrate Shapes and Sizes

A microwell array, for example the microwell array 102 shown in FIG. 1, can be fabricated using substrates of a variety of shapes and sizes. For example, the shape (or footprint) of the substrate within which microwells are fabricated can be square, rectangular, circular, or irregular in shape. The size of a microwell array, for example the microwell array 102, can be characterized by its width 116, length 118, and depth.

The width 116 of the well array 102 can vary, ranging from 0.1 inch to 10 inches. In some embodiments, the width 116 of the well array 102 can be, or be about, 0.1, 0.2, 0.3, 0.4, 05, 0.6, 0.7, 0.8, 0.9, 1, 2, 3, 4, 5, 6, 7, 8, 9, 10 inches, or a number or a range between any two of these values. In some embodiments, the width 116 of the well array 102 can be at least, or at most, 0.1, 0.2, 0.3, 0.4, 05, 0.6, 0.7, 0.8, 0.9, 1, 2, 3, 4, 5, 6, 7, 8, 9, or 10 inches. The width 116 of the well array 102 can vary, ranging from 0.2 centimeter to 20 centimeters. In some embodiments, the width 116 of the well array 102 can be, or be about, 0.2, 0.2, 0.3, 0.4, 05, 0.6, 0.7, 0.8, 0.9, 1, 2, 3, 4, 5, 6, 7, 8, 9, 10, 20 centimeters, or a number or a range between any two of these values. In some embodiments, the width 116 of the well array 102 can be at least, or at most, 0.2, 0.3, 0.4, 05, 0.6, 0.7, 0.8, 0.9, 1, 2, 3, 4, 5, 6, 7, 8, 9, 10, or 20 centimeters.

The length 118 of the well array 102 can vary, ranging from 0.1 inch to 10 inches. In some embodiments, the length 118 of the well array 102 can be, or be about, 0.1, 0.2, 0.3, 0.4, 05, 0.6, 0.7, 0.8, 0.9, 1, 2, 3, 4, 5, 6, 7, 8, 9, 10 inches, or a number or a range between any two of these values. In some embodiments, the length 118 of the well array 102 can be at least, or at most, 0.1, 0.2, 0.3, 0.4, 05, 0.6, 0.7, 0.8, 0.9, 1, 2, 3, 4, 5, 6, 7, 8, 9, or 10 inches. The length 118 of the well array 102 can vary, ranging from 0.2 centimeter to 20 centimeters. In some embodiments, the length 118 of the well array 102 can be, or be about, 0.2, 0.2, 0.3, 0.4, 05, 0.6, 0.7, 0.8, 0.9, 1, 2, 3, 4, 5, 6, 7, 8, 9, 10, 20 centimeters, or a number or a range between any two of these values. In some embodiments, the length 118 of the well array 102 can be at least, or at most, 0.2, 0.3, 0.4, 05, 0.6, 0.7, 0.8, 0.9, 1, 2, 3, 4, 5, 6, 7, 8, 9, 10, or 20 centimeters.

In some embodiments, the footprint of the microwell array, for example defined by its width 116 and length 118, can be similar to that of a microtiter plate. In some embodiments, the footprint of the microwell array substrate can be similar to that of standard microscope slides. Non-limiting examples of the footprint of standard microscope slides include about 75 mm long×25 mm wide (about 3" long× about 1" wide) and about 75 mm long×50 mm wide (about 3" long×2" wide).

The thickness of the substrate within which the microwells are fabricated can range from about 0.1 mm thick to about 10 mm thick, or more. The thickness of the microwell array substrate can be, or be about, 0.1, 0.5, 1, 2, 3, 4, 5, 6, 7, 8, 9, 10 mm, or a number or a range between any two of these values. The thickness of the microwell array substrate can be at least, or at most, 10, 9, 8, 7, 6, 5, 4, 3, 2, 1, 0.5, 0.1 mm. The thickness of the microwell array substrate can be about 1 mm thick. The thickness of the microwell array substrate can be any value within these ranges, for example, the thickness of the microwell array substrate can be between about 0.2 mm and about 9.5 mm.

Microwell Array Surface Treatments

A variety of surface treatments and surface modification techniques can be used to modify the properties of microwell array surfaces. Examples can include, but are not limited to, oxygen plasma treatments to render hydrophobic material surfaces more hydrophilic, the use of wet or dry etching techniques to smooth or roughen glass and silicon surfaces, adsorption or grafting of polyethylene oxide or other polymer layers, for example pluronic, or bovine serum albumin to substrate surfaces to render them more hydrophilic and less prone to non-specific adsorption of biomolecules and cells, the use of silane reactions to graft chemically-reactive functional groups to otherwise inert silicon and glass surfaces, etc. Photodeprotection techniques can be used to selectively activate chemically-reactive functional groups at specific locations in the array structure, for example, the selective addition or activation of chemically-reactive functional groups such as primary amines or carboxyl groups on the inner walls of the microwells can be used to covalently couple oligonucleotide probes, peptides, proteins, or other biomolecules to the walls of the microwells. The choice of surface treatment or surface modification utilized can depend on the type of surface property that is desired and/or on the type of material from which the microwell array is made.

Microwell Sealing

The openings of microwells, for example the microwell array 102 shown in FIG. 1, can be sealed, for example, during cell lysis steps to prevent cross hybridization of target nucleic acid between adjacent microwells. A microwell (or array of microwells) can be sealed or capped using, for example, a flexible membrane or sheet of solid material (i.e. a plate or platten) that clamps against the surface of the microwell array substrate, or a suitable bead, where the diameter of the bead is larger than the diameter of the microwell.

A seal formed using a flexible membrane or sheet of solid material can comprise, for example, inorganic nanopore membranes (e.g., aluminum oxides), dialysis membranes, glass slides, coverslips, elastomeric films (e.g. PDMS), or hydrophilic polymer films (e.g., a polymer film coated with a thin film of agarose that has been hydrated with lysis buffer).

Solid supports (e.g., beads) used for capping the microwells can comprise any of the solid supports (e.g., beads) of the disclosure. In some embodiments, the solid supports are cross-linked dextran beads (e.g., Sephadex). Cross-linked dextran can range from about 10 micrometers to about 80 micrometers. In some embodiments, the cross-linked dextran beads used for capping can be, or be about, 10, 20, 30, 40, 50, 60, 70, 80 micrometers, or a number or a range between any two of these values. In some embodiments, the cross-linked dextran beads used for capping can be at least, or at most, 10, 20, 30, 40, 50, 60, 70, or 80 micrometers. The beads can be larger than the diameters of the microwells. In some embodiments, the beads can be, or be about, 10%, 20%, 30%, 40%, 50%, 60%, 70%, 80%, 90%, 99%, or a number or a range between any two of these values, larger than the diameter of the microwells. In some embodiments, the beads can be at least, or at most, 10%, 20%, 30%, 40%, 50%, 60%, 70%, 80%, 90%, or 99%, larger than the diameter of the microwells.

The seal or cap can allow buffer to pass into and out of the microwells, while preventing macromolecules (e.g., nucleic acids) from migrating out of the well. In some embodiments, a macromolecule of or of about 1, 2, 3, 4, 5, 6, 7, 8, 9, 10, 12, 13, 14, 15, 16, 17, 18, 19, 20, or a number or a range between any two of these values, nucleotides can be blocked from migrating into or out of the microwell by the seal or cap. In some embodiments, a macromolecule of at least, or at most, 1, 2, 3, 4, 5, 6, 7, 8, 9, 10, 12, 13, 14, 15, 16, 17, 18, 19, or 20 nucleotides can be blocked from migrating into or out of the microwell by the seal or cap.

Solid Support Manipulation

Solid supports (e.g., synthetic particles or beads) can be distributed among a substrate. Solid supports can be distributed among wells of the substrate, removed from the wells of the substrate, or otherwise transported through a device comprising one or more microwell arrays by means of centrifugation or other non-magnetic means. A microwell of a substrate can be pre-loaded with a solid support. A microwell of a substrate can hold or can hold about 1, 2, 3, 4, 5, 6, 7, 8, 9, 10 solid supports. A microwell of a substrate can hold at least, or at most, 1, 2, 3, 4, 5, 6, 7, 8, 9, 10 solid supports. In some embodiments, a microwell of a substrate can hold one solid support.

Consumables

Microwell arrays can be a consumable component of the assay system. Microwell arrays can be reusable. Microwell arrays can be configured for use as a stand-alone device for performing assays manually, or they can be configured to comprise a fixed or removable component of an instrument system that provides for full or partial automation of the assay procedure. In some embodiments of the disclosed methods, the bead-based libraries of stochastic barcodes can be deposited in the wells of the microwell array as part of the assay procedure. In some embodiments, the beads can be pre-loaded into the wells of the microwell array and provided to the user as part of, for example, a kit for performing stochastic barcoding and digital counting of nucleic acid targets.

Two Mated Microwell Arrays

In some embodiments, two mated microwell arrays can be provided, one pre-loaded with beads which are held in place by a first magnet, and the other for use by the user in loading individual cells. Following distribution of cells into the second microwell array, the two arrays can be placed face-to-face and the first magnet removed while a second magnet is used to draw the beads from the first array down into the corresponding microwells of the second array, thereby ensuring that the beads rest above the cells in the second microwell array and thus minimizing diffusional loss of target molecules following cell lysis, while maximizing efficient attachment of target molecules to the stochastic barcodes on the bead.

Substrates without Microwells

In some embodiments, a substrate does not include microwells. For example, beads can be assembled. For example, beads can be self-assembled. The beads can self-assemble into a monolayer. The monolayer can be on a flat surface of the substrate. The monolayer can be on a curved surface of the substrate. The bead monolayer can be formed by any method, such as alcohol evaporation.

Individual cells and beads can be compartmentalized using alternatives to microwells, for example, a single solid support and a single cell could be confined within a single droplet in an emulsion (e.g. in a droplet digital microfluidic system).

Cells could be confined within porous beads that themselves comprise the plurality of tethered stochastic barcodes. Individual cells and solid supports can be compartmentalized in any type of container, microcontainer, reaction chamber, reaction vessel, or the like.

Single cell, stochastic barcoding can be performed without the use of microwells. Single cell, stochastic barcoding assays can be performed without the use of any physical container. For example, stochastic barcoding without a physical container can be performed by embedding cells and beads in close proximity to each other within a polymer layer or gel layer to create a diffusional barrier between different cell/bead pairs. For example, stochastic barcoding without a physical container can be performed in situ, in vivo, on an intact solid tissue, on an intact cell, and/or subcellularly.

Flow Cytometric Deposition

A plurality of single droplets, for example a plurality of first single droplets, a plurality of second single droplets, a plurality of single cells, a plurality of synthetic particles can be introduced into microwells of a microwell array, for example the microwell array 102 shown in FIG. 1. In some embodiments, introducing the plurality of droplets can comprise flow cytometrically depositing the plurality of droplets into the microwells of the microwell array. Flow cytometrically depositing the plurality of droplets into the microwells of the microwell array can comprise using a flow cytometer to deposit a single first droplet at a time into the microwells of the microwell array. In some embodiments, the methods can comprise aligning a sorting component of a flow cytometer with the microwell array.

A plurality of single cells can be introduced into microwells of a microwell array. In some embodiments, introducing the plurality of single cells into the microwells of the microwell array can comprise flow cytometrically depositing the plurality of cells into the microwells of the microwell array. Flow cytometrically depositing the plurality of single cells into the microwells of the microwell array can comprise using a flow cytometer to deposit a single cell at a time into the microwells of the microwell array.

A plurality of synthetic particles such as beads can be introduced into microwells of a microwell array. In some embodiments, introducing the plurality of synthetic particles into the microwells of the microwell array can comprise flow cytometrically deposing the synthetic particles into the microwells of the microwell array. Flow cytometrically depositing the plurality of synthetic particles into the microwells of the microwell array can comprise using a flow cytometer to deposit a synthetic particle at a time into the microwells of the microwell array.

Reagent can be introduced into microwells of a microwell array. In some embodiments, introducing the reagent can comprise flow cytomertrically depositing the reagent into the microwells. In some embodiments, the reagent comprises synthetic particles such as beads and flow cytometrically depositing the reagent into the microwells can comprise using a flow cytometer to deposit a synthetic particle at a time into the microwells of the microwell array Flow Cytometer Flow cytometers can be used for analyzing and sorting particles in a fluid sample, such as cells in a blood sample or particles of interest in any other type of biological or chemical sample. A flow cytometer can include a sample reservoir for receiving a fluid sample, such as a blood sample, and a sheath reservoir containing a sheath fluid. The flow cytometer transports the particles (e.g., the cells) in the fluid sample as a particle stream to a flow cell, while also directing the sheath fluid to the flow cell.

Within the flow cell, a liquid sheath can be formed around the cell stream to impart a substantially uniform velocity on the cell stream. The flow cell can hydrodynamically focus the cells within the stream to pass through the center of a laser beam in a flow cell. The point at which the cells intersect the laser beam is commonly known as the interrogation point. As a cell moves through the interrogation point, it causes the laser light to scatter. The laser light also excites components in the cell stream that have fluorescent properties, such as fluorescent markers that have been added to the fluid sample and adhered to certain cells of interest, or fluorescent beads mixed into the stream. The flow cytometer can include an appropriate detection system that includes photomultiplier tubes, photodiodes or other light detecting devices, which are focused at the intersection point. The flow cytometer analyzes the detected light to measure physical and fluorescent properties of the cell. The flow cytometer can further sort the cells based on these measured properties. The flow stream exits the flow cell via a nozzle with a nozzle diameter that is appropriate for the fluidics system and sort rate desired.

To sort cells by an electrostatic method, the desired cell can be contained within an electrically charged droplet. To produce droplets, the flow cell can be rapidly vibrated by an acoustic device, such as a piezoelectric element. The volume of a droplet can be estimated by the hydrodynamic properties of the flow stream and the nozzle dimensions. To charge the droplet, the flow cell can include a charging element whose electrical potential can be rapidly changed. Because the cell stream exits the flow cell in a substantially downward vertical direction, the droplets also propagate in that direction after they are formed. Droplets, whether they are charged or are uncharged can be collected in a sample collection vessel that is appropriately directed to collect the one or more flow streams generated by the deflection plates. Accordingly, the droplets and the cells contained therein may be collected in appropriate collection vessels downstream of the plates.

In using flow cytometers, the flow stream and collection vessels can be manually aligned. The fluidics parameters such as flow rate and sheath fluid composition can be matched with an appropriate nozzle diameter.

Figure 2:
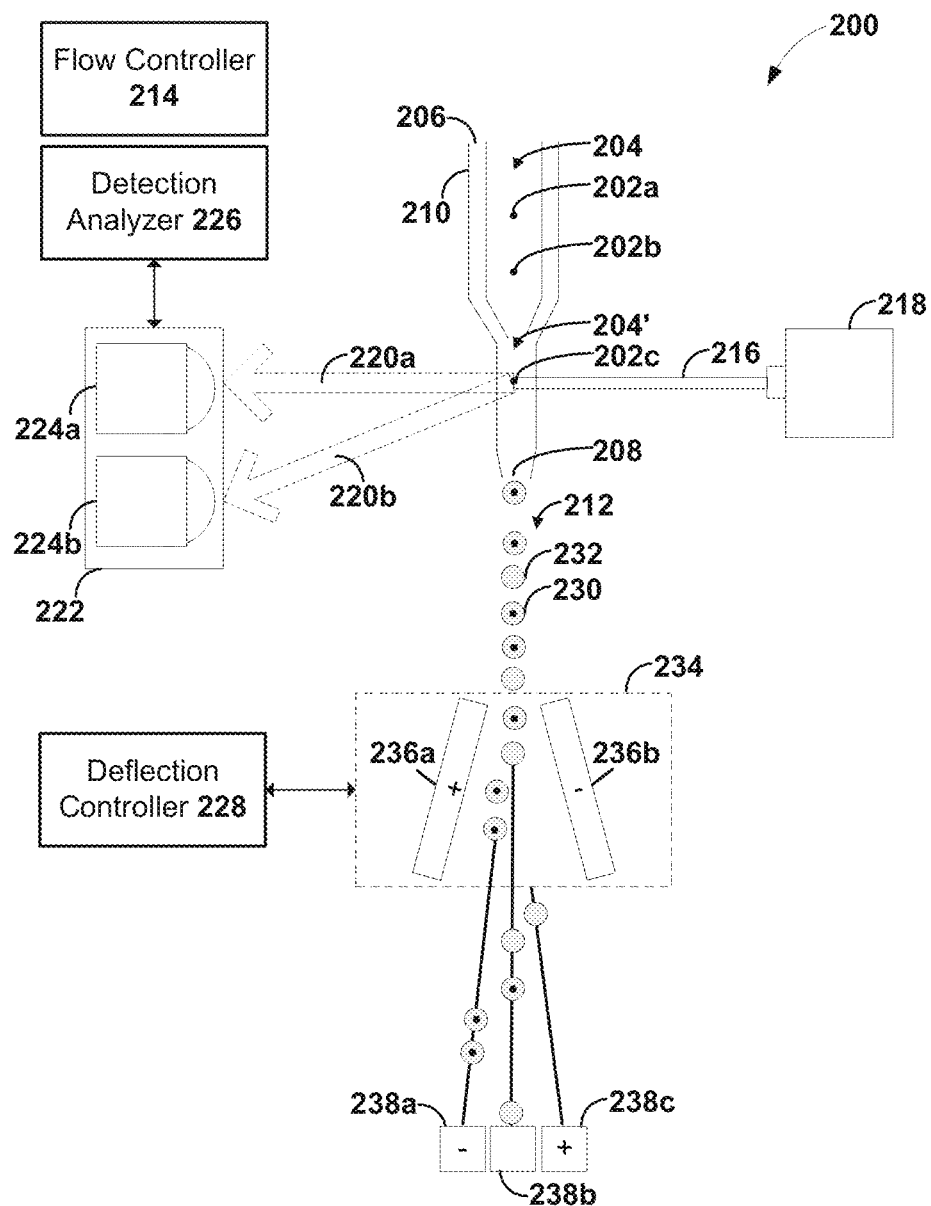
FIG. 2 is a non-limiting schematic illustration of a sorting device suitable for producing high density droplet arrays.

FIG. 2 is a non-limiting schematic illustration of a sorting device 200, for example a flow cytometer, suitable for producing high density droplet arrays, including high density cellular arrays and high density synthetic particle array. The sorting device illustrated in FIG. 2, referred to as a stream-in-air sorting system, can sort cells and synthetic particles. Cells 202*a*, 202*b*, and 202*c* in a sample stream 204 are shown. The sample stream 204, after combining with a sheath fluid 206, can form a combined sample stream 204' that can pass through an orifice 208 of a nozzle 210. The combined sample stream 204', upon exiting the nozzle 210, can form a jet 212.

The sorting device 200 can include a flow controller 214 configured to monitor and adjust the pressures and the flow rates of the sample stream 204 and the sheath fluid 206. The flow controller 212 can be configured to adjust one or more characteristic of the nozzle 208 such as the size of the orifice 206.

A laser beam 216 generated by a laser 218 can illuminate the cells in the combined sample stream 204'. When the laser beam 216 generated by the laser 218 intersects the combined sample stream 204', the laser beam 216 can be scattered by, for example, the cells present in the sample stream 204. For example, when the laser beam 214 intersects the cell 202*c*, the cell 202*c* can scatter the laser beam 216. A first portion of the scattered laser light, known as the forward scattered light 220*a*, can propagate in the direction of the laser beam 216 prior to intersecting the sample stream 204. A second portion of the scattered laser light, known as side scattered light 220*b*, can propagate in a direction at an angle to the direction of the laser beam 216. The scattered light can be detected by one or more detection stations, for example a detection station 222, to generate multiple signals. The detection station 222 can comprise two imaging sensors 224*a* and 224*b*. The imaging sensor 224*a* can detect the forward scattered light 220*a*, and the imaging sensor 222*b* can detect the side scattered light 220*b*. In some embodiments, imaging sensors 224*a* and 224*b* can be hosted in separate detection stations.

A detection analyzer 226 can process and analyze the multiple signals detected by the detection station 222, for example the imaging sensors 224*a* and 224*b*, to generate a sample event data point, for example a multi-parameter sample event data point. A sample event data point can include information such as maximum fluorescent intensities, mean fluorescent intensities, and changes in fluorescent intensities.

The detection analyzer 226 can be configured to generate different sample event data points in response to identical forward scattered light 220*a* and side scattered light 220*b*. For example, the timing of detection, the resolution of detection, or the area of detection can be adjusted. By adjusting the detection to a less rigorous scheme, the speed at which the detection station 222 can operate may be increased due to the reduced complexity of information processing performed. This may advantageously reduce the power resources consumed during sample sorting.

Based on the values of sample event data points, after droplets leave the nozzle 210, a deflection controller 228 can be configured to determine whether the droplets in the jet 212 should be charged and the extent of the charges. For example, the droplets in the jet 212 can be positively charged, negatively charged, or not charged. Some droplets can include a cell of the sample as shown by a droplet 230 while other droplets may not include a cell of the sample as shown by a droplet 232.

Droplets can pass through a deflection field 234 controlled by the deflection controller 228. The deflection field 234 can include two oppositely charged deflection plates 236*a* and 236*b*. The deflection plates 236*a* and 236*b* can be configured to steer charged droplets in the jet 212 to their respective collection vessels 238*a*, 238*b*, or 238*c*. As shown, the collection vessel 23*ab* can collect negatively charged droplets because the positively charged deflection plate 236*a* can attract negatively charged droplets. Similarly, the collection vessel 238*c* can collect positively charged droplets because the negatively charged deflection plate 236b can attract positively charged droplets. Each collection vessel can be a microwell plate or a microwell of a microtiter plate.

The deflection controller 228 can be configured to control the strength of the deflection field 234 created by the deflection plates 236a and 236b. The detection analyzer 214 can be configured to provide information to the deflection controller 236a to adjust the deflection field 234 based on the sample behavior. For example, the strength of the deflection field 234 can be adjusted such that one or both deflection plates 236a and 236b have higher or lower levels of attraction. The strength can be precisely calibrated to attract only those particles of interest to increase purity. The strength can be increased to increase yield.

In some embodiments, the flow system 200 can identify all cells of interest based on the characteristics of the sample event data points generated by the detection station 222 in response to the forward scattered light 220a and the side scattered light 220b. Based on the characteristics of the sample event data points, the flow system 200 can cause the droplets in the jet 212 to be charged or not charged when the cells of interest leave the nozzle 210 as droplets. The flow system 200 can cause droplets with the cells of interest to have the same charge. This allows collection of the cells of interest in the same collection vessel, including the same or different microwells of a microwell plate.

The flow controller 214, the detection analyzer 226, the deflection controller 228, and other elements of the flow system 200 can be configured to coordinate their operations with one another. For example, the flow rates of the sample stream 204 and the sheath fluid 206 can be adjusted by actuating the nozzle 210 while also adjusting the deflection field 234. Adjusting the flows rates may also necessitate the adjustment of the detection station 222 to ensure the sample event data points are generated for the new flow rate.

Introduction of Droplets to Desired Locations

Using the methods, compositions and systems disclosed herein, one or more droplets can be introduced into microwells of a microwell array at one or more desired locations, for example, to produce a droplet array. In some embodiments, introducing a plurality of droplets into the microwells of the microwell array can comprise introducing the plurality of droplets into the microwells of the microwell array at a plurality of desired locations. The plurality of droplets can be, or can comprise, for example, a plurality of droplets, a plurality of cells, a plurality solid supports, or a plurality of synthetic particles. In some embodiments, introducing the plurality of cells in the sample into the microwells of the microwell array can comprise introducing the plurality of cells in the sample into the microwells of the microwell array at a plurality of desired locations, for example a plurality of first desired locations. In some embodiments, introducing the plurality of synthetic particles into the microwells of the microwell array can comprise introducing the plurality of synthetic particles into the microwells of the microwell array at a plurality of desired locations, for example a plurality of second desired locations.

The plurality of desired locations can vary. In some embodiments, a desired location can be a microwell of the microwell array. In some embodiments, a desired location can be within a microwell of the microwell array, for example, at the center of the microwell. In some embodiments, a desired location can be close to the center of a microwell of the microwell array. In some embodiments, a desired location can be at an edge of a microwell of the microwell array. In some embodiments, a desired location can be close to an edge of a microwell of the microwell array.

Aligning a Microwell Array

Alignment Systems

Figure 3A:
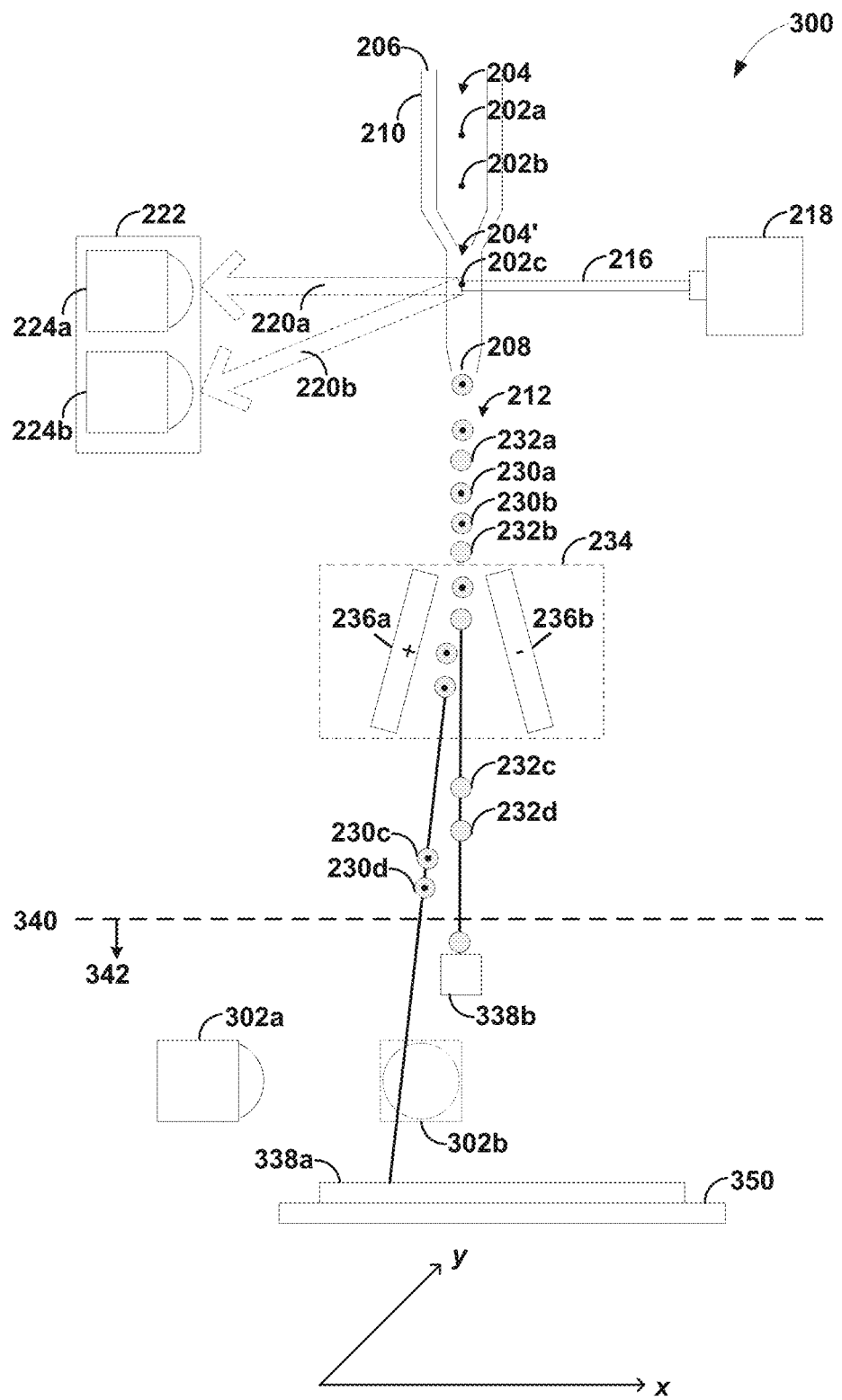
FIGS. 3A-B schematically illustrate a non-limiting exemplary sorting device with two orthogonal cameras for aligning an alignment microwell array.
Figure 3B:
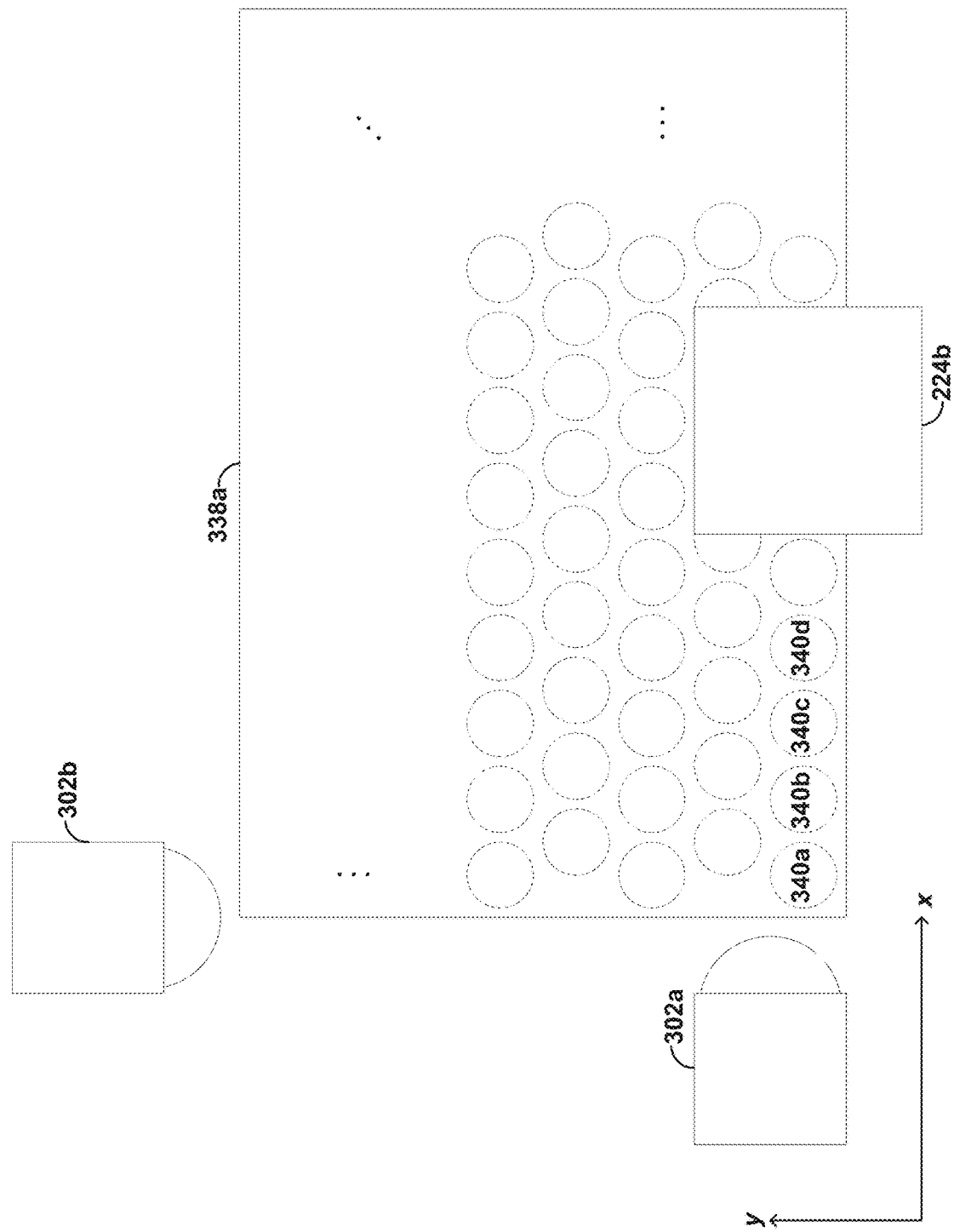

Disclosed herein are methods for aligning alignment microwell arrays, for example a first alignment microwell array, for producing sample microwell arrays, for example a cellular array and a synthetic particle array. FIGS. 3A-B schematically illustrate a non-limiting exemplary sorting device 300 with a number of imaging sensors, for example two orthogonal alignment imaging sensors 302a and 302b, for aligning an alignment microwell array 338a. In some embodiments, the number of imaging sensors can vary. For example, the number of imaging sensors can be, or be about, 1, 2, 3, 4, 5, 6, 7, 8, 9, 10, 20, 30, 40, 50, 60, 70, 80, 90, 100, or a number or a range between any two of these values. In some embodiments, the number of imaging sensors can vary. For example, the number of imaging sensors can be at least, or at most, 1, 2, 3, 4, 5, 6, 7, 8, 9, 10, 20, 30, 40, 50, 60, 70, 80, 90, or 100.

FIG. 3A shows a side view of the non-limiting exemplary sorting device 300. FIG. 3B shows a top view of the non-limiting exemplary sorting device 300 from a plane 340 in a direction 342 in FIG. 3. The alignment microwell array 338a can comprise a plurality of microwells, for example microwells 340a-d, and can be positioned on a stage 350 (also referred to as a support stage) of the sorting device 300.

In some embodiments, the sorting device 300 includes one or more support stages 350, as desired, such as two or more, such as three or more, such as four or more and including five or more support stages. For example, the number of support stages may range from 1 to 10 support stages, such as from 2 to 7 support stages and including from 3 to 5 support stages. In certain embodiments, systems of interest include one support stage. In other embodiments, systems include two support stages. In one example, the subject systems include a support stage having a container for collecting droplets from the flow stream. In another example, the subject systems include a support stage having a mounted laser. In yet another example, the subject system includes a first support stage having a mounted laser and a second support stage having a container for collecting droplets from the flow stream.

In some embodiments, support stages are movable. For instance, in one example the support stage may be moved to adjust the position collection containers on the support stage so that they are aligned with the flow stream. In another example, the support stage may be moved to adjust the position of a laser. In some embodiments, the support stage is moved in two dimensions, such as in an X-Y plane orthogonal to the axis of the flow stream. In other instances, the support structure is moved in three dimensions. Where the support stage is configured to move, the support stage may be moved continuously or in discrete intervals. In some embodiments, the support stage is moved in a continuous motion. In other embodiments, the support stage is moved in discrete intervals, such as for example in 0.01 micron or greater increments, such as 0.05 micron or greater, such as 0.1 micron or greater, such as 0.5 micron or greater, such as 1 micron or greater, such as 10 micron or greater, such as 100 microns or greater, such as 500 microns or greater, such as 1 mm or greater, such as 5 mm or greater, such as 10 mm or greater and including 25 mm or greater increments.

Any displacement protocol may be employed to move the support structures, such as moving the support stages with a motor actuated translation stage, leadscrew translation assembly, geared translation device, such as those employing a stepper motor, servo motor, brushless electric motor, brushed DC motor, micro-step drive motor, high resolution stepper motor, among other types of motor.

Systems in some embodiments can include one or more support stages operably coupled to the processors. Suitable support stages can be any convenient mounting device configured to hold in place one or more components of the subject systems, such as planar substrate, contoured mounting devices, cylindrical or tubular support structures, laser or LED holders, among other types of support structures. In some embodiments, the support stage is a mount for an illumination device, such as a laser or an LED. In other embodiments, systems include a support structure for holding one or more containers for collecting particles from the flow stream. For example, the support stage may be configured to hold in place containers including, but are not limited to test tubes, conical tubes, multi-compartment containers such as microtiter plates (e.g., 96-well plates), centrifuge tubes, culture tubes, microtubes, caps, cuvettes, bottles, rectilinear polymeric containers, among other types of containers.

The sorting device 300, similar to the sorting device 200 illustrated in FIG. 2, can be configured for sorting and depositing cells and synthetic particles, for example alignment synthetic particles 202a, 202b, and 202c in an alignment stream 204. The alignment stream 204, after combining with a sheath fluid 206, can generate a combined alignment stream 204' that can pass through an orifice 208 of a nozzle 210. The combined alignment stream 204', upon exiting the nozzle 210, can form a jet 212. A flow controller 214 of the sorting device 300 can be configured to monitor and adjust the pressures and the flow rates of the alignment stream 204 and the sheath fluid 206 and to adjust one or more characteristic of the nozzle 208 such as the size of the orifice 206.

A laser beam 216 generated by a laser 218 can be scattered by the alignment synthetic particles, for example the alignment synthetic particle 202c, in the combined alignment stream 204'. After being scattered by the alignment synthetic particles, the laser beam 216 can produce a forward scattered light 220a and a side scattered light 220b, propagating in the direction of the laser beam 216 and in a direction at an angle to the direction of the laser beam 216 respectively.

The sorting device can comprise a detection station 222 for detecting the forward scattered light 220a by, for example, an imaging sensor 222a and the side scattered light 220b by, for example, an imaging sensor 222b. A detection analyzer 226 can process and analyze the multiple signals detected by the imaging sensors 222a and 222b to generate a sample event data point, for example a multi-parameter sample event data point.

Based on the values of sample event data points, after droplets leave the nozzle 210, a deflection controller 228 can be configured to determine whether the droplets in the jet 212 should be positively charged, negatively charged, or not charged. Some droplets can include alignment synthetic particles of the alignment sample as shown by alignment droplets 230a-230d while other droplets may not include any alignment synthetic particle of the alignment sample as shown by non-alignment droplets 232a-232d.

Droplets can pass through a deflection field 234 controlled by the deflection controller 228. The deflection field 234 can include two oppositely charged deflection plates 236a and 236b. The deflection plates 236a and 236b can be configured to steer negatively charged alignment droplets 230a-230d in the jet 212 such that the alignment microwell array 238a can collect the negatively charged alignment droplets 230a-230d that include synthetic particles. Because the non-alignment droplets 232a-232d in the jet 212 do not contain alignment synthetic particles, they are not charged and are not steered by the deflection plates 236a and 236b. Thus non-alignment droplets 232a-232d are collected in a waste receiving vessel 238b.

The functions of the two alignment imaging sensors 302a and 302b can vary. In some embodiments, the alignment imaging sensor 302a can determine the alignment droplets' locations on the alignment microwell array 338a in the x direction. In some embodiments, the alignment imaging sensor 302a can determine the alignment droplets' locations on the alignment microwell array 338a in the y direction. In some embodiments, the alignment imaging sensor 302a can determine the alignment droplets' locations on the alignment microwell array 338a in both the x direction and the y direction. In some embodiments, the alignment imaging sensor 302b can determine the alignment droplets' locations on the alignment microwell array 338a in the y direction. In some embodiments, the alignment imaging sensor 302a can determine the alignment droplets' locations on the alignment microwell array 338a in the x direction. In some embodiments, the alignment imaging sensor 302a can determine the alignment droplets' locations on the alignment microwell array 338a in both the x direction and the y direction.

The positioning of the two alignment imaging sensors 302a and 302b can vary. In some embodiments, the alignment imaging sensor 302a can be located between the deflection field 234 and the stage 350. In some embodiments, the alignment imaging sensor 302a can be located between the waste receiving vessel 238a and the stage 350. In some embodiments, the alignment imaging sensor 302a can be located between the waste receiving vessel 238a and the alignment microwell array 338a. In some embodiments, the alignment imaging sensor 302a can be located between the waste receiving vessel 238a and the deflection field 234. In some embodiments, the alignment imaging sensor 302a can be located between the waste receiving vessel 238a and the deflection plates 236a and 236b.

The positioning of the two alignment imaging sensors 302a and 302b with respect to each other can vary. In some embodiments, the alignment imaging sensors 302a and 302b can be on the same plane, for example an x-y plane. In some embodiments, the alignment imaging sensor 302a can be above the alignment imaging sensor 302b, for example the alignment imaging sensor 302a can be on a first x-y plane and the alignment imaging sensor 302b can be on a second x-y plane, wherein the first x-y plane is further away from the stage 350 closer to the deflection field 234. In some embodiments, the alignment imaging sensor 302a can be below the alignment imaging sensor 302b. In some embodiments, the vertical positioning, for example the z direction, of the alignment imaging sensors 302a and 302b can overlap. In some embodiments, the horizontal positioning, for example the x direction and the y direction, of the alignment imaging sensors 302a and 302b can overlap.

The relative orientation of the two alignment imaging sensors 302a and 302b can vary. In some embodiments, the two alignment imaging sensors 302a and 302b can be approximately orthogonal to each other. For example, the two alignment imaging sensors 302a and 302b can be orthogonal to each other. For example, the two alignment imaging sensors 302a and 302b can be at 90° to each other. For example, the two alignment imaging sensors 302a and 302b can be at 90°±E° to each other. The 6 can vary. For example, the 6 can be, or be about, 0.00001°, 0.0001°, 0.001°, 0.01°, 0.1°, 1°, 2°, 3°, 4°, 5°, 6°, 7°, 8°, 9°, 10°, or a number or a range between any two of these values. For example, the 6 can be at least, or at most, 0.00001°, 0.0001°, 0.001°, 0.01°, 0.1°, 1°, 2°, 3°, 4°, 5°, 6°, 7°, 8°, 9°, or 10°.

In some embodiments, the two alignment imaging sensors 302a and 302b can be at an angle to each other. For example, the angle between the two alignment imaging sensors 302a and 302b can be, or be about, 0°, 10°, 20°, 30°, 40°, 50°, 60°, 70°, 80°, 90°, 100°, 110°, 120°, 130°, 140°, 150°, 160°, 170°, 180°, 190°, 200°, 220°, 230°, 240°, 250°, 260°, 270°, 280°, 290°, 300°, 310°, 320°, 330°, 340°, 350°, 360°, or a number or a range between any two of these values. For example, the angle can be at least, or at most, 0°, 10°, 20°, 30°, 40°, 50°, 60°, 70°, 80°, 90°, 100°, 110°, 120°, 130°, 140°, 150°, 160°, 170°, 180°, 190°, 200°, 220°, 230°, 240°, 250°, 260°, 270°, 280°, 290°, 300°, 310°, 320°, 330°, 340°, 350°, or 360°.

Stream Alignment System

Disclosed herein are systems and methods of automatic cell sorting. Aspects of the systems include an image-based automated stream adjuster. The image-based automated stream adjuster provides for automatic set-up of the deflected stream(s) of a sorting device (e.g., a cell sorter) to minimize or eliminate user tasks after an initial calibration (e.g., which can take place at the factory).

In some embodiments, the system comprises: a cell sorting component (which can include a nozzle, an orifice, a deflection plate, or any combination thereof). The system can comprise non-transitory memory configured to store executable instructions; and a processor in communication with the cell sorting component and the non-transitory memory, the processor programmed by the executable instructions to: (a) receive a first parameter used to deposit the first alignment droplet to the desired location on athe first alignment microwell array; (b) cause the cell sorting component deposit a second alignment droplet to a second alignment microwell array using the first parameter; and (c) determine a path of the second alignment droplet, from the cell sorting component to the second alignment microwell, in the first detection field using a first imaging sensor, wherein the first imaging sensor is located between the cell sorting component and a waste receiving vessel; and (d) determine a first measurement between a first position of a path of the first alignment droplet in the first detection field and a corresponding first position of the path of the second droplet in the first detection field. In some embodiments, the processor is programmed to: cause the cell sorting component introduce droplets into microwells of a microwell array using the first parameter to produce a cellular array.

Figure 4A:
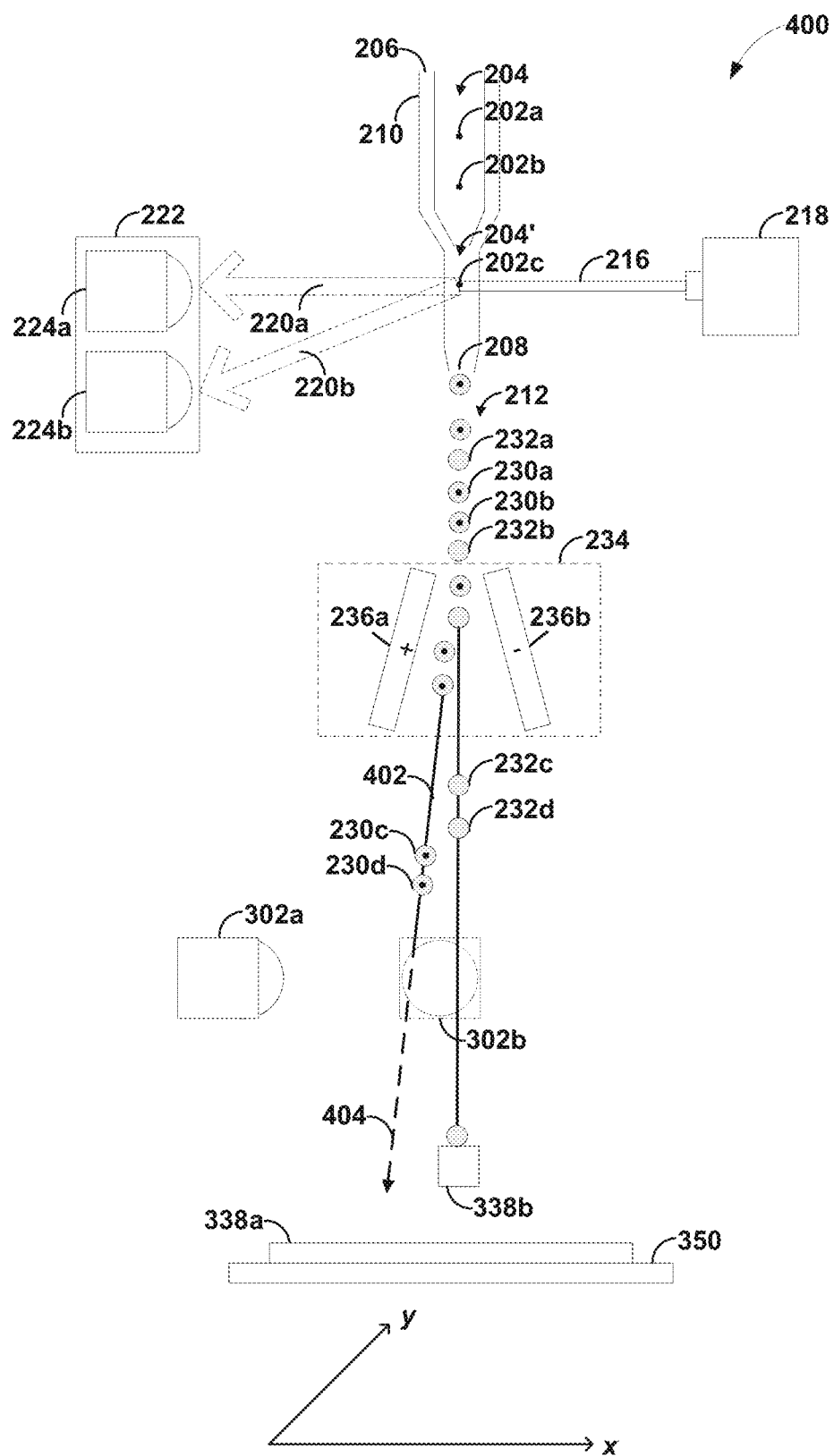
FIG. 4A shows schematic illustration of a non-limiting exemplary sorting device for stream alignment.
Figure 4B:
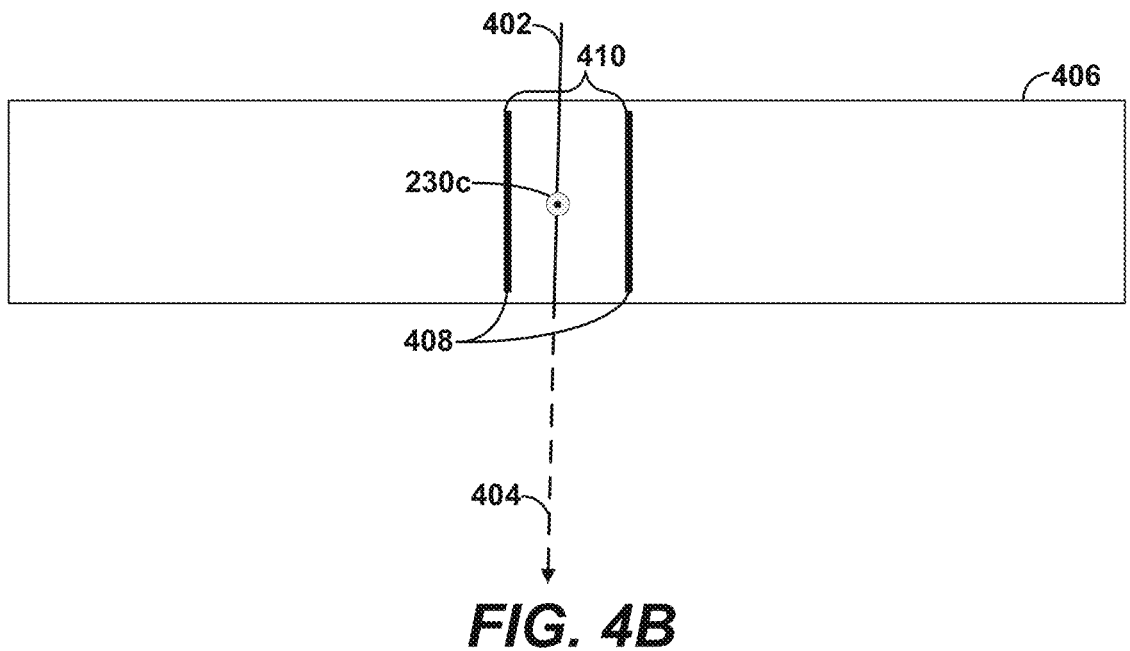
FIGS. 4B-4C each shows a non-limiting exemplary image of a deflected stream with two bars representing a correct path.
Figure 4C:
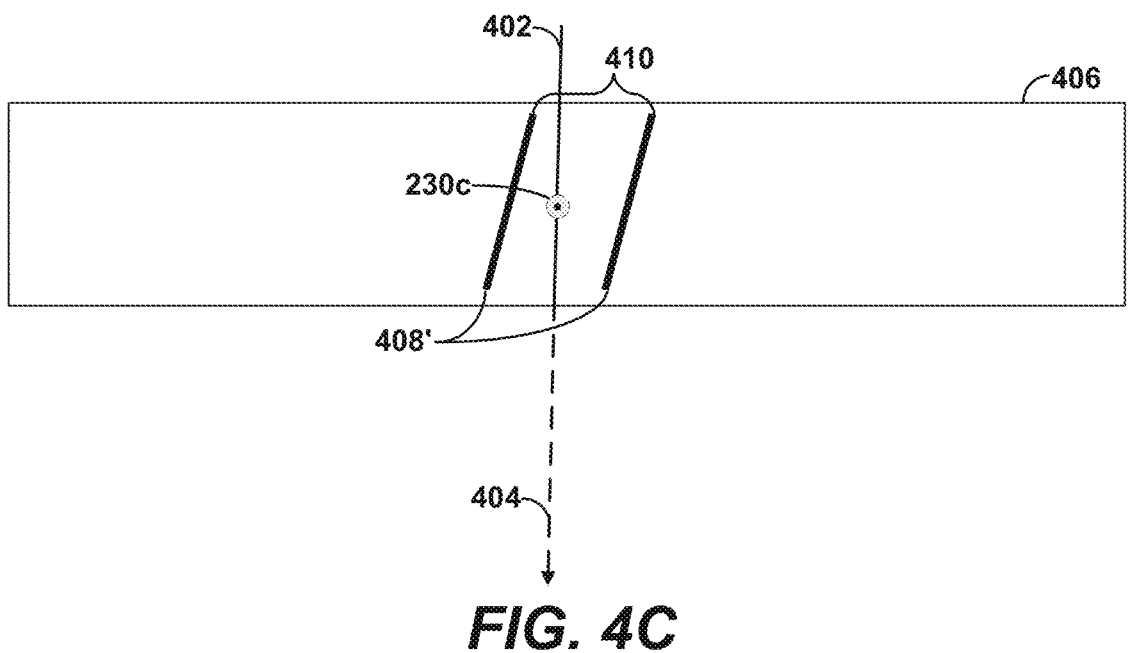

FIG. 4A shows schematic illustration of a non-limiting exemplary sorting device 400 for stream alignment. In some embodiments, a camera (e.g., a camera 302a or 302b) takes an image of a deflected stream 402 in a correct path 404 and then creates a modified version 406 with a plurality of parallel bars 408 or lines (e.g., two parallel bars shown in FIG. 4B) or non-parallel bars 408' or lines (e.g., two non-parallel bars shown in FIG. 4B). The two parallel bars 408 can represent a channel 410 where a fluid stream 402 should be traveling in order to get accurate sorts (e.g., to get a properly deflected particle 230c into the correct tube or well plate 338a). If the stream 402 is not properly positioned (e.g., the stream 402 is not in the channel 410 represented by the two parallel bars 408 or non-parallel bars 408', the instrument can vary one or more parameters, e.g., by modulating, such as increasing or decreasing the voltage, on the deflection plates to move the streams into the correct path 404. The stream 402 may be illuminated for detection using any convenient protocol, e.g., by employing a laser that is shined left to right in order to illuminate the streams and moves in and out of the picture to find the best intercept.

In some embodiments, each channel 410 can be calibrated to a desired position (e.g., a tube or a microwell position). A pair of bars 408 (e.g., parallel bars) can correspond to a path of a fluid stream 404 that falls into the desired position. During calibration, a test sort can be performed to determine the channel 410 and the position of the pair of lines 408.

Deflection Plate Voltage

As illustrated herein, systems can include one or more processors (e.g., the processor 602 shown in FIG. 6) operably coupled to the imaging sensors where the processors are configured to automatically adjust one or more flow streams, e.g., as described herein. In some embodiments, the processor may be configured to adjust the drop charging voltage in response to a data signal corresponding to one or more properties of the flow stream determined based on the captured images. In some embodiments, the drop charging voltage is increased, such as by 0.01 V or more, such as 0.05 V or more, such as 0.1 V or more, such as by 0.5V or more, such as by 1V or more, such as by 5V or more, such as by 10V or more, such as by 15V or more, such as by 25V or more, such as by 50V or more and including increasing the drop charging voltage by 75V or more. For example, the drop charging voltage may be increased by 1% or more, such as by 5% or more, such as by 10% or more, such as by 15% or more, such as by 25% or more, such as by 50% or more, such as by 75% or more and including increasing the drop charging voltage by 90% or more. In other instances, the drop charging voltage is reduced, such as by 0.01 V or more, such as 0.05 V or more, such as 0.1 V or more, such as by 0.5V or more, such as by 1V or more, such as by 5V or more, such as by 10V or more, such as by 15V or more, such as by 25V or more, such as by 50V or more and including reducing the drop charging voltage by 75V or more. For example, the drop charging voltage may be reduced by 1% or more, such as by 5% or more, such as by 10% or more, such as by 15% or more, such as by 25% or more, such as by 50% or more, such as by 75% or more and including reducing the drop charging voltage by 90% or more.

In yet other embodiments, the processor may be configured to adjust the deflection plate voltage in response to a data signal corresponding to one or more properties of the flow stream determined based on the captured images. In some embodiments, the deflection plate voltage is increased, such as by 5V or more, such as by 10V or more, such as by 50V or more, such as by 100V or more, such as by 250V or more, such as by 500V or more, such as by 1000V or more and including increasing the drop charging voltage by 2000V or more. For example, the deflection plate voltage may be increased by 1% or more, such as by 5% or more, such as by 10% or more, such as by 15% or more, such as by 25% or more, such as by 50% or more, such as by 75% or more and including increasing the deflection plate voltage by 90% or more. In other instances, the drop charging voltage is reduced, such as by 0.5V or more, such as by 5V or more, such as by 10V or more, such as by 50V or more, such as by 100V or more, such as by 250V or more, such as by 500V or more, such as by 1000V or more and including reducing the deflection plate voltage by 2000V or more. For example, the deflection plate voltage may be reduced by 1% or more, such as by 5% or more, such as by 10% or more, such as by 15% or more, such as by 25% or more, such as by 50% or more, such as by 75% or more and including reducing the deflection plate voltage by 90% or more.

In still other embodiments, the processor may be configured to adjust the drop drive frequency in response to a data signal corresponding to one or more properties of the flow stream determined based on the captured images. In some embodiments, the drop drive frequency is increased, such as by 0.01 Hz or more, such as by 0.05 Hz or more, such as by 0.1 Hz or more, such as by 0.25 Hz or more, such as by 0.5 Hz or more, such as by 1 Hz or more, such as by 2.5 Hz or more, such as by 5 Hz or more, such as by 10 Hz or more and including by 25 Hz or more. For example, the drop drive frequency may be increased by 1% or more, such as by 5% or more, such as by 10% or more, such as by 15% or more, such as by 25% or more, such as by 50% or more, such as by 75% or more and including increasing the drop drive frequency by 90% or more. In other instances, the drop drive frequency is reduced, such as by 0.01 Hz or more, such as by 0.05 Hz or more, such as by 0.1 Hz or more, such as by 0.25 Hz or more, such as by 0.5 Hz or more, such as by 1 Hz or more, such as by 2.5 Hz or more, such as by 5 Hz or more, such as by 10 Hz or more and including by 25 Hz or more. For example, the drop drive frequency may be reduced by 1% or more, such as by 5% or more, such as by 10% or more, such as by 15% or more, such as by 25% or more, such as by 50% or more, such as by 75% or more and including reducing the drop frequency by 90% or more. In still other embodiments, the processor may be configured to adjust the drop delay in response to a data signal corresponding to one or more properties of the flow stream determined based on the captured images. In some embodiments, the drop delay is increased, such as by 0.01 microseconds or more, such as by 0.05 microseconds or more, such as by 0.1 microseconds or more, such as by 0.3 microseconds or more, such as by 0.5 microseconds or more, such as by 1 microseconds or more, such as by 2.5 microseconds or more, such as by 5 microseconds or more, such as by 7.5 microseconds or more and including increasing the drop delay by 10 microseconds or more. For example, the drop delay may be increased by 1% or more, such as by 5% or more, such as by 10% or more, such as by 15% or more, such as by 25% or more, such as by 50% or more, such as by 75% or more and including increasing the drop delay by 90% or more. In other instances, the drop frequency is reduced, such as by 0.01 microseconds or more, such as by 0.05 microseconds or more, such as by 0.1 microseconds or more, such as by 0.3 microseconds or more, such as by 0.5 microseconds or more, such as by 1 microseconds or more, such as by 2.5 microseconds or more, such as by 5 microseconds or more, such as by 7.5 microseconds or more and including reducing the drop delay by 10 microseconds or more. For example, the drop delay may be reduced by 1% or more, such as by 5% or more, such as by 10% or more, such as by 15% or more, such as by 25% or more, such as by 50% or more, such as by 75% or more and including reducing the drop delay by 90% or more.

In still other embodiments, the processor may be configured to adjust the drop amplitude in response to a data signal corresponding to one or more properties of the flow stream determined based on the captured images. In some embodiments, the drop amplitude is increased, such as by 0.01 volts or more, such as by 0.025 volts or more, such as by 0.05 volts or more, such as by 0.1 volts or more, such as by 0.25 volts or more, such as by 0.5 volts or more and including increasing the drop amplitude by 1 volt or more. For example, the drop amplitude may be increased by 1% or more, such as by 5% or more, such as by 10% or more, such as by 15% or more, such as by 25% or more, such as by 50% or more, such as by 75% or more and including increasing the drop amplitude by 90% or more. In other instances, the drop amplitude is reduced, such as by 0.01 volts or more, such as by 0.025 volts or more, such as by 0.05 volts or more, such as by 0.075 volts or more, such as by 0.1 volts or more, such as by 0.25 volts or more and including reducing the drop amplitude by 1 volt or more. For example, the drop amplitude may be reduced by 1% or more, such as by 5% or more, such as by 10% or more, such as by 15% or more, such as by 25% or more, such as by 50% or more, such as by 75% or more and including reducing the drop amplitude by 90% or more.

In some embodiments, the processor is operably coupled to an imaging sensor which captures images of a flow cytometer flow stream in a detection field and generates a data signal corresponding to the physical dimensions of the flow stream based on the captured images. Where the flow stream is a continuous stream, in some embodiments the processor is configured to take the captured images and generate a data signal corresponding to the width of the flow stream. In detection fields where the flow stream is composed of discrete droplets, in some embodiments the processor is configured to generate a data signal corresponding to droplet diameter.

Microwell Array Alignment Method

Disclosed herein are methods for aligning alignment microwell arrays, for example a first alignment microwell array, for producing sample microwell arrays. In some embodiments, the methods can comprise: (a) determining a first parameter using a first imaging sensor and a second parameter using a second imaging sensor (b) providing a desired location on an alignment microwell array, for example a first alignment array, in an x direction and a y direction; (c) depositing an alignment droplet, for example a first alignment droplet, into a microwell of the alignment microwell array based on the first parameter and the second parameter; (d) determining the distance between the alignment droplet's location on the alignment microwell array and the desired location; (e) adjusting the first parameter and the second parameter based on the distance between the alignment droplet's location on the alignment microwell array and the desired location if the distance is greater than a predetermined threshold value; and (f) repeating steps (b)-(e) until the distance between the alignment droplet's location on the alignment microwell array and the desired location is no more than the predetermined threshold value. In some embodiments, the first imaging sensor and the second imaging sensor can be approximately orthogonal to each other. In some embodiments, the first and the second imaging sensors can be located between a waste receiving vessel and the alignment microwell array. In some embodiments, depositing the alignment droplet into the microwell of the alignment microwell array can comprise moving a stage, for example the stage 350, holding the microwell array to, for example, a desired stage position based on the desired location.

Figure 5A:
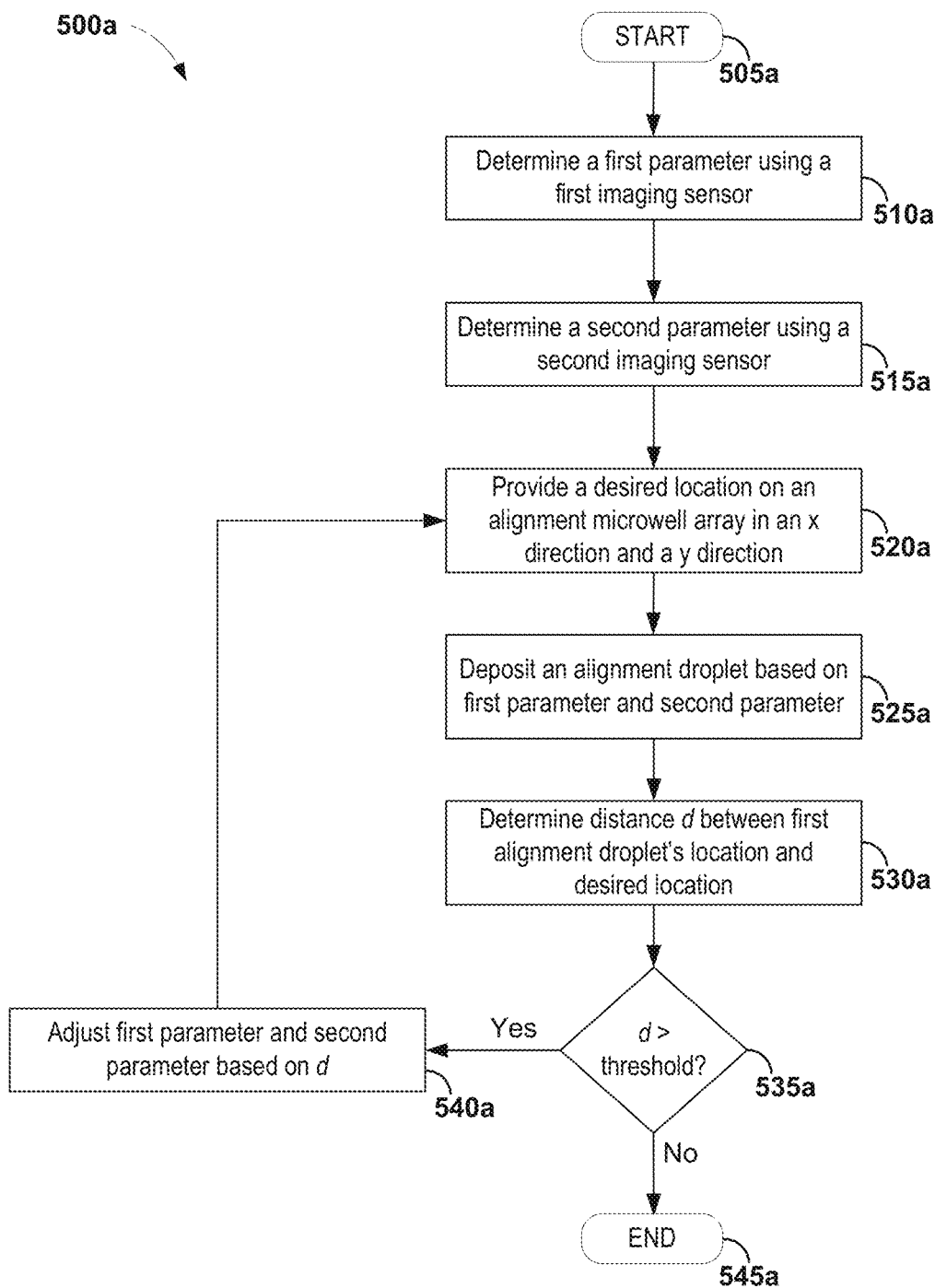
FIGS. 5A-5B are flowcharts showing non-limiting exemplary workflows for aligning a microwell array, for example an alignment microwell array.

FIG. 5A is flowchart showing a non-limiting exemplary workflow 500*a* for aligning a microwell array, for example the alignment microwell array 338*a*, positioned on a stage of a sorting device, for example the stage 350 of the sorting device 300. In some embodiments, the alignment controller 418 can perform the workflow 500*a*. After the workflow 500*a* begins at 505*a*, a first parameter can be determined using a first imaging sensor, for example the imaging sensor 302*a*, at 510*a*. A second parameter can be determined using a second imaging sensor, for example the imaging sensor 302*b*, at 515*a*. In some embodiments, the first imaging sensor and the second imaging sensor can be approximately orthogonal to each other. In some embodiments, the first and the second imaging sensors can be located between a waste receiving vessel, for example the waste receiving vessel 238*a*, and the alignment microwell array.

At 520*a*, a desired location on an alignment microwell array, for example the microwell 340*a* of the alignment microwell array 338*a*, in an x direction and a y direction can be provided. In some embodiments, providing the desired location in the x direction on the alignment microwell array can comprise using the first imaging sensor to determine the desired location in the x direction on the alignment microwell array and providing the desired location in the y direction on the alignment microwell array can comprise using the second imaging sensor to determine the desired location in the y direction on the sample array.

Based on the first parameter and the second parameter, at 525*a* the sorting device 300 can be instructed to deposit an alignment droplet, for example the alignment droplet 230*d*, into a microwell of the alignment microwell array, for example the microwell 340*a*. In some embodiments, the alignment controller 418 can instruct the sorting device 300 to deposit the alignment droplet by communicating with one or more of the flow controller 214, detection analyzer 226, and the deflection controller 228. In some embodiments, depositing the alignment droplet into the microwell of the alignment microwell array can comprise moving a stage, for example the stage 350, holding the microwell array to, for example, a desired stage position based on the desired location.

At 530*a*, the distance d between the alignment droplet's location on the alignment microwell array and the desired location can be determined. In some embodiments, the alignment controller 418 can determine the distance d based on the images of the alignment droplet captured by the first imaging sensor and the second imaging sensor. At 535*a*, if the distance d is greater than a threshold, for example a predetermined threshold, the first parameter and the second parameter are adjusted based on the distance d.

The threshold can vary. In some embodiments, the threshold can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 nanometers, or a number or a range between any two of these values. In some embodiments, the threshold can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 nanometers. In some embodiments, the threshold can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the threshold can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 micrometers. In some embodiments, the threshold can be, or be about, 1%, 2%, 3%, 4%, 5%, 6%, 7%, 8%, 9%, 10%, 20%, 30%, 40%, 50%, 60%, 70%, 80%, 90%, 99%, 99.9%, 100%, or a number or a range between any two of these values, of the microwell diameter. In some embodiments, the threshold can be at least, or at most, 1%, 2%, 3%, 4%, 5%, 6%, 7%, 8%, 9%, 10%, 20%, 30%, 40%, 50%, 60%, 70%, 80%, 90%, 99%, 99.9%, or 100%, of the microwell diameter. In some embodiments, the threshold can be, or be about, 1%, 2%, 3%, 4%, 5%, 6%, 7%, 8%, 9%, 10%, 20%, 30%, 40%, 50%, 60%, 70%, 80%, 90%, 99%, 99.9%, 100%, or a number or a range between any two of these values, of the distance or the spacing between the edges of the microwells. In some embodiments, the threshold can be at least, or at most, 1%, 2%, 3%, 4%, 5%, 6%, 7%, 8%, 9%, 10%, 20%, 30%, 40%, 50%, 60%, 70%, 80%, 90%, 99%, 99.9%, or 100%, of the distance or the spacing between the edges of the microwells.

In some embodiments, depositing the first alignment droplet into the microwell of the first alignment microwell array comprises: depositing the first alignment droplet into an alignment device of the first alignment microwell array, and wherein determining the distance between the first alignment droplet's location on the first alignment microwell array and the desired location comprises imaging the alignment device and the first alignment droplet on the alignment device using the first imaging sensor and imaging the alignment device and the first alignment droplet on the alignment device using the second imaging sensor.

In some embodiments, the alignment device comprises a plurality of alignment regions. Two alignment regions of the plurality of alignment regions can comprise approximately equal areas. The plurality of alignment regions can comprise a plurality of concentric rings. Two concentric rings of the concentric rings can be separated from each other by, or about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1 mm, or a number or range between any two of these values. Two concentric rings of the concentric rings can be separated from each other by at least, or at most 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1 mm, or more or less.

Steps 520*a*, 525*a*, and 530*a* can be repeated until the distance d is not greater than a threshold. For example, at 520*a*, an updated desired location, for example the microwell 340*b*, can be provided. Based on the adjusted first parameter and the adjusted second parameter and/or the new desired location, at 525*a* the sorting device 300 can be instructed to deposit another alignment droplet, for example the alignment droplet 230*c*, into a microwell of the alignment microwell array, for example the microwell 340*b*. In some embodiments, all the alignment droplets can be deposited into different microwells of the alignment microwell array. In some embodiments, some or all of the alignment droplets can be deposited into different microwells of the microwell array. At 530*a*, the distance d between the location of the most recently deposited alignment droplet on the alignment microwell array and the updated desired location can be determined. If the distance d is not greater than a threshold, the workflow 500*a* ends at 545*a*.

The first parameter and the second parameter can be related to one or more of the desired location in the x direction and the desired location in the y direction. In some embodiments, the first parameter can be related to the desired location in the x direction, and the second parameter can be related to the desired location in the y direction.

The distance between an alignment droplet's location on the alignment microwell and its desired location can be determined using a number of methods. In some embodiments, determining the distance between an alignment droplet's location on the alignment microwell array and the desired location can comprise imaging the alignment microwell array and the alignment droplet using the first imaging sensor. In some embodiments, determining the distance between an alignment droplet's location on the alignment microwell array and the desired location can comprise imaging the alignment microwell array and the alignment droplet using the second imaging sensor.

The first parameter and the second parameter can be related to a number of characteristics. In some embodiments, the first parameter can be related to drop charge. In some embodiments, the first parameter can related to the x direction. In some embodiments, the first parameter can related to the y direction. In some embodiments, the first parameter can related to the x direction and the y direction. In some embodiments, the second parameter can be related to drop charge. In some embodiments, the second parameter can related to the x direction. In some embodiments, the second parameter can related to the y direction. In some embodiments, the first parameter can related to the x direction and the y direction.

The first parameter and the second parameter can be adjusted using a number of methods. In some embodiments, adjusting the first parameter based on the distance between an alignment droplet's location on the alignment microwell array and the desired location can comprise determining the alignment droplet's location on the alignment microwell array by imaging the alignment microwell array and the alignment droplet by the first imaging sensor. In some embodiments, adjusting the first parameter based on the distance between an alignment droplet's location on the alignment microwell array and the desired location can comprise determining the alignment droplet's location on the alignment microwell array by imaging the alignment microwell array and the alignment droplet by the first imaging sensor and the second imaging sensor. In some embodiments, adjusting the second parameter based on the distance between an alignment droplet's location on the alignment microwell array and the desired location can comprise determining the alignment droplet's location on the alignment microwell array by imaging the alignment microwell array and the alignment droplet by the second imaging sensor. In some embodiments, adjusting the second parameter based on the distance between an alignment droplet's location on the alignment microwell array and the desired location can comprise determining the alignment droplet's location on the alignment microwell array by imaging the alignment microwell array and the alignment droplet using the first imaging sensor and the second imaging sensor.

Alignment droplets can be deposited into one or more microwells of the alignment microwell arrays using a number of methods. In some embodiments, depositing an alignment droplet into a microwell of the alignment microwell array can comprise flow cytometrically depositing the alignment droplet into the microwell of the alignment microwell array.

The threshold, for example the predetermined threshold, can correlate to a number of parameters. In some embodiments, the threshold value can correlate to an alignment droplet's distance from an edge of the waste receiving vessel. In some embodiments, the threshold value can correlate to an alignment droplet's distance from one or more edges of the waste receiving vessel.

Disclosed herein are methods for aligning alignment microwell arrays, for example a first alignment microwell array, for producing sample microwell arrays. In some embodiments, the methods can comprise: (a) determining a $n^{th}$ parameter pair (parameter$_{x,n}$; parameter$_{y,n}$), wherein the parameter$_{x,1}$ is determined using a first imaging sensor and the parameter$_{y,1}$ is determined using a second imaging sensor; (a) providing a $n^{th}$ desired location ($x_{desired,n}$; $y_{desired,n}$, wherein the $x_{desired,n}$ is in an x direction on an alignment well array and the $y_{desired,n}$ is in a y direction on the alignment well array; (c) depositing a $n^{th}$ alignment droplet into a $n^{th}$ microwell of the alignment microwell array based on the $n^{th}$ parameter pair (parameter$_{x,n}$; parameter$_{y,n}$), wherein the parameter$_{x,n}$ is related to the $x_{desired}$ and the parameter is related to the $y_{desired}$; (d) determining the distance between the $n^{th}$ alignment droplet's location ($x_n$; $y_n$) on the alignment well array and the desired location ($x_{desired,n}$; $y_{desired,n}$) using the first imaging sensor for the $x_n$ and the second imaging sensor for the $y_n$; (e) determining a $n+1^{th}$ parameter pair (parameter$_{x,n+1}$; parameter$_{y,n+1}$) for a $(n+1)^{th}$ alignment droplet based on the distance between the $n^{th}$ alignment droplet's location ($x_n$; $y_n$) on the alignment well array and the desired location ($x_{desired,n}$; $y_{desired,n}$) if the distance is greater than a predetermined threshold ($x_{threshold}$; $y_{threshold}$); and (f) repeating the steps (b)-(e) until the distance between a $m^{th}$ alignment droplet's location ($x_m$; $y_m$) on the alignment well array and the desired location ($x_{desired,m}$; $y_{desired,m}$) is within the predetermined threshold ($x_{threshold}$; $y_{threshold}$). In some embodiments, the first imaging sensor and the second imaging sensor can be approximately orthogonal to each other and can be located between a waste receiving vessel and the alignment well array. In some embodiments, depositing the $n^{th}$ alignment droplet into the $n^{th}$ microwell of the alignment microwell array can comprise moving a stage holding the alignment microwell array to, for example, a $n^{th}$ desired stage location ($x_{stage\ desired,n}$; $y_{stage\ desired,n}$) based on the $n^{th}$ desired location ($x_{desired,n}$; $y_{desired,n}$).

The predetermined threshold can vary. In some embodiments, the $x_{threshold}$ or the $y_{threshold}$ can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 nanometers, or a number or a range between any two of these values. In some embodiments, the $x_{threshold}$ or the $y_{threshold}$ can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 nanometers. In some embodiments, the $x_{threshold}$ or the $y_{threshold}$ can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the $x_{threshold}$ or the $y_{threshold}$ can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 micrometers. In some embodiments, the $x_{threshold}$ or the $y_{threshold}$ can be, or be about, 1%, 2%, 3%, 4%, 5%, 6%, 7%, 8%, 9%, 10%, 20%, 30%, 40%, 50%, 60%, 70%, 80%, 90%, 99%, 99.9%, 100%, or a number or a range between any two of these values, of the microwell diameter. In some embodiments, the $x_{threshold}$ or the $y_{threshold}$ can be at least, or at most, 1%, 2%, 3%, 4%, 5%, 6%, 7%, 8%, 9%, 10%, 20%, 30%, 40%, 50%, 60%, 70%, 80%, 90%, 99%, 99.9%, or 100%, of the microwell diameter. In some embodiments, the $x_{threshold}$ or the $y_{threshold}$ can be, or be about, 1%, 2%, 3%, 4%, 5%, 6%, 7%, 8%, 9%, 10%, 20%, 30%, 40%, 50%, 60%, 70%, 80%, 90%, 99%, 99.9%, 100%, or a number or a range between any two of these values, of the distance or the spacing between the edges of the microwells. In some embodiments, the $x_{threshold}$ or the $y_{threshold}$ can be at least, or at most, 1%, 2%, 3%, 4%, 5%, 6%, 7%, 8%, 9%, 10%, 20%, 30%, 40%, 50%, 60%, 70%, 80%, 90%, 99%, 99.9%, or 100%, of the distance or the spacing between the edges of the microwells.

Figure 5B:
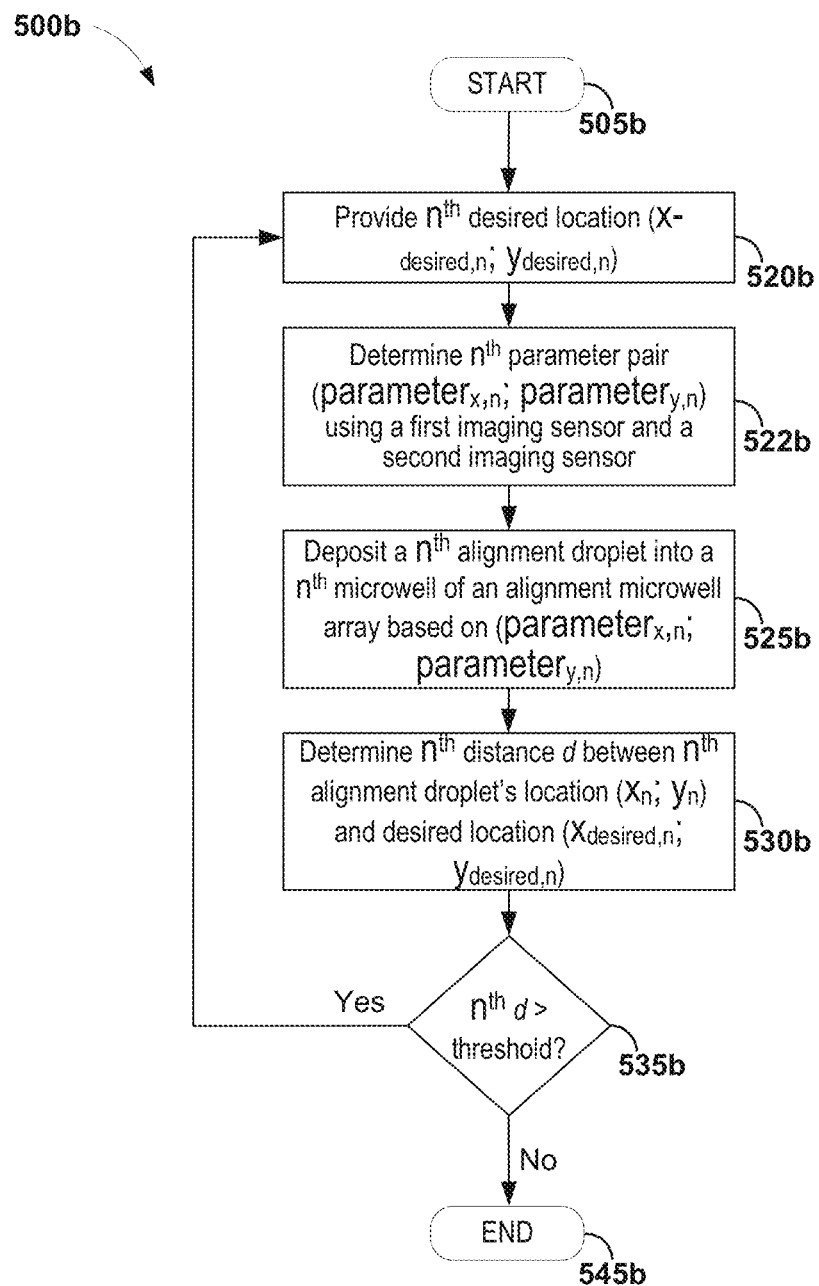

FIG. 5B is flowchart showing a non-limiting exemplary workflow 500b for aligning a microwell array, for example the alignment microwell array 338a, positioned on a stage of a sorting device, for example the stage 350 of the sorting device 300. In some embodiments, the alignment controller 418 can perform the workflow 500b. After the workflow 500b begins at 505b, at 520b a $n^{th}$ desired location ($x_{desired,n}$; $y_{desired,n}$) on an alignment microwell array, for example the microwell 340a of the alignment microwell array 338a, in an x direction and a y direction can be provided. In some embodiments, providing the $n^{th}$ desired location ($x_{desired,n}$; $y_{desired,n}$) in the x direction on the alignment microwell array can comprise using the first imaging sensor to determine the $x_{desired,n}$ and providing the $n^{th}$ desired location ($x_{desired}$; $y_{desired}$) in the y direction on the alignment well array comprises using the second imaging sensor to determine the $y_{desired,n}$.

At step 522b, $n^{th}$ parameter pair (parameter$_{x,n}$; parameter$_{y,n}$) can be determined using a first imaging sensor, for example the imaging sensor 302a and a second imaging sensor, for example the imaging sensor 302b. In some embodiments, the parameter$_{x,n}$ can be determined by the first imaging sensor and not the second imaging sensor. In some embodiments, the parameter$_{x,n}$ can be determined by the second imaging sensor and not the first imaging sensor. In some embodiments, the parameter$_{x,n}$ can be determined by the first imaging sensor and the second imaging sensor. In some embodiments, the parameter$_{y,n}$ can be determined by the first imaging sensor and not the second imaging sensor. In some embodiments, the parameter$_{y,n}$ can be determined by the second imaging sensor and not the first imaging sensor. In some embodiments, the parameter$_{y,n}$ can be determined by the first imaging sensor and the second imaging sensor. In some embodiments, the first imaging sensor and the second imaging sensor can be approximately orthogonal to each other. In some embodiments, the first and the second imaging sensors can be located between a waste receiving vessel, for example the waste receiving vessel 238a, and the alignment microwell array.

Based on the $n^{th}$ parameter pair (parameter$_{x,n}$; parameter$_{y,n}$), at 525b the sorting device 300 can be instructed to deposit a $n^{th}$ alignment droplet, for example the alignment droplet 230d, into a microwell of the alignment microwell array, for example the microwell 340a. In some embodiments, the alignment controller 418 can instruct the sorting device 300 to deposit the alignment droplet by communicating with one or more of the flow controller 214, detection analyzer 226, and the deflection controller 228. In some embodiments, depositing the $n^{th}$ alignment droplet into the $n^{th}$ microwell of the alignment microwell array can comprise moving a stage holding the alignment microwell array to, for example, a $n^{th}$ desired stage location ($x_{stage\ desired,n}$; $y_{stage\ desired,n}$) based on the $n^{th}$ desired location ($x_{desired,n}$; $y_{desired,n}$).

At 530b, the $n^{th}$ distance d between the $n^{th}$ alignment droplet's location on the alignment microwell array ($x_n$; $y_n$) and the desired location ($x_{desired,n}$; $y_{desired,n}$) can be determined. In some embodiments, the alignment controller 418 can determine the distance d based on the images of the alignment droplet captured by the first imaging sensor and the second imaging sensor.

At 535b, if the $n^{th}$ distance d is greater than a threshold, for example a predetermined threshold, the steps 520b, 522b, 525b, and 530b can be repeated until the $n^{th}$ distance d is not greater than a threshold. For example, at step 520b, an n+1$^{th}$ desired location ($x_{desired,n+1}$; $y_{desired,n+1}$), for example the microwell 340b, can be provided. At 522b, a n+1$^{th}$ parameter pair (parameter$_{x,n+1}$; parameter$_{y,n+1}$) can be determined using a first imaging sensor and a second imaging sensor.

The threshold can vary. In some embodiments, the threshold can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 nanometers, or a number or a range between any two of these values. In some embodiments, the threshold can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 nanometers. In some embodiments, the threshold can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the threshold can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 micrometers. In some embodiments, the threshold can be, or be about, 1%, 2%, 3%, 4%, 5%, 6%, 7%, 8%, 9%, 10%, 20%, 30%, 40%, 50%, 60%, 70%, 80%, 90%, 99%, 99.9%, 100%, or a number or a range between any two of these values, of the microwell diameter. In some embodiments, the threshold can be at least, or at most, 1%, 2%, 3%, 4%, 5%, 6%, 7%, 8%, 9%, 10%, 20%, 30%, 40%, 50%, 60%, 70%, 80%, 90%, 99%, 99.9%, or 100%, of the microwell diameter. In some embodiments, the threshold can be, or be about, 1%, 2%, 3%, 4%, 5%, 6%, 7%, 8%, 9%, 10%, 20%, 30%, 40%, 50%, 60%, 70%, 80%, 90%, 99%, 99.9%, 100%, or a number or a range between any two of these values, of the distance or the spacing between the edges of the microwells. In some embodiments, the threshold can be at least, or at most, 1%, 2%, 3%, 4%, 5%, 6%, 7%, 8%, 9%, 10%, 20%, 30%, 40%, 50%, 60%, 70%, 80%, 90%, 99%, 99.9%, or 100%, of the distance or the spacing between the edges of the microwells.

Based on the n+1$^{th}$ parameter pair (parameter$_{x,n+1}$; parameter$_{y,n+1}$) and/or the n+1$^{th}$ desired location ($x_{desired,n+1}$; $y_{desired,n+1}$), at 525b the sorting device 300 can be instructed to deposit a n+1$^{th}$ alignment droplet, for example the alignment droplet 230c, into a microwell of the alignment microwell array, for example the microwell 340b. At 530b, the n+1$^{th}$ distance d between the n+1$^{th}$ alignment droplet's location on the alignment microwell array ($x_{n+1}$; $y_{n+1}$) and the desired location ($x_{desired,n+1}$; $y_{desired,n+1}$) can be determined. If the n+1$^{th}$ distance d is not greater than a threshold, the workflow 500b ends at 545b.

In some embodiments, depositing the $n^{th}$ alignment droplet can comprise flow cytometrically depositing the $n^{th}$ alignment droplet into the microwell of the alignment microwell array.

Stream Alignment Method

Aspects of the disclosure also include methods for adjusting a flow stream 402 of a flow cytometer. Methods according to certain embodiments include capturing one or more images 406 of a flow stream of the flow cytometer in a detection field; determining one or more properties of the flow stream 402 in the detection field, generating a data signal corresponding to the one or more properties of the flow stream 402 and adjusting one or more parameters of the flow cytometer in response to the data signal. Methods also include automatically adjusting one or more parameters of the flow cytometer in response to data signals derived from captured images, such as adjusting stream placement. The subject methods can be fully automated, such that adjustments are made in response to data signals corresponding to one or more parameters of the flow stream with little, if any, human intervention or manual input by the user.

In some embodiments, the method comprises: (a) receiving a first parameter used to deposit a first alignment droplet to a desired location on a first alignment microwell array; (b) depositing a second alignment droplet to a second alignment microwell array using the first parameter; (c) determining a path of the second alignment droplet, from a cell sorting component to the second alignment microwell, in the first detection field using a first imaging sensor, wherein the first imaging sensor is located between the cell sorting component and a waste receiving vessel; and (d) determining a first measurement between a first position of a path of the first alignment droplet in the first detection field and a corresponding first position of the path of the second droplet in the first detection field.

In some embodiments, the method comprise: (e) if the first measurement is greater than a first predetermined threshold: adjusting the first parameter based on the first measurement; and repeating steps (b)-(d). In some embodiments, wherein receiving the first parameter used to deposit the first alignment droplet to the first desired location on the first alignment microwell array comprises: depositing the first alignment droplet to the desired location on the first alignment microwell array using the first parameter; and determining the path of the first alignment droplet in the first detection field using the first imaging sensor.

In some embodiments, the first parameter can be related to the desired location in the x direction. The first parameter can be related to droplet charge. In some embodiments, the second parameter can be related to the desired location in the y direction. The second parameter can be related to droplet charge.

In some embodiments, depositing the first alignment droplet to the desired location on the first alignment microwell array using the first parameter comprises: depositing the first alignment droplet to the desired location on the first alignment microwell array using the first parameter and a second parameter. Depositing the second alignment droplet to the second alignment microwell array using the first parameter can comprise: depositing the second alignment droplet to the second alignment microwell array using the first parameter and the second parameter.

In some embodiments, the step (b) can comprise: determining a path of the first alignment droplet in a second detection field, using a second imaging sensor, from the deflection plate to the desired location on the first alignment microwell array, wherein the second imaging sensor is located between the waste receiving vessel and the deflection plate. The step (c) can comprise: determining a path of the second alignment droplet in the second detection field using the second imaging sensor. The step (d) can comprise: determining a second measurement between a second position of the path of the first alignment droplet in the second detection field and a corresponding second position of the path of the second droplet in the second detection field. The step (f) can comprise: if the second measurement is greater than a second predetermined threshold, adjusting the second parameter based on the second measurement. In some embodiments, the first imaging sensor and the second imaging sensor are approximately orthogonal to each other.

In some embodiments, determining the path of the first alignment droplet in the first detection field can comprise capturing a first alignment image of the first alignment droplet in the first detection field. Determining the path of the second alignment droplet in the first detection field can comprise capturing a second alignment image of the second alignment droplet in the first detection field. Determining the path of the first alignment droplet in the first detection field can comprise determining a first channel, in the first alignment image, along the path of the first alignment droplet in the first detection field. The first measurement can comprise whether at least a part of the path of the second alignment droplet in the first detection field is within a corresponding first channel in the second alignment image.

In some embodiments, the first channel can be represented by two bars in the first alignment image, and wherein the corresponding first channel is represented by corresponding two bars in the second alignment image. The first measurement can comprise a first distance between the first position of the path of the first alignment droplet in the first detection field and the corresponding first position of the path of the second droplet in the first detection field.

In some embodiments, determining the path of the first alignment droplet in the second detection field can comprise capturing a third alignment image of the first alignment droplet in the second detection field. Determining the path of the second alignment droplet in the second detection field can comprise capturing a fourth alignment image of the second alignment droplet in the second detection field. Determining the path of the first alignment droplet in the second detection field can comprise determining a second channel, in the third alignment image, along the path of the first alignment droplet in the second detection field. The second measurement can comprise whether at least a part of the path of the second alignment droplet in the first detection field is within a corresponding second channel in the second alignment image.

In some embodiments, the second channel can be represented by two bars in the third alignment image, and wherein the corresponding second channel is represented by corresponding two bars in the fourth alignment image. The second measurement can comprise a second distance between the second position of the path of the first alignment droplet in the second detection field and the corresponding second position of the path of the second droplet in the first detection field.

In some embodiments, depositing the first alignment droplet to the desired location of the first alignment microwell array can comprise flow cytometrically depositing the first alignment droplet to the desired location of the first alignment microwell array. Depositing the second droplet using the first parameter can comprise flow cytometrically depositing the second using the first parameter.

In some embodiments, the method can comprise: introducing a sample droplet into a microwell of the sample microwell array based on the first parameter. The method can comprise: introducing a plurality of sample droplets into a plurality of microwells of the sample microwell array based on the adjusted first parameter. The plurality of sample droplets can comprise cells, particles attached with oligonucleotide barcodes, or any combination thereof.

Plate sorting refers to outputting sample drops onto any output device that can contain more than one destination for droplets. The droplets can be sub-millimeter in size and deposited accurately into multiple destinations. The destination surface can be a two-dimensional surface of various dimensions ranging from small slides up to 384-well capacities.

Placement of the drops requires high precision and therefore the sorter output stage motors can be calibrated in both the x-y directions to compensate for various mechanical tolerances. This calibration is tedious, time-consuming, and requires repeated steps to get the accuracy high enough to use the device.

Typical calibration consists of several iterations of depositing a drop onto the surface and observing where it 'lands.' Then the user sets the necessary offsets in millimeters in both x and y directions into the instrument and repeats the process. This is a trial-and-error process that typically requires several iterations until the drop is deposited in the center of the desired location.

Instead of simply guessing the required x/y offset needed to align the output device, a much faster technique can be devised. By using a calibrated target device for output and a software application that can do the x/y calculation, the calibration can be down with one iteration.

Computer System

In embodiments, the processors include memory having a plurality of instructions for performing the steps of the subject methods (as described herein), such as illuminating a flow cytometer flow stream in a detection field with a light source, capturing one or more images of the flow stream, generating a data signal corresponding to one or more properties of the flow stream based on the captured images, and adjusting parameters of the flow stream in response to the data signal. The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Figure 6:
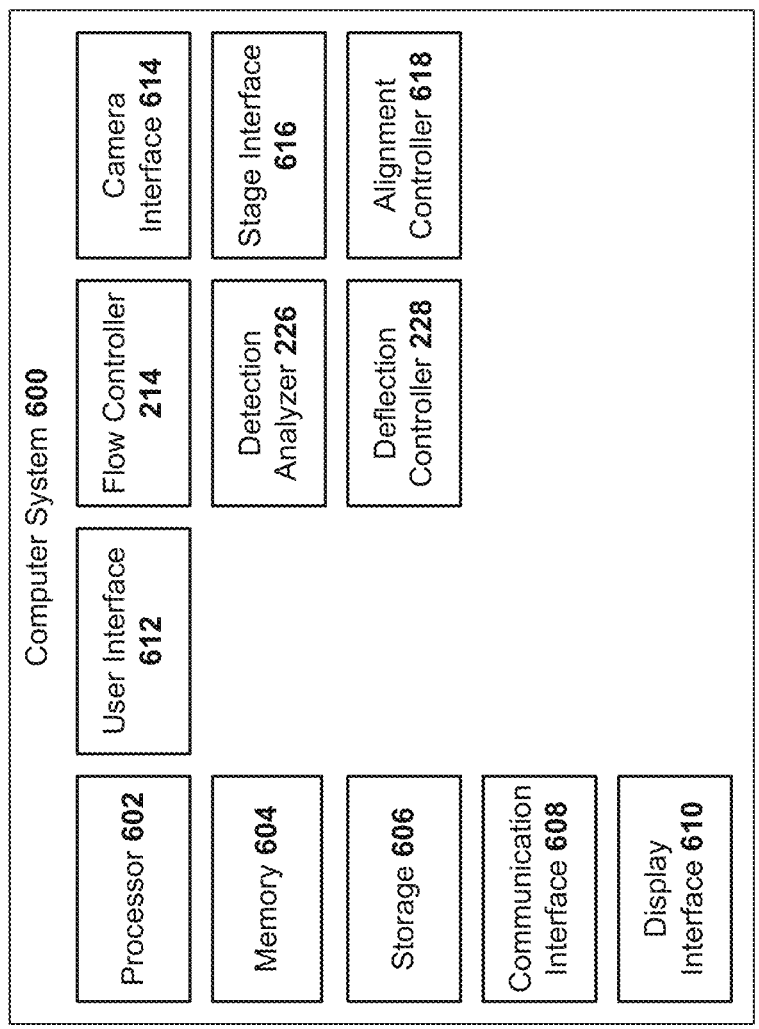
FIG. 6 is a non-limiting exemplary block diagram of a cell sorter computer system for controlling a sorting device.

FIG. 6 is a non-limiting exemplary block diagram of a cell sorter computer system 600 for controlling a sorting device, for example the sorting device 300. As illustrated, the computer system 600 can include a processor 602 that is in electrical communication with a memory 604, a storage 66, a communication interface 608, and a display interface 610. The memory 604 can store instructions to configure the processor 602 to perform the functions of the computer system 600 when the computer system 600 is powered on. For example, the instructions stored in the memory 604 can configure the processor 602 to perform the functions of the flow controller 214, the detection analyzer 226, and the deflection controller 228. When the computer system 600 is powered off, the storage 606 can store the instructions for configuring the processor 602 to perform the functions of the computer system 600.

In some embodiments, the processor 602 includes memory having instructions stored thereon for performing the steps of the subject methods including illuminating a flow cytometer flow stream in a detection field with a light source, capturing one or more images of the flow stream, generating a data signal corresponding to one or more properties of the flow stream based on the captured images, and adjusting parameters of the flow stream in response to the data signal.

The communication interface 608 can facilitate the communications between the 600 and other devices connected to computer system, for example the sorting device 300. The display interface 610. The display interface 610, together with a user interface 612, can facilitate the interactions between the sorting device 300 and its users by, for example, displaying information regarding sample sorting and device setup to the users.

The computer system 600 can include a camera interface 614 and a stage interface 416 in electrical communication with the processor 602. The camera interface 614 can receive images captured by the alignment imaging sensors 302a and 302b. Based on the images captured by the alignment imaging sensors 302a and 302b, an alignment controller 418 of the computer system can 600 can align a microwell array, for example the alignment microwell array 338a, by moving the stage 350 that can be in communication with the stage interface 416.

Aspects of the present disclosure further include computer controlled systems for practicing the subject methods, where the systems further include one or more computers for complete automation or partial automation of a system for practicing methods described herein. In some embodiments, systems include a computer having a computer readable storage medium with a computer program stored thereon, where the computer program when loaded on the computer includes instructions for capturing one or more images of a flow stream of the flow cytometer in a detection field; algorithm for determining the spatial position of the flow stream in the detection field; algorithm for generating a data signal corresponding to the spatial position of the flow stream; and instructions for adjusting one or more parameters of the flow cytometer in response to the data signal. In certain instances, systems include a computer having a computer readable storage medium with a computer program stored thereon, where the computer program when loaded on the computer includes instructions for capturing one or more images of a flow stream of the flow cytometer in a detection field; algorithm for determining the physical dimensions of the flow stream in the detection field; algorithm for generating a data signal corresponding to the physical dimensions of the flow stream; and instructions for adjusting one or more parameters of the flow cytometer in response to the data signal.

In embodiments, the system includes an input module, a processing module and an output module. Processing modules of interest may include one or more processors that are configured and automated to adjust one or more parameters of a flow cytometer as described above. For example processing modules may include two or more processors that are configured and automated to adjust one or more parameters of a flow cytometer as described above, such as three or more processors, such as four or more processors and including five or more processors.

In some embodiments, the subject systems may include an input module such that parameters or information about the fluidic sample, sheath fluid pressure, hydrostatic pressure, flow stream charge, deflection voltage, charge correction value, drop delay, drop drive frequency, drop amplitude and charge phase, flow cell nozzle orifice, position of support stages, imaging sensors, light sources, optical adjustment protocols, amplifiers as well as properties, resolution and sensitivity of imaging sensors may be input before practicing the subject methods.

As described here, each processor can include memory having a plurality of instructions for performing the steps of the subject methods, such as capturing one or more images of a flow stream of the flow cytometer in a detection field; determining one or more properties of the flow stream in the detection field; generating a data signal corresponding to the one or more properties of the flow stream; and adjusting one or more parameters of the flow cytometer in response to the data signal. After the processor has performed one or more of the steps of the subject methods, the processor may be automated to make adjustments to parameters of the flow cytometer, such as adjustments as described above.

The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Systems may include a display and operator input device. Operator input devices may, for example, be a keyboard, mouse, or the like. The processing module includes a processor which has access to a memory having instructions stored thereon for performing the steps of the subject methods. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the embodiments disclosed herein also include programming, e.g., in the form of computer program products, algorithms for use in practicing the methods as described above. Programming according to the present disclosure can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a a computer connected to a Wide Area Network ("WAN"), telephone network, satellite network, or any other suitable communication channel, including a mobile telephone (i.e., smartphone).

In some embodiments, systems according to the present disclosure may be configured to include a communication interface. In some embodiments, the communication interface includes a receiver and/or transmitter for communicating with a network and/or another device. The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the subject systems and other external devices such as a computer terminal (for example, at a physician's office or in hospital environment) that is configured for similar complementary data communication.

In one embodiment, the communication interface is configured for infrared communication, Bluetooth® communication, or any other suitable wireless communication protocol to enable the subject systems to communicate with other devices such as computer terminals and/or networks, communication enabled mobile telephones, personal digital assistants, or any other communication devices which the user may use in conjunction.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the subject systems are configured to wirelessly communicate with a server device via the communication interface, e.g., using a common standard such as 802.11 or Bluetooth® RF protocol, or an IrDA infrared protocol. The server device may be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen.

In some embodiments, the communication interface is configured to automatically or semi-automatically communicate data stored in the subject systems, e.g., in an optional data storage unit, with a network or server device using one or more of the communication protocols and/or mechanisms described above.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT□, Windows XP, Windows 7, Windows 8, iOS, Sun Solaris, Linux, OS/400, Compaq Tru64 Unix, SGI IRIX, Siemens Reliant Unix, and others.

Imaging Sensors

The imaging sensors can be any suitable device capable of capturing and converting an optical image into an electronic data signal. Non-limiting exemplary imaging sensors include charge-coupled devices, semiconductor charge-coupled devices (CCD), active pixel sensors (APS), complementary metal-oxide semiconductor (CMOS) image sensors, and N-type metal-oxide semiconductor (NMOS) image sensors. In some embodiments, an imaging sensor can be a CCD camera. The CCD camera can be an electron multiplying CCD (EMCCD) camera or an intensified CCD (ICCD) camera. In some embodiments, the imaging sensor can be a CMOS camera.

Systems include one or more imaging sensors configured to capture images of a flow stream in a detection field. The imaging sensor may be any suitable device capable of capturing and converting an optical image into an electronic data signal, including but not limited to charge-coupled devices, semiconductor charge-coupled devices (CCD), active pixel sensors (APS), complementary metal-oxide semiconductor (CMOS) image sensors or N-type metal-oxide semiconductor (NMOS) image sensors. In some embodiments, the imaging sensor is a CCD camera. For example, the camera may be an electron multiplying CCD (EMCCD) camera or an intensified CCD (ICCD) camera. In other embodiments, the imaging sensor is a CMOS-type camera.

Depending on the number of detection fields being interrogated and flow cytometer parameters of interest, the number of imaging sensors in the subject systems may vary, as desired. For example, the subject systems may include one imaging sensor or more, such as two imaging sensors or more, such as three imaging sensors or more, such as four imaging sensors or more, such as five imaging sensors or more and including ten imaging sensors or more. In certain embodiments, systems include one imaging sensor. In other embodiments, systems include two imaging sensors. Where systems include more than one imaging sensor, each imaging sensors may be oriented with respect to the other (as referenced in an X-Y plane) at an angle ranging from 10° to 90°, such as from 15° to 85°, such as from 20° to 80°, such as from 25° to 75° and including from 30° to 60°. In certain embodiments, each imaging sensor is oriented orthogonally (as referenced in an X-Y plane) to each other. For example, where the subject systems include two imaging sensors, the first imaging sensor is oriented orthogonally (as referenced in an X-Y plane) to the second imaging sensor.

Where the subject systems include more than one imaging sensor, each imaging sensor may be the same or a combination of sensors. For example, where the subject systems include two imaging sensors, in some embodiments the first imaging sensor is a CCD-type device and the second imaging sensor is a CMOS-type device. In other embodiments, both the first and second imaging sensor are CCD-type devices. In yet other embodiments, both the first and second imaging sensors are CMOS-type devices.

In some embodiments, the imaging sensors are stationary, maintaining a single position within the flow cytometer. In other embodiments, the imaging sensors may be configured to move along the path of the flow stream. For instance, the imaging sensor may be configured to move upstream and downstream alongside the flow stream capturing images in a plurality of detection fields. For example, systems may include an imaging sensor which is adapted to capture images in two or more different detection fields along the flow stream, such as 3 or more detection fields, such as 4 or more detection fields and including 5 or more detections fields. Where the imaging sensor is configured to move along the flow stream, the imaging sensor may be moved along the flow stream path continuously or in discrete intervals. In some embodiments, the imaging sensor is displaced continuously. In other embodiments, the imaging sensor may be displaced along the flow stream path in discrete intervals, such as for example in 1 mm or greater increments, such as 2 mm or greater increments and including 5 mm or greater increments.

Where the imaging sensor is configured to capture images at different positions along a path of the flow stream, the imaging sensor may be configured to capture images continuously or in discrete intervals. In some embodiments, imaging sensors of interest are configured to capture images continuously. In other instances, imaging sensors are configured to take measurements in discrete intervals, such as capturing an image of the flow stream every 0.001 millisecond, every 0.01 millisecond, every 0.1 millisecond, every 1 millisecond, every 10 milliseconds, every 100 milliseconds and including every 1000 milliseconds, or some other interval.

In some embodiments, the imaging sensor is configured to capture one or more images of the flow stream in each detection field. For example, the imaging sensor may be configured to capture 2 or more images of the flow stream in each detection field, such as 3 or more images, such as 4 or more images, such as 5 or more images, such as 10 or more images, such as 15 or more images and including 25 or more images. Where a plurality of images are captured in a detection field, the processor (as disclosed herein) can include digital imaging processing algorithm for stitching together the plurality of images.

Depending on the flow stream rate and desired image resolution, the imaging sensor may have an exposure time of 100 ms or less when reading out the full sensor, such as 75 ms or less, such as 50 ms or less, such as 25 ms or less, such 10 ms or less, such as 5 ms or less, such as 1 ms or less, such as 0.1 ms or less such as 0.01 ms or less, such as 0.001 ms or less, such as 0.0001 ms or less, such as 0.00001 ms or less and including an exposure time of 0.000001 ms or less. For example, the exposure time of the imaging sensor in a detection field which captures images of the flow stream at the flow cell nozzle orifice may have an exposure time which ranges from 0.0001 ms to 10 ms, such as from 0.001 ms to 5 ms, such as from 0.01 ms to 2 ms and including from 0.1 ms to 1 ms. The exposure time of imaging sensors in a detection field which captures images of the flow cytometer flow stream downstream from the nozzle orifice may have an exposure time which ranges from 0.0001 ms to 10 ms, such as from 0.001 ms to 5 ms, such as from 0.01 ms to 2 ms and including from 0.1 ms to 1 ms.

In certain embodiments, imaging sensors in the subject systems may have 1M active pixels or more, such as 1.5M or more, e.g., 2M or more, 2.5M or more, or 3M or more. In certain aspects, a pixel corresponds to an actual physical dimension of about 0.3 μm. Depending on the detection field, in some embodiments, imaging sensors have a sensor area of 150 mm$^2$ or more, such as about 150 mm$^2$ to about 175 mm$^2$, about 175 mm$^2$ to about 200 mm$^2$, 200 mm$^2$ to about 225 mm$^2$, about 225 mm$^2$ to about 250 mm$^2$, about 250 mm$^2$ to about 300 mm$^2$, about 300 mm$^2$ to about 400 mm$^2$, about 400 mm$^2$ to about 500 mm$^2$, about 500 mm$^2$ to about 750 mm$^2$, about 750 mm$^2$ to about 1000 mm$^2$, or about 1000 mm$^2$ or more.

The imaging sensor may be positioned at any suitable distance from the flow cytometer flow stream so long as the detection field is capable of capturing an image of the flow stream. For example, the imaging sensor may be positioned 0.01 mm or more from the flow stream, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more from the flow cytometer flow stream.

In some embodiments, the imaging sensor is positioned at an angle with respect to the flow stream axis. For example, the imaging sensor may be positioned at an angle with respect to the axis of the flow stream which ranges from 10° to 90°, such as from 15° to 85°, such as from 20° to 80°, such as from 25° to 75° and including from 30° to 60°. In certain embodiments, the imaging sensor is positioned at a 90° angle with respect to the axis of the flow stream.

In some embodiments, the imaging sensor also includes an optical adjustment protocol. By "optical adjustment" is meant that capturing images of the detection field by the imaging sensor may be changed as desired, such as to increase or decrease the captured dimensions or to enhance the optical resolution of the image. In some embodiments, optical adjustment is a magnification protocol configured to increase the size of the detection field captured by the imaging sensor, such as by 5% or greater, such as by 10% or greater, such as by 25% or greater, such as by 50% or greater and including increasing the detection field of the imaging sensor by 75% or greater. In other instances, optical adjustment is a de-magnification protocol configured to decrease the size of the detection field captured by the imaging sensor, such as by 5% or greater, such as by 10% or greater, such as by 25% or greater, such as by 50% or greater and including decreasing the width of the slit shaped beam by 75% or greater. In certain embodiments, optical adjustment is an enhanced resolution protocol configured to improve the resolution of the captured images, such as by 5% or greater, such as by 10% or greater, such as by 25% or greater, such as by 50% or greater and including enhancing the resolution of the captured images by 75% or greater. Capturing images of the detection field by the imaging sensor may be adjusted with any convenient optical adjustment protocol, including but not limited to lens, mirrors, filters and combinations thereof. In certain embodiments, the imaging sensor includes a focusing lens. The focusing lens, for example may be a de-magnifying lens. In other embodiments, the focusing lens is a magnifying lens.

Imaging sensors of the present disclosure may also include one or more wavelength separators. The term "wavelength separator" is used herein in its conventional sense to refer to an optical protocol for separating polychromatic light into its component wavelengths for detection. Wavelength separation, according to certain embodiments, may include selectively passing or blocking specific wavelengths or wavelength ranges of the polychromatic light. To separate wavelengths of light, the transmitted light may be passed through any convenient wavelength separating protocol, including but not limited to colored glass, bandpass filters, interference filters, dichroic mirrors, diffraction gratings, monochromators and combinations thereof, among other wavelength separating protocols. Depending on the detection field, light source and flow stream being visualized, systems may include one or more wavelength separators, such as two or more, such as three or more, such as four or more, such as five or more and including 10 or more wavelength separators. In one example, imaging sensors include one bandpass filter. In another example, imaging sensors include two or more bandpass filters. In another example, imaging sensors include two or more bandpass filters and a diffraction grating. In yet another example, imaging sensors include a plurality of bandpass filters and a monochromator. In certain embodiments, imaging sensors include a plurality of bandpass filters and diffraction gratings configured into a filter wheel setup. Where imaging sensors include two or more wavelength separators, the wavelength separators may be utilized individually or in series to separate polychromatic light into component wavelengths. In some embodiments, wavelength separators are arranged in series. In other embodiments, wavelength separators are arranged individually such that one or more measurements are conducted using each of the wavelength separators.

In some embodiments, systems include one or more optical filters, such as one or more bandpass filters. For example, in some embodiments the optical filters of interest are bandpass filters having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm. In other instances, the optical filters are longpass filters, such as for example longpass filters which attenuate wavelengths of light of 1600 nm or less, such as 1550 nm or less, such as 1500 nm or less, such as 1450 nm or less, such as 1400 nm or less, such as 1350 nm or less, such as 1300 nm or less, such as 1000 nm or less, such as 950 nm or less, such as 900 nm or less, such as 850 nm or less, such as 800 nm or less, such as 750 nm or less, such as 700 nm or less, such as 650 nm or less, such as 600 nm or less, such as 550 nm or less, such as 500 nm or less and including a longpass filter which attenuates wavelengths of light of 450 nm or less. In yet other instances, the optical filters are shortpass filters, such as for example shortpass filters which attenuate wavelengths of light of 200 nm or greater, such as 250 nm or greater, such as 300 nm or greater, such as 350 nm or greater, such as 400 nm or greater, such as 450 nm or greater, such as 500 nm or greater, such as 550 nm or greater and including shortpass filters which attenuate wavelengths of light of 600 nm or greater.

In other embodiments, the wavelength separator is a diffraction grating. Diffraction gratings may include, but are not limited to transmission, dispersive or reflective diffraction gratings. Suitable spacings of the diffraction grating may vary depending on the configuration of the light source, detection field and imaging sensor and other optical adjust protocols present (e.g., focusing lens), ranging from 0.01 μm to 10 μm, such as from 0.025 μm to 7.5 μm, such as from 0.5 μm to 5 μm, such as from 0.75 μm to 4 μm, such as from 1 μm to 3.5 μm and including from 1.5 μm to 3.5 μm.

In some embodiments, each imaging sensor is operably coupled to one or more light sources for illuminating the flow stream in the detection field. In some embodiments, the light source is a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 200 nm to 1500 nm. Another example of a suitable broadband light source includes a light source that emits light having wavelengths from 400 nm to 1000 nm. Any convenient broadband light source protocol may be employed, such as a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, the light source is a narrow band light source emitting a particular wavelength or a narrow range of wavelengths. In some embodiments, the narrow band light sources emit light having a narrow range of wavelengths, such as for example, 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Any convenient narrow band light source protocol may be employed, such as a narrow wavelength LED, laser diode or a broadband light source coupled to one or more optical bandpass filters, diffraction gratings, monochromators or any combination thereof.

The subject systems may include one or more light sources, as desired, such as two or more light sources, such as three or more light sources, such as four or more light sources, such as five or more light sources and including ten or more light sources. The light source may include an combination of types of light sources, for example, where two lights sources are employed, a first light source may be a broadband white light source (e.g., broadband white light LED) and second light source may be a broadband near-infrared light source (e.g., broadband near-IR LED). In other instances, where two light sources are employed, a first light source may be a broadband white light source (e.g., broadband white light LED) and the second light source may be a narrow spectra light source (e.g., a narrow band visible light or near-IR LED). In yet other instances, the light source is an plurality of narrow band light sources each emitting specific wavelengths, such as an array of two or more LEDs, such as an array of three or more LEDs, such as an array of five or more LEDs, including an array of ten or more LEDs.

In some embodiments, light sources emit light having wavelengths ranging from 200 nm to 1500 nm, such as from 250 nm to 1250 nm, such as from 300 nm to 1000 nm, such as from 350 nm to 900 nm and including from 400 nm to 800 nm. For example, the light source may include a broadband light source emitting light having wavelengths from 200 nm to 900 nm. In other instances, the light source includes a plurality of narrow band light sources emitting wavelengths ranging from 200 nm to 900 nm. For example, the light source may be plurality of narrow band LEDs (1 nm-25 nm) each independently emitting light having a range of wavelengths between 200 nm to 900 nm. In some embodiments, the narrow band light source is one or more narrow band lamps emitting light in the range of 200 nm to 900 nm, such as a narrow band cadmium lamp, cesium lamp, helium lamp, mercury lamp, mercury-cadmium lamp, potassium lamp, sodium lamp, neon lamp, zinc lamp or any combination thereof.

In certain embodiments, the light source is a stroboscopic light source where the flow stream is illuminated with periodic flashes of light. Depending on the light source (e.g., flash lamp, pulsed laser) the frequency of light strobe may vary, and may be 0.01 kHz or greater, such as 0.05 kHz or greater, such as 0.1 kHz or greater, such as 0.5 kHz or greater, such as 1 kHz or greater, such as 2.5 kHz or greater, such as 5 kHz or greater, such as 10 kHz or greater, such as 25 kHz or greater, such as 50 kHz or greater and including 100 kHz or greater. In these embodiments, the strobe light may be operably coupled to a processor having a frequency generator which regulates strobe frequency. In some embodiments, the frequency generator is coupled to the droplet drive generator such that the strobe light is synchronized with droplet generation. In other instances, the frequency generator of the strobe light is operably coupled to the one or more optical sensors such that the frequency of the strobe light is synchronized with the frequency of image capture. In certain instances, suitable strobe light sources and frequency controllers include, but are not limited to those described in U.S. Pat. Nos. 5,700,692 and 6,372,506, the disclosures of which are herein incorporated by reference. Strobing and pulsed light sources are also described in Sorenson, et al. *Cytometry*, Vol. 14, No. 2, pages 115-22 (1993); Wheeless, et al. *The Journal of Histochemistry and Cytochemistry*, Vol. 24, No. 1, pages 265-268 (1976), the disclosures of which are herein incorporated by reference.

Sample Introduction

After aligning an alignment microwell array, sample droplets can be introduced into a microwell array, for example a sample microwell array. In some embodiments, a plurality of sample droplets can be introduced into a sample microwell array. In some embodiments, the methods can comprise introducing a sample droplet into a microwell of a sample microwell array based on the first parameter and the second parameter. In some embodiments, the methods can comprise introducing a plurality of sample droplets into microwells of the sample microwell array based on the first parameter and the second parameter. In some embodiments, the methods can comprise introducing a plurality of sample droplets into microwells of the sample microwell array based on the parameters (parameter$_{x,m}$; parameter$_{y,m}$) of the $m^{th}$ alignment droplet to produce the sample microwell array. The content of the sample droplets can vary. In some embodiments, the sample droplets can comprise cells, synthetic particles, and any combination thereof.

Cell Types

The types of cells that can be deposited by the methods, compositions and systems disclosed herein to produce high density array can vary. In some embodiments, the cells are bacterial cells, which can be cells from gram-positive or gram-negative bacteria. Examples of bacteria that can be analyzed using the disclosed methods, devices, and systems include, but are not limited to, Actinomedurae, *Actinomyces israelii, Bacillus anthracis, Bacillus cereus, Clostridium botulinum, Clostridium difficile, Clostridium perfringens, Clostridium tetani, Corynebacterium, Enterococcus faecalis, Listeria monocytogenes, Nocardia, Propionibacterium acnes, Staphylococcus aureus, Staphylococcus epiderm, Streptococcus mutans, Streptococcus pneumoniae* and the like. Gram negative bacteria include, but are not limited to, *Afipia felis, Bacteroides, Bartonella bacilliformis, Bortadella pertussis, Borrelia burgdorferi, Borrelia recurrentis, Brucella, Calymmatobacterium granulomatis, Campylobacter, Escherichia coli, Francisella tularensis, Gardnerella vaginalis, Haemophilius aegyptius, Haemophilius ducreyi, Haemophilius influenziae, Heliobacter pylori, Legionella pneumophila, Leptospira interrogans, Neisseria meningitidia, Porphyromonas gingivalis, Providencia sturti, Pseudomonas aeruginosa, Salmonella enteridis, Salmonella typhi, Serratia marcescens, Shigella boydii, Streptobacillus moniliformis, Streptococcus pyogenes, Treponema pallidum, Vibrio cholerae, Yersinia enterocolitica, Yersinia pestis* and the like. Other bacteria can include *Myobacterium avium, Myobacterium leprae, Myobacterium tuberculosis, Bartonella henseiae, Chlamydia psittaci, Chlamydia trachomatis, Coxiella burnetii, Mycoplasma pneumoniae, Rickettsia akari, Rickettsia prowazekii, Rickettsia rickettsii, Rickettsia tsutsugamushi, Rickettsia typhi, Ureaplasma urealyticum, Diplococcus pneumoniae, Ehrlichia chafensis, Enterococcus faecium*, Meningococci and the like.

In some embodiments, the cells are fungi. Non-limiting examples of fungi that can be analyzed using the disclosed methods, devices, and systems include, but are not limited to, Aspergilli, Candidae, *Candida albicans, Coccidioides immitis*, Cryptococci, and combinations thereof.

In some embodiments, the cells are protozoans or other parasites. Examples of parasites to be analyzed using the methods, devices, and systems of the present disclosure include, but are not limited to, *Balantidium coli, Cryptosporidium parvum, Cyclospora cayatanensis, Encephalitozoa, Entamoeba histolytica, Enterocytozoon bieneusi, Giardia lamblia, Leishmaniae, Plasmodii, Toxoplasma gondii*, Trypanosomae, trapezoidal amoeba, worms (e.g., helminthes), particularly parasitic worms including, but not limited to, Nematoda (roundworms, e.g., whipworms, hookworms, pinworms, ascarids, filarids and the like), Cestoda (e.g., tapeworms).

As used herein, the term "cell" can refer to one or more cells. In some embodiments, the cells are normal cells, for example, human cells in different stages of development, or human cells from different organs or tissue types (e.g. white blood cells, red blood cells, platelets, epithelial cells, endothelial cells, neurons, glial cells, fibroblasts, skeletal muscle cells, smooth muscle cells, gametes, or cells from the heart, lungs, brain, liver, kidney, spleen, pancreas, thymus, bladder, stomach, colon, small intestine). In some embodiments, the cells can be undifferentiated human stem cells, or human stem cells that have been induced to differentiate. In some embodiments, the cells can be fetal human cells, for example the fetal human cells obtained from a mother pregnant with the fetus. In some embodiments, the cells can be rare cells. A rare cell can be, for example, a circulating tumor cell (CTC), circulating epithelial cell, circulating endothelial cell, circulating endometrial cell, circulating stem cell, stem cell, undifferentiated stem cell, cancer stem cell, bone marrow cell, progenitor cell, foam cell, mesenchymal cell, trophoblast, immune system cell (host or graft), cellular fragment, cellular organelle (e.g. mitochondria or nuclei), pathogen infected cell, and the like.

In some embodiments, the cells are non-human cells, for example, other types of mammalian cells (e.g. mouse, rat, pig, dog, cow, or horse). In some embodiments, the cells are other types of animal or plant cells. In other embodiments, the cells can be any prokaryotic or eukaryotic cells.

In some embodiments, a first cell sample is obtained from a person not having a disease or condition, and a second cell sample is obtained from a person having the disease or condition. In some embodiments, the persons are different. In some embodiments, the persons are the same but cell samples are taken at different time points. In some embodiments, the persons are patients, and the cell samples are patient samples. The disease or condition can be a cancer, a bacterial infection, a viral infection, an inflammatory disease, a neurodegenerative disease, a fungal disease, a parasitic disease, a genetic disorder, or any combination thereof.

In some embodiments, cells suitable for use in the presently disclosed methods can range in size from about 2 micrometers to about 100 micrometers in diameter. In some embodiments, the cells can have diameters of or of about 2, 5, 10, 15, 20, 30, 40, 50, 60, 70, 80, 90, 100 micrometers, or a number or a range between any two of these values. In some embodiments, the cells can have diameters of at least, or at most, 2, 5, 10, 15, 20, 30, 40, 50, 60, 70, 80, 90, or 100 micrometers. In some embodiments, the cells have diameters of about 10 micrometers.

In some embodiments the cells are sorted prior to associating a cell with a bead. For example the cells can be sorted by fluorescence-activated cell sorting or magnetic-activated cell sorting, or more generally by flow cytometry. The cells can be filtered by size. In some embodiments a retentate contains the cells to be associated with the bead. In some embodiments the flow through contains the cells to be associated with the bead.

A sample can refer to a plurality of cells. The sample can refer to a monolayer of cells. The sample can refer to a thin section (e.g., tissue thin section). The sample can refer to a solid or semi-solid collection of cells that can be place in one dimension on an array.

Realignment

After aligning an alignment microwell array and prior to introducing sample droplets into a microwell array, for example a sample microwell array, the methods can comprise introducing additional alignment droplets into an alignment microwell array, for example the second alignment microwell array. In some embodiments, the methods can comprise introducing an alignment droplet, for example a second alignment droplet, into a microwell of an alignment microwell array, for example a second alignment microwell array, before the one or more sample droplets are introduced into the microwells of the sample array.

In some embodiments, the methods can comprise determining the alignment droplet's location on the alignment microwell array, for example the second alignment droplet's location on the second alignment microwell array, using the first imaging sensor. In some embodiments, the methods can comprise determining the alignment droplet's location on the alignment microwell array using the second imaging sensor. In some embodiments, the methods can comprise determining the alignment droplet's location on the alignment microwell array using the first imaging sensor and second imaging sensor. In some embodiments, introducing the sample droplets into the microwells of the sample microwell array can be further based on the second alignment droplet's location on the second alignment array.

Systems

Disclosed herein are systems for producing arrays, for example a cellular array, a synthetic particle array, or a reagent array. In some embodiments, the systems can comprise: a cell sorting component configured to: flow cytometrically introducing droplets into microwells of a microwell array to produce a cellular array. In some embodiments, the microwell array can comprise 500 or more microwells per inch. In some embodiments, determining the first parameter and the second parameter can comprise flow cytometrically depositing an alignment droplet, for example a first alignment droplet, onto a microwell of an alignment microwell array, for example a first alignment microwell array. In some embodiments, the system can comprise the microwell array, wherein the microwell array can in a droplet receiving relationship to the cell sorting component.

In some embodiments, the systems can comprise a control component, for example the alignment controller 418 configured to: receiving a desired location in an x direction and a y direction on the microwell array; and determining a first parameter using a first imaging sensor and a second parameter using a second imaging sensor for introducing the droplet into a microwell of the microwell array. In some embodiments, the first imaging sensor and the second imaging sensor can be approximately orthogonal to each other. In some embodiments, one or both of the first imaging sensor and the second imaging sensor can be between a waste receiving vessel and the microwell array. In some embodiments, the distance between the droplet's location and the desired location can be within a threshold, for example a predetermined threshold.

In some embodiments, the control component can be further configured to introducing a plurality of cells and/or synthetic particles into microwells of the microwell array based on the first parameter and the second parameter.

In some embodiments, the control component can further configured to: prior to introducing the plurality of cells into the microwells of the microwell array, introducing a second alignment droplet into a microwell of a second alignment microwell array; and determining the second alignment droplet's location on the second alignment microwell array, wherein introducing the plurality of cells into the microwells of the cellular array can be further based on the second alignment droplet's location on the second alignment microwell array.

In some embodiments, the system can comprise a processor, for example the processor 602 shown in FIG. 6, wherein the processor can comprise memory, for example the memory 604, operably coupled to the processor, wherein the memory can include instructions stored thereon. In some embodiments, the processor can be configured to: receiving the desired location in the x direction and the y direction on the microwell array; and determining the first parameter using the first imaging sensor and the second parameter using the second imaging sensor for introducing the droplet into the microwell of the microwell array. In some embodiments, the first imaging sensor and the second imaging sensor can be approximately orthogonal to each other. In some embodiments, one or both of the first imaging sensor and the second imaging sensor can be between a waste receiving vessel, for example the waste receiving vessel 338b, and the microwell array, for example the microwell array 338a. In some embodiments, the droplet's location and the desired location can be within a threshold, for example a predetermined threshold.

In some embodiments, the system can comprise a processor, wherein the processor can comprise memory operably coupled to the processor, wherein the memory can include instructions stored thereon, wherein the instructions, when executed by the processor, can configure the processor to: receiving the desired location in the x direction and the y direction on the microwell array; and determining the first parameter using the first imaging sensor and the second parameter using the second imaging sensor for introducing the droplet into the microwell of the microwell array, wherein the first imaging sensor and the second imaging sensor can be approximately orthogonal to each other and can be between a waste receiving vessel and the microwell array, and wherein the droplet's location and the desired location can be within a predetermined threshold.

EXAMPLES

Some aspects of the embodiments discussed above are disclosed in further detail in the following examples, which are not in any way intended to limit the scope of the present disclosure.

Example 1

High Density Microwell Array

This example demonstrates production of a high density droplet array.

Figure 7A:
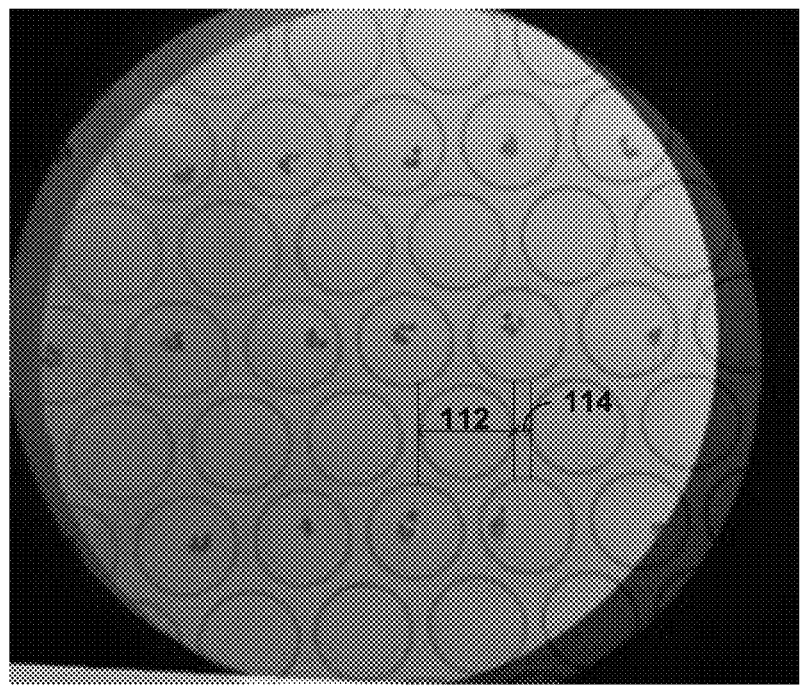
FIGS. 7A-7B show production of high density droplet arrays.
Figure 7B:

Using a modified BD (Franklin Lakes, N.J.) FACSJazz™ cell sorter, 4000 single cells were deposited onto a 1 inch by 3 inch microwell slide density as shown in FIGS. 7A-7B. Microwells on the microwell slide had diameters of 400 micrometers. Microwells on the microwell slide had a center-to-center distance of 480 micrometers, or an edge-to-edge distance of 80 micrometer. The occupancy of the microwells on the microwell slide was adjusted to approximately 50%.

Altogether, these data indicate that high density droplet arrays can be created using a flow cytometer.

Example 2

Aligning a Microwell Array

This example describes aligning a microwell array so samples can be collected at the center of each microwell of a microwell array.

A flow cytometer with a stage is provided. The stage is capable of holding a microwell array. The stage is capable of moving in an x direction and a y direction. The x-axis and the y-axis are aligned independently. A script is written in a programming language such as python. The script includes steps for first aligning a first microwell array on the manufacturing floor and subsequently aligning a second microwell array on the customer site.

The x axis is in the deflection direction of negatively charged droplets created by the flow cytometer. The deflection is caused by a deflection field created by deflection plates of the flow cytometer. The edge of the main stream collector, also referred to as the drain or the waste receiving vessel, is defined. A deflection back camera takes images of the deflected stream as it moves away from the main stream by increasing the drop charge, until the deflected stream passes the drain edge by a distance such as a predetermined threshold. This position is saved in a file as the golden deflected stream x-coordinate for subsequent use at the customer site.

The A1 microwell on the microwell array is aligned such that deflected stream is collected at the center of the A1 microwell. This process is repeated for different types of microwell arrays, and the stage's x-coordinate is saved for each type of microwell array as a stage x-coordinate. At the customer site, every time a sort starts, the deflected stream is sent to the saved golden deflected stream x-coordinate, and the stage is sent to the saved stage x-coordinate in order to deposit samples at the center of each microwell of a microwell array.

The y-axis is perpendicular to the direction of deflection. For alignment in the y direction, a stream image is saved by a side camera, and the y-coordinate of the stream is saved. On the manufacturing floor, for each type of microwell array, the stage is moved until alignment droplets are collected at the center of the A1 microwell of a microwell array in the y direction. The stage's y-coordinate is saved as the stage y-coordinate of the A1 microwell for each type of microwell array. At the user site, every time a sort begins, the position of the deflected stream in the y-axis is measured by the side camera and the displacement from saved stage y-coordinate is calculated, for example, in minimeter. This value is used to move the stage from its originally saved stage y-coordinate of the A1 microwell in order to collect samples at the center of each microwell of a microwell array in the y direction. Thus, the alignment process compensates for any stream displacement including nozzle replacement, by aligning the microwell array at the beginning of each sort at the user site.

Example 3

Fluid Stream Alignment

This example demonstrates aligning fluid streams so samples can be collected at the center of each microwell of a microwell array.

Figure 8:
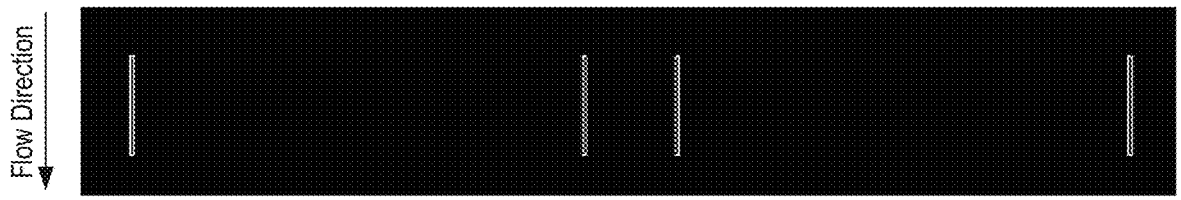
FIG. 8 shows a non-limiting exemplary photograph without a stream.
Figure 9:
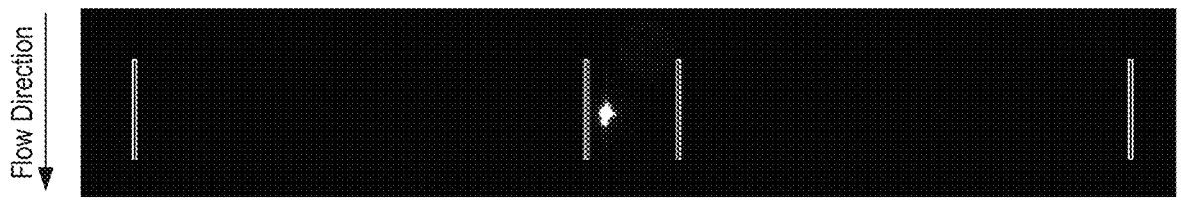
FIG. 9 shows a non-limiting exemplary photograph with a stream in the middle (to the left—ideally should be in the center).
Figure 10:
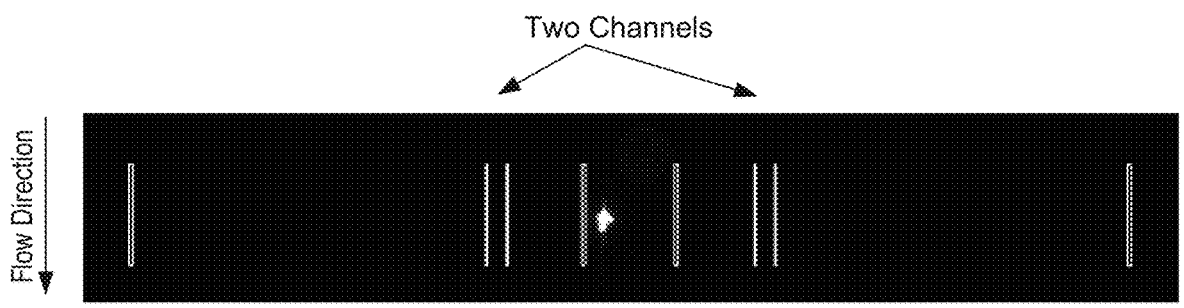
FIG. 10 shows a non-limiting exemplary photograph of a view of a two-channel set-up.
Figure 11:
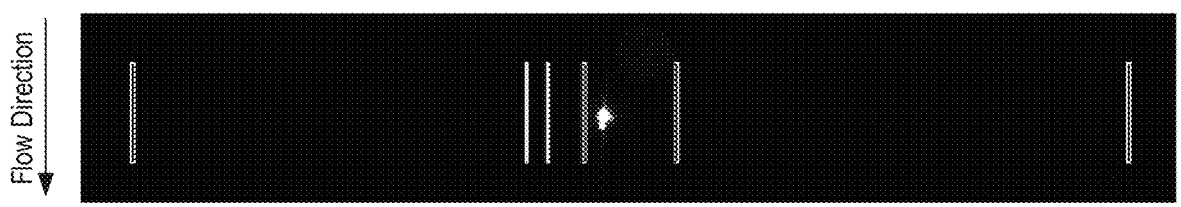
FIG. 11 shows a non-limiting exemplary photograph of an Automated Cell Deposition Unit (ACDU) view (plate sorting).
Figure 12:
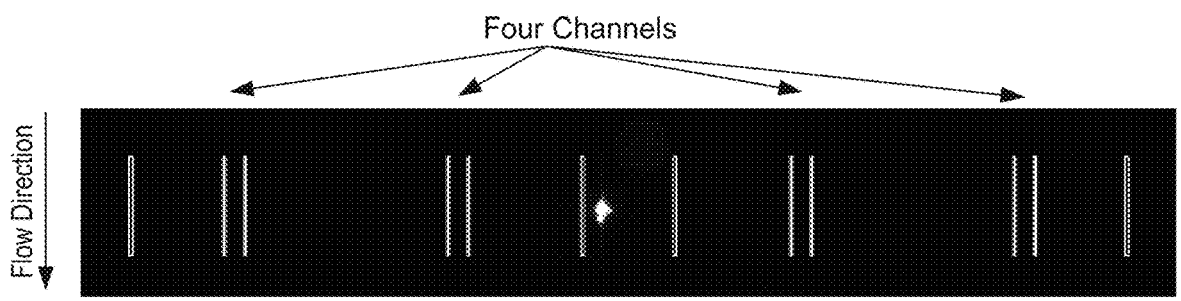
FIG. 12 shows a non-limiting exemplary photograph of a view of four-channel set-up.

In the following figures, each channel was calibrated to a tube (each pair of parallel bars corresponds to a fluid stream that falls into a tube). FIG. 8 shows a non-limiting exemplary photograph without a stream. FIG. 9 shows a non-limiting exemplary photograph with a stream in the middle (to the left—ideally should be in the center). The stream in the middle corresponded to a non-deflected stream (e.g., a stream to be collected in the waste vessel). FIG. 10 shows a non-limiting exemplary photograph of a view of a two-channel set-up. The two channels corresponded to two streams being collected. FIG. 11 shows a non-limiting exemplary photograph of an Automated Cell Deposition Unit (ACDU) view (plate sorting). FIG. 12 shows a non-limiting exemplary photograph of a view of four-channel set-up.

Figure 13:
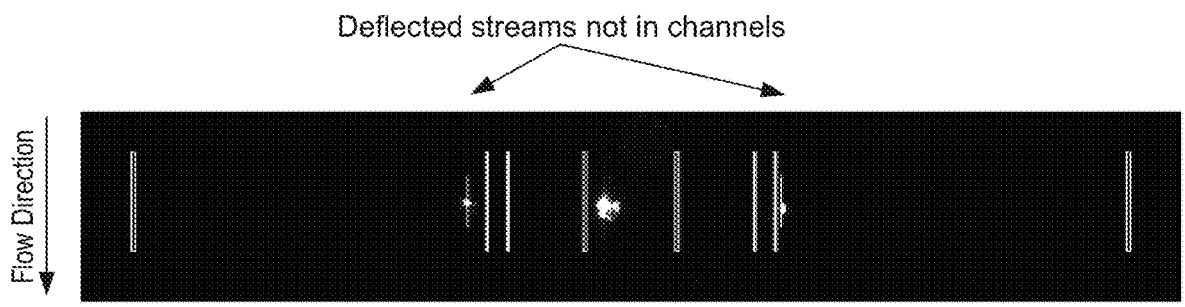
FIG. 13 shows a non-limiting exemplary photograph of a view during calibration—turn on voltage, turn on test sort, dots with vertical lines are deflected streams that were not in a channel.
Figure 14:
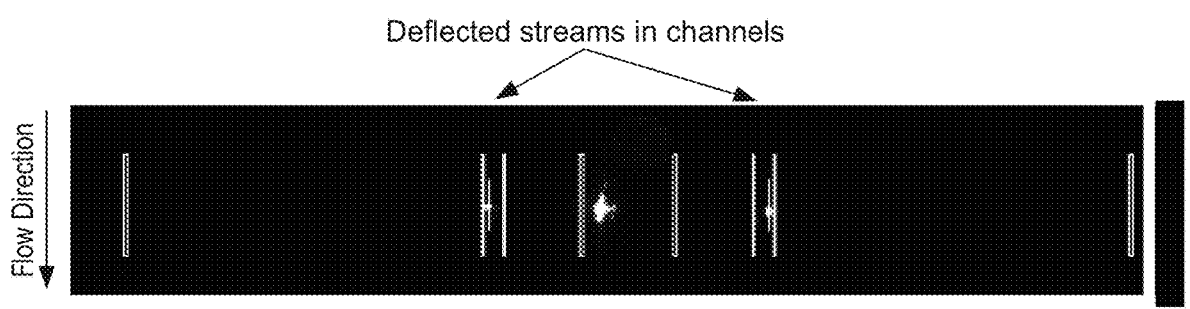
FIG. 14 shows a non-limiting exemplary photograph of adjustment of moving streams shown in FIG. 13 into the channel.
Figure 15:
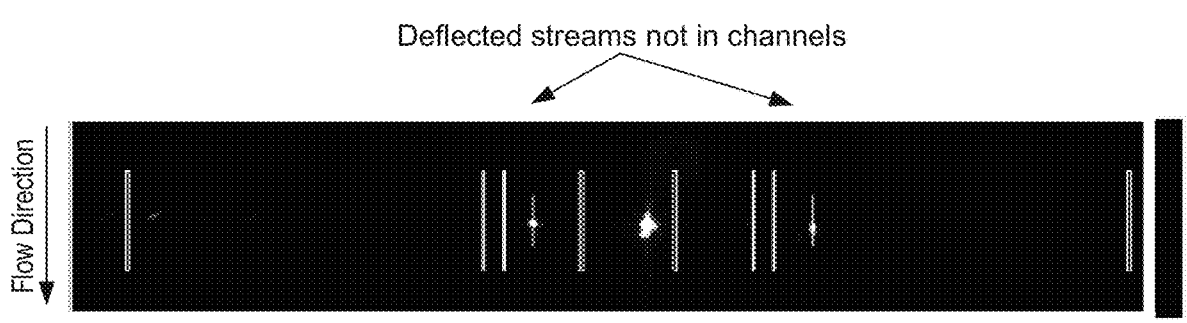
FIG. 15 shows a non-limiting exemplary photograph showing, after a user inserting a different nozzle, the stream being moved to the right and deflected streams also shifted right.
Figure 16:
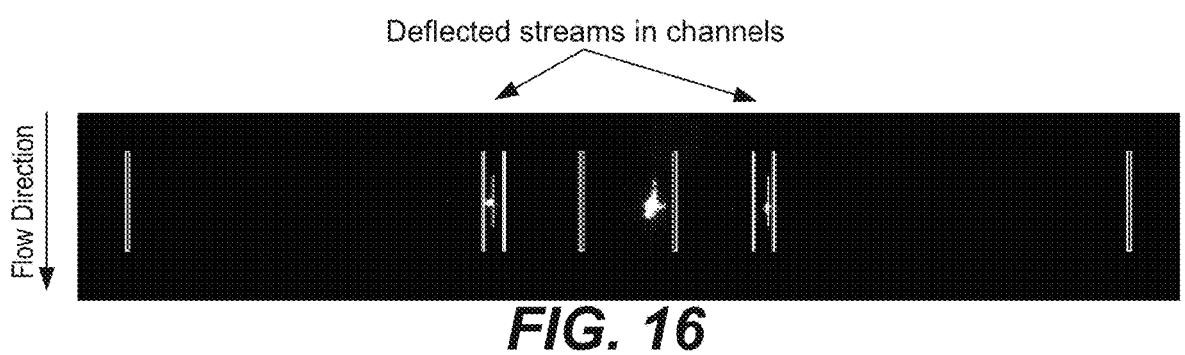
FIG. 16 shows a non-limiting exemplary photograph of the set-up in FIG. 15 with voltage adjusted to bring deflected streams back into preferred channel.

FIG. 13 shows a non-limiting exemplary photograph of a view during calibration. After setting a voltage of deflection, a test sort was performed. Dots with vertical lines are deflected streams that were not in a channel. FIG. 14 shows a non-limiting exemplary photograph of adjustment of moving streams shown in FIG. 13 into the channel. FIG. 15 shows a non-limiting exemplary photograph showing that after a user inserted a different nozzle, the stream being moved to the right and deflected streams also shifted right. FIG. 16 shows a non-limiting exemplary photograph of the set-up in FIG. 15 with the voltage of deflection adjusted to bring deflected streams back into preferred channel.

Altogether, the data indicate that multiple streams can be aligned to multiple channels by adjusting parameters of the streams.

Example 4

Calibrating a Cytometer Sort Stream to Accurately Place Droplets within Collection Plate Destinations This example describes calibrating a cytometer sort stream using a collection plate so droplets of samples can be accurately placed, for example, into microwells of microwell plates.

Figure 17A:
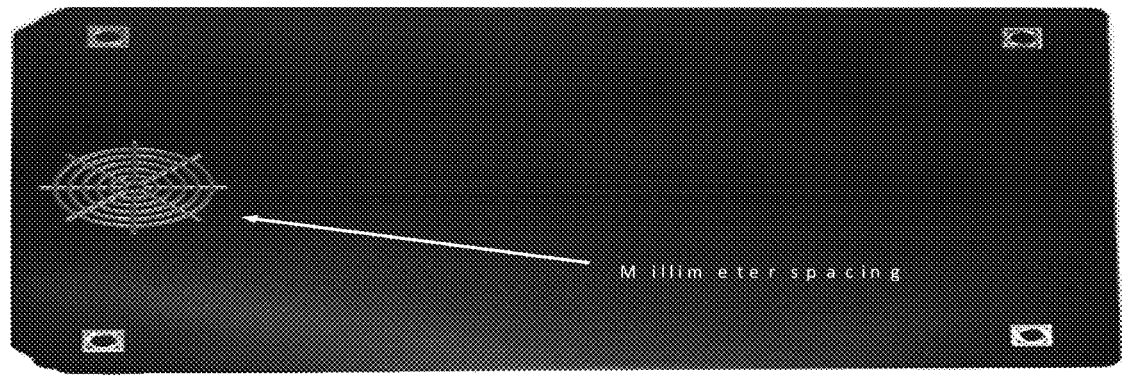
FIGS. 17A-17B show non-limiting exemplary calibration plates.
Figure 17B:
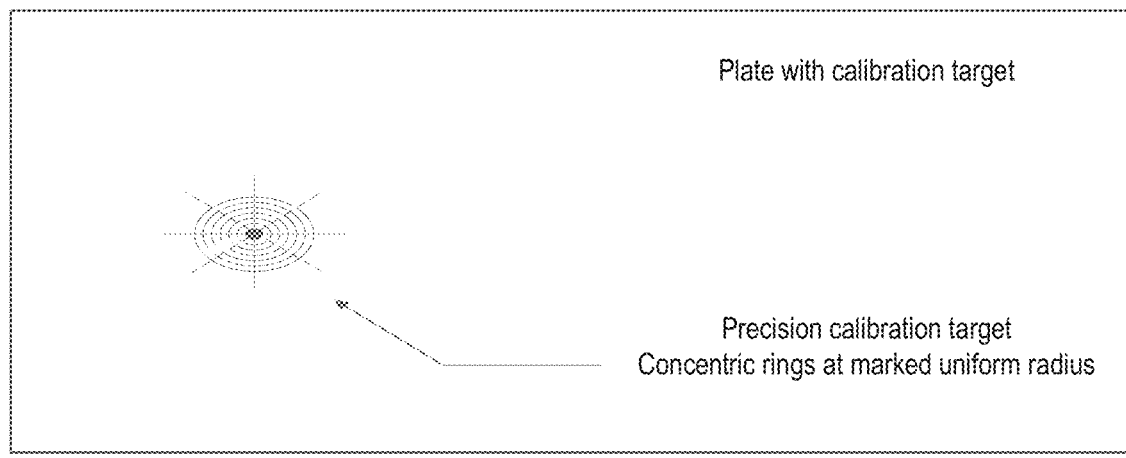

An alignment device (e.g., a high-precision machined template) can be created with a target bullseye. It can have the same size as the plate devices that normally fit in the instrument. The target has markings for one millimeter up to ten millimeters. FIGS. 17A-17B shows the calibration plate. When this is loaded into the instrument and moved to the calibration location it is ready for the sorter to deposit a single drop. The location where the drop is deposited can be inspected by the user. This location is then graphically input into the software.

The software interface helps the user by automatically calculating an x/y offset calibration. After a drop is deposited, the user can locate where the drop is deposited. The user then inputs the location on the graphic using a pointer.

Figure 18A:
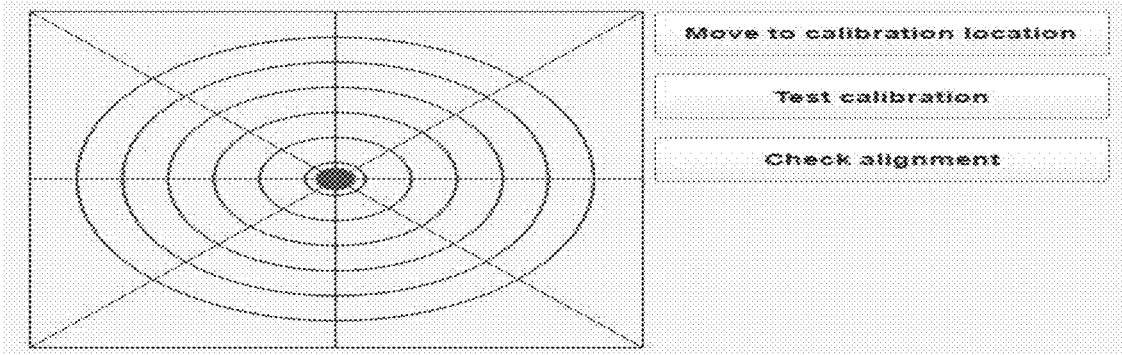
FIGS. 18A-18C show a non-limiting user interface for calibrating a microwell plate.
Figure 18B:
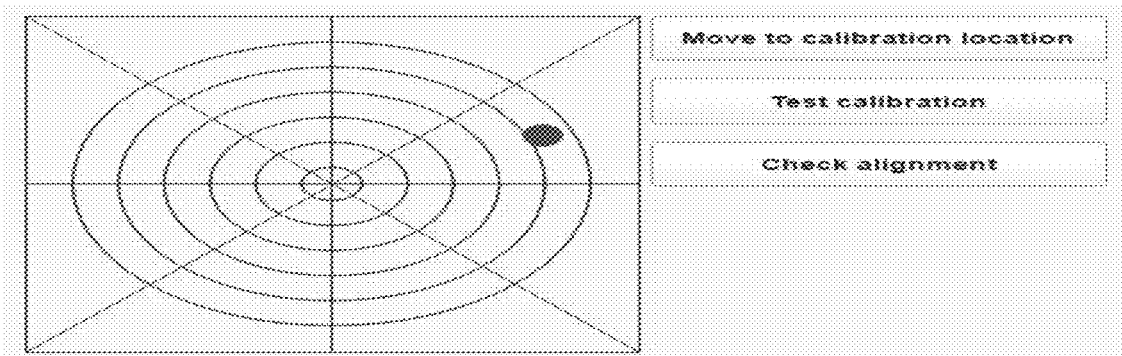
Figure 18C:
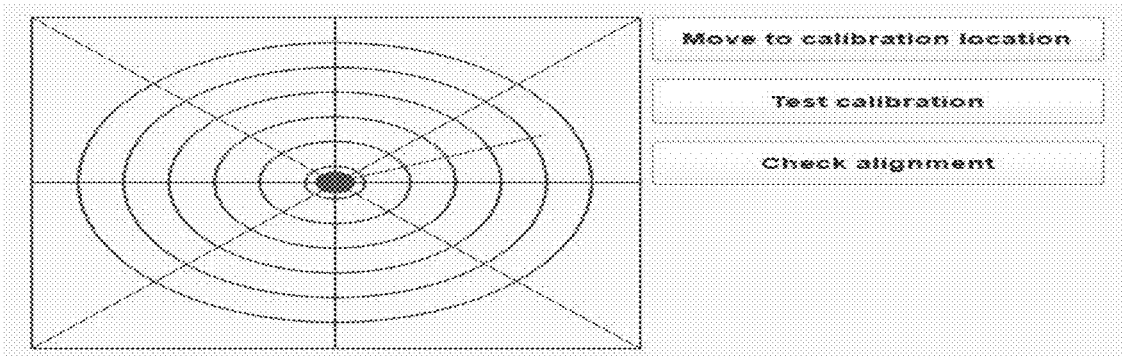

FIGS. 18A-18C show a non-limiting user interface for calibrating a microwell plate. FIG. 18A illustrates that the software shows a representation of the calibration target. The green circle in the center is the offset. To change the offset the user clicks on the green circle and drags it to the location that the user saw the drop deposit. FIG. 18B shows that the user has moved the circle to the location where the drop was deposited. At this point the user clicks on the button "Move to calibration location". This will calculate the required offset for the stepper motors to align the drop in the center. After the button is clicked the offset circle moves back to the center indicating this is the new. FIG. 18C shows that the plate loader is calibrated.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of producing a cellular array, comprising:
providing a sample comprising a plurality of cells; and
depositing the plurality of cells in the sample into microwells of a microwell array from above with a flow cytometer and in droplets that exit the flow cytometer in a downward vertical direction in a flow stream that is directionally steered by deflection plates to produce the cellular array, wherein the microwell array comprises 500 or more microwells per inch$^2$ and 25% or more of the microwells of the cellular array comprise a single cell.

2. The method of claim 1,
wherein introducing the plurality of cells in the sample into the microwells of the microwell array comprises introducing the plurality of cells in the sample into the microwells of the microwell array at a plurality of first desired locations, and
wherein introducing the plurality of cells in the sample into the microwells of the microwell array at the plurality of first desired locations comprises introducing a cell of interest from the plurality of cells at one of the plurality of first desired locations.

3. The method of claim 1, wherein each of the microwells of the microwell array has a volume no more than 1000 nanoliters, wherein each of the microwells of the microwell array has a diameter no more than 1000 micrometers, and wherein at least two of the microwells of the microwell array are separated from each other by no more than 200 micrometers.

4. The method of claim 1, further comprising introducing a reagent into one or more of the microwells of the cellular array.

5. The method of claim 4, wherein the reagent comprises one or more synthetic particles, and wherein the one or more synthetic particles comprise magnetic beads attached to oligonucleotide barcodes.

6. A method of producing a cellular array, comprising:
providing a sample comprising a plurality of cells; and
flow cytometrically depositing the plurality of cells in the sample into microwells of a microwell array to produce the cellular array, wherein the microwell array comprises 500 or more microwells per inch$^2$; and
flow cytometrically depositing one or more synthetic particles into one or more of the microwells of the cellular array, wherein 25% or more of the microwells of the cellular array comprise a single cell and a synthetic particle.

7. The method of claim 6,
wherein introducing the plurality of cells in the sample into the microwells of the microwell array comprises introducing the plurality of cells in the sample into the microwells of the microwell array at a plurality of first desired locations, and
wherein introducing the plurality of cells in the sample into the microwells of the microwell array at the plurality of first desired locations comprises introducing a cell of interest from the plurality of cells at one of the plurality of first desired locations.

8. The method of claim 6, wherein each of the microwells of the microwell array has a volume no more than 1000 nanoliters, wherein each of the microwells of the microwell array has a diameter no more than 1000 micrometers, and wherein at least two of the microwells of the microwell array are separated from each other by no more than 200 micrometers.

9. The method of claim 7, wherein the one or more synthetic particles comprise magnetic beads attached to oligonucleotide barcodes.

10. The method of claim 6, wherein introducing one or more synthetic particles into one or more of the microwells of the cellular array occurs before or after introducing the plurality of cells into microwells of the microwell array.

11. The method of claim 1, wherein the flow cytometrically depositing comprises using a flow cytometer to deposit a single cell at a time into the microwells of the microwell array.

12. The method of claim 5, wherein the introducing of the one or more synthetic particles comprises using a flow cytometer to deposit a single synthetic particle at a time into the microwells of the microwell array.

13. The method of claim 1, wherein the sample further comprises a plurality of cells of interest.

14. The method of claim 13, wherein the introducing further comprises flow cytometrically sorting the cells of interest from cells not of interest in the sample.

15. The method of claim 14, wherein the method further comprises introducing a second plurality of cells of interest into microwells of the microwell array at a plurality of second desired locations.

16. The method of claim 6, wherein the introducing of the one or more synthetic particles comprises flow cytometrically sorting synthetic particles of interest from synthetic particles not of interest in a synthetic particle sample.

17. The method of claim 6, wherein the one or more synthetic particles comprises a first plurality of synthetic particles comprising a first reagent and a second plurality of synthetic particles comprising a second reagent.

* * * * *